United States Patent
Jacobson et al.

(10) Patent No.: US 11,702,662 B2
(45) Date of Patent: *Jul. 18, 2023

(54) COMPOSITIONS AND METHODS FOR HIGH FIDELITY ASSEMBLY OF NUCLEIC ACIDS

(71) Applicant: Gen9, Inc., Boston, MA (US)

(72) Inventors: Joseph Jacobson, Newton, MA (US); Daniel Schindler, Newton Upper Falls, MA (US); Scott S. Lawton, Bedford, MA (US)

(73) Assignee: Gen9, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/373,324

(22) Filed: Jul. 12, 2021

(65) Prior Publication Data

US 2021/0380991 A1  Dec. 9, 2021

Related U.S. Application Data

(63) Continuation of application No. 13/592,827, filed on Aug. 23, 2012, now abandoned.

(60) Provisional application No. 61/527,922, filed on Aug. 26, 2011, provisional application No. 61/532,825, filed on Sep. 9, 2011.

(51) Int. Cl.
| | | |
|---|---|---|
| *C12N 15/66* | (2006.01) | |
| *C12N 15/10* | (2006.01) | |
| *C12P 19/34* | (2006.01) | |
| *G16B 30/00* | (2019.01) | |
| *G16B 30/20* | (2019.01) | |

(52) U.S. Cl.
CPC ............ *C12N 15/66* (2013.01); *C12N 15/10* (2013.01); *C12N 15/1027* (2013.01); *C12N 15/1031* (2013.01); *C12N 15/1089* (2013.01); *C12P 19/34* (2013.01); *G16B 30/00* (2019.02); *G16B 30/20* (2019.02); *C12Q 2521/301* (2013.01); *C12Q 2521/501* (2013.01)

(58) Field of Classification Search
CPC ...... C12N 15/56; C12N 15/1027; C12P 19/34
See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis et al. |
| 4,683,202 A | 7/1987 | Mullis |
| 4,689,405 A | 8/1987 | Frank et al. |
| 4,725,677 A | 2/1988 | Koster et al. |
| 4,800,159 A | 1/1989 | Mullis et al. |
| 4,888,286 A | 12/1989 | Crea |
| 4,959,317 A | 9/1990 | Sauer |
| 4,965,188 A | 10/1990 | Mullis et al. |
| 4,999,294 A | 3/1991 | Looney et al. |
| 5,047,524 A | 9/1991 | Andrus et al. |
| 5,093,251 A | 3/1992 | Richards et al. |
| 5,096,825 A | 3/1992 | Barr et al. |
| 5,104,789 A | 4/1992 | Permar et al. |
| 5,104,792 A | 4/1992 | Silver et al. |
| 5,132,215 A | 7/1992 | Jayaraman et al. |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,395,750 A | 3/1995 | Dillon et al. |
| 5,405,783 A | 4/1995 | Pirrung et al. |
| 5,424,186 A | 6/1995 | Fodor et al. |
| 5,436,150 A | 7/1995 | Chandrasegaran |
| 5,436,327 A | 7/1995 | Southern et al. |
| 5,445,934 A | 8/1995 | Fodor et al. |
| 5,459,039 A | 10/1995 | Modrich et al. |

(Continued)

FOREIGN PATENT DOCUMENTS

| | | |
|---|---|---|
| AU | 2012300401 B2 | 2/2018 |
| CN | 1145641 A | 3/1997 |

(Continued)

OTHER PUBLICATIONS

Extended European Search Report dated Jan. 17, 2022 for Application No. EP 21177267.8.
Extended European Search Report dated Aug. 31, 2015 for Application No. EP 15159715.0.
Extended European Search Report dated Nov. 29, 2019 for Application No. EP 19170699.3.
Communication Relating to the Results of the Partial International Search for International Patent Application PCT/US2012/052036 dated Dec. 17, 2012.
International Search Report and Written Opinion dated Feb. 22, 2013 for Application No. PCT/US2012/052036.
International Preliminary Report on Patentability dated Mar. 4, 2014 for Application No. PCT/US2012/052036.

(Continued)

*Primary Examiner* — Ethan C Whisenant
(74) *Attorney, Agent, or Firm* — Wolf, Greenfield & Sacks, P.C.

(57) ABSTRACT

Aspects of the invention relate to methods, compositions and algorithms for designing and producing a target nucleic acid. The method can include: (1) providing a plurality of blunt-end double-stranded nucleic acid fragments having a restriction enzyme recognition sequence at both ends thereof; (2) producing via enzymatic digestion a plurality of cohesive-end double-stranded nucleic acid fragments each having two different and non-complementary overhangs; (3) ligating the plurality of cohesive-end double-stranded nucleic acid fragments with a ligase; and (4) forming a linear arrangement of the plurality of cohesive-end double-stranded nucleic acid fragments, wherein the unique arrangement comprises the target nucleic acid. In certain embodiments, the plurality of blunt-end double-stranded nucleic acid fragments can be provided by: releasing a plurality of oligonucleotides synthesized on a solid support; and synthesizing complementary strands of the plurality of oligonucleotides using a polymerase based reaction.

22 Claims, 14 Drawing Sheets

Specification includes a Sequence Listing.

(56) References Cited

U.S. PATENT DOCUMENTS

| | | |
|---|---|---|
| 5,474,796 A | 12/1995 | Brennan |
| 5,498,531 A | 3/1996 | Jarrell |
| 5,508,169 A | 4/1996 | Deugau et al. |
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor et al. |
| 5,556,750 A | 9/1996 | Modrich et al. |
| 5,604,097 A | 2/1997 | Brenner |
| 5,605,793 A | 2/1997 | Stemmer |
| 5,624,711 A | 4/1997 | Sundberg et al. |
| 5,639,603 A | 6/1997 | Dower et al. |
| 5,641,658 A | 6/1997 | Adams et al. |
| 5,653,939 A | 8/1997 | Hollis et al. |
| 5,674,742 A | 10/1997 | Northrup et al. |
| 5,679,522 A | 10/1997 | Modrich et al. |
| 5,695,940 A | 12/1997 | Drmanac et al. |
| 5,700,637 A | 12/1997 | Southern |
| 5,700,642 A | 12/1997 | Monforte et al. |
| 5,702,894 A | 12/1997 | Modrich et al. |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor et al. |
| 5,830,655 A | 11/1998 | Monforte et al. |
| 5,830,721 A | 11/1998 | Stemmer et al. |
| 5,834,252 A | 11/1998 | Stemmer et al. |
| 5,858,754 A | 1/1999 | Modrich et al. |
| 5,861,482 A | 1/1999 | Modrich et al. |
| 5,871,902 A | 2/1999 | Weininger et al. |
| 5,877,280 A | 3/1999 | Wetmur |
| 5,912,129 A | 6/1999 | Vinayagamoorthy et al. |
| 5,916,794 A | 6/1999 | Chandrasegaran |
| 5,922,539 A | 7/1999 | Modrich et al. |
| 5,928,905 A | 7/1999 | Stemmer et al. |
| 5,929,208 A | 7/1999 | Heller et al. |
| 5,942,609 A | 8/1999 | Hunkapiller et al. |
| 5,953,469 A | 9/1999 | Zhou |
| 6,008,031 A | 12/1999 | Modrich et al. |
| 6,013,440 A | 1/2000 | Lipshutz et al. |
| 6,017,696 A | 1/2000 | Heller |
| 6,027,877 A | 2/2000 | Wagner, Jr. |
| 6,042,211 A | 3/2000 | Hudson et al. |
| 6,093,302 A | 7/2000 | Montgomery |
| 6,103,463 A | 8/2000 | Chetverin et al. |
| 6,110,668 A | 8/2000 | Strizhov et al. |
| 6,136,568 A | 10/2000 | Hiatt et al. |
| 6,143,527 A | 11/2000 | Pachuk et al. |
| 6,150,102 A | 11/2000 | Mills, Jr. et al. |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson et al. |
| 6,248,521 B1 | 6/2001 | Van Ness et al. |
| 6,261,797 B1 | 7/2001 | Sorge et al. |
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer |
| 6,315,958 B1 | 11/2001 | Singh-Gasson et al. |
| 6,322,971 B1 | 11/2001 | Chetverin et al. |
| 6,326,489 B1 | 12/2001 | Church et al. |
| 6,333,153 B1 | 12/2001 | Fishel et al. |
| 6,346,399 B1 | 2/2002 | Weissman et al. |
| 6,355,412 B1 | 3/2002 | Stewart et al. |
| 6,355,423 B1 | 3/2002 | Rothberg et al. |
| 6,358,712 B1 | 3/2002 | Jarrell et al. |
| 6,365,355 B1 | 4/2002 | McCutchen-Maloney |
| 6,372,429 B1 | 4/2002 | Sharon |
| 6,372,434 B1 | 4/2002 | Weissman et al. |
| 6,372,484 B1 | 4/2002 | Ronchi et al. |
| 6,375,903 B1 | 4/2002 | Cerrina et al. |
| 6,376,246 B1 | 4/2002 | Crameri et al. |
| 6,406,847 B1 | 6/2002 | Cox et al. |
| 6,410,220 B1 | 6/2002 | Hodgson et al. |
| 6,416,164 B1 | 7/2002 | Stearns et al. |
| 6,426,184 B1 | 7/2002 | Gao et al. |
| 6,432,360 B1 | 8/2002 | Church |
| 6,444,111 B1 | 9/2002 | Montgomery |
| 6,444,175 B1 | 9/2002 | Singh-Gasson et al. |
| 6,444,650 B1 | 9/2002 | Cech et al. |
| 6,444,661 B1 | 9/2002 | Barton et al. |
| 6,472,184 B1 | 10/2002 | Hegemann et al. |
| 6,479,652 B1 | 11/2002 | Crameri et al. |
| 6,480,324 B2 | 11/2002 | Quate et al. |
| 6,489,146 B2 | 12/2002 | Stemmer et al. |
| 6,495,318 B2 | 12/2002 | Harney |
| 6,506,603 B1 | 1/2003 | Stemmer et al. |
| 6,509,156 B1 | 1/2003 | Stewart |
| 6,511,849 B1 | 1/2003 | Wang |
| 6,514,704 B2 | 2/2003 | Bruce et al. |
| 6,521,427 B1 | 2/2003 | Evans |
| 6,534,271 B2 | 3/2003 | Furste et al. |
| 6,537,776 B1 | 3/2003 | Short |
| 6,565,727 B1 | 5/2003 | Shenderov |
| 6,586,211 B1 | 7/2003 | Stabler et al. |
| 6,593,111 B2 | 7/2003 | Baric et al. |
| 6,596,239 B2 | 7/2003 | Williams et al. |
| 6,605,451 B1 | 8/2003 | Marmaro et al. |
| 6,610,499 B1 | 8/2003 | Fulwyler et al. |
| 6,613,581 B1 | 9/2003 | Wada et al. |
| 6,632,641 B1 | 10/2003 | Brennan et al. |
| 6,650,822 B1 | 11/2003 | Zhou |
| 6,658,802 B2 | 12/2003 | Lucas, Jr. et al. |
| 6,660,475 B2 | 12/2003 | Jack et al. |
| 6,664,112 B2 | 12/2003 | Mulligan et al. |
| 6,664,388 B2 | 12/2003 | Nelson |
| 6,670,127 B2 | 12/2003 | Evans |
| 6,670,605 B1 | 12/2003 | Storm, Jr. et al. |
| 6,800,439 B1 | 10/2004 | McGall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 6,846,655 B1 | 1/2005 | Wagner et al. |
| 6,897,025 B2 | 5/2005 | Cox et al. |
| 6,911,132 B2 | 6/2005 | Pamula et al. |
| 6,921,818 B2 | 7/2005 | Sproat |
| 6,932,097 B2 | 8/2005 | Ellson et al. |
| 6,946,296 B2 | 9/2005 | Patten et al. |
| 6,955,901 B2 | 10/2005 | Schouten |
| 6,969,587 B2 | 11/2005 | Taylor |
| 6,969,847 B2 | 11/2005 | Davis et al. |
| 7,090,333 B2 | 8/2006 | Mutz et al. |
| 7,133,782 B2 | 11/2006 | Odedra |
| 7,144,734 B2 | 12/2006 | Court et al. |
| 7,169,560 B2 | 1/2007 | Lapidus et al. |
| 7,179,423 B2 | 2/2007 | Bohm et al. |
| 7,183,406 B2 | 2/2007 | Belshaw et al. |
| 7,199,233 B1 | 4/2007 | Jensen et al. |
| 7,262,031 B2 | 8/2007 | Lathrop et al. |
| 7,273,730 B2 | 9/2007 | Du Breuil Lastrucci |
| 7,285,835 B2 | 10/2007 | Rizzo et al. |
| 7,303,872 B2 | 12/2007 | Sussman |
| 7,323,320 B2 | 1/2008 | Oleinikov |
| 7,399,590 B2 | 7/2008 | Piepenburg et al. |
| 7,432,055 B2 | 10/2008 | Pemov et al. |
| 7,498,176 B2 | 3/2009 | McCormick et al. |
| 7,537,897 B2 | 5/2009 | Brenner et al. |
| 7,563,600 B2 | 7/2009 | Oleinikov |
| 7,699,979 B2 | 4/2010 | Li et al. |
| 7,723,077 B2 | 5/2010 | Young et al. |
| 7,820,412 B2 | 10/2010 | Belshaw et al. |
| 7,879,580 B2 | 2/2011 | Can et al. |
| 7,932,025 B2 | 4/2011 | Carr |
| 8,053,191 B2 | 11/2011 | Blake |
| 8,058,004 B2 | 11/2011 | Oleinikov |

(56) References Cited

U.S. PATENT DOCUMENTS

| | | |
|---|---|---|
| 8,137,906 B2 | 3/2012 | Schatz |
| 8,173,368 B2 | 5/2012 | Staehler et al. |
| 8,338,091 B2 | 12/2012 | Chesnut et al. |
| 8,476,018 B2 | 7/2013 | Brenner |
| 8,716,467 B2 | 5/2014 | Jacobson |
| 8,808,986 B2 | 8/2014 | Jacobson |
| 9,023,601 B2 | 5/2015 | Oleinikov |
| 9,023,649 B2 | 5/2015 | Mali et al. |
| 9,051,666 B2 | 6/2015 | Oleinikov |
| 9,150,853 B2 | 10/2015 | Hudson |
| 9,295,965 B2 | 3/2016 | Jacobson et al. |
| 9,322,037 B2 | 4/2016 | Liu et al. |
| 9,752,176 B2 | 9/2017 | Kung et al. |
| 2001/0012537 A1 | 8/2001 | Anderson et al. |
| 2001/0031483 A1 | 10/2001 | Sorge et al. |
| 2001/0049125 A1 | 12/2001 | Stemmer et al. |
| 2001/0053519 A1 | 12/2001 | Fodor et al. |
| 2002/0012616 A1 | 1/2002 | Zhou et al. |
| 2002/0025561 A1 | 2/2002 | Hodgson |
| 2002/0037579 A1 | 3/2002 | Ellson et al. |
| 2002/0058275 A1 | 5/2002 | Fishel et al. |
| 2002/0081582 A1 | 6/2002 | Gao et al. |
| 2002/0127552 A1 | 9/2002 | Church et al. |
| 2002/0132259 A1 | 9/2002 | Wagner et al. |
| 2002/0132308 A1 | 9/2002 | Liu et al. |
| 2002/0133359 A1 | 9/2002 | Brown |
| 2002/0187476 A1 | 12/2002 | Koroulis et al. |
| 2003/0017552 A1 | 1/2003 | Jarrell et al. |
| 2003/0044980 A1 | 3/2003 | Mancebo et al. |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri et al. |
| 2003/0068633 A1 | 4/2003 | Belshaw et al. |
| 2003/0068643 A1 | 4/2003 | Brennan et al. |
| 2003/0082630 A1 | 5/2003 | Kolkman et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0165841 A1 | 9/2003 | Burgin et al. |
| 2003/0170616 A1 | 9/2003 | Wang et al. |
| 2003/0171325 A1 | 9/2003 | Gascoyne et al. |
| 2003/0175907 A1 | 9/2003 | Frazer et al. |
| 2003/0186226 A1 | 10/2003 | Brennan et al. |
| 2003/0198948 A1 | 10/2003 | Stabler et al. |
| 2003/0215837 A1 | 11/2003 | Frey et al. |
| 2003/0215855 A1 | 11/2003 | Dubrow et al. |
| 2003/0215856 A1 | 11/2003 | Church et al. |
| 2003/0219781 A1 | 11/2003 | Frey |
| 2003/0224439 A1* | 12/2003 | Lafferty ............... C12Q 1/6874 435/6.12 |
| 2003/0224521 A1 | 12/2003 | Court et al. |
| 2004/0002103 A1 | 1/2004 | Short |
| 2004/0005673 A1 | 1/2004 | Jarrell et al. |
| 2004/0009479 A1 | 1/2004 | Wohlgemuth et al. |
| 2004/0009520 A1 | 1/2004 | Albert et al. |
| 2004/0014083 A1 | 1/2004 | Yuan et al. |
| 2004/0053362 A1 | 3/2004 | De Luca et al. |
| 2004/0096891 A1 | 5/2004 | Bennett |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0106728 A1 | 6/2004 | McGall et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0171047 A1 | 9/2004 | Dahl et al. |
| 2004/0185484 A1 | 9/2004 | Costa et al. |
| 2004/0229359 A1 | 11/2004 | Mead et al. |
| 2004/0241655 A1 | 12/2004 | Hwang et al. |
| 2004/0259146 A1 | 12/2004 | Friend et al. |
| 2005/0053997 A1 | 3/2005 | Evans |
| 2005/0069928 A1 | 3/2005 | Nelson et al. |
| 2005/0079510 A1 | 4/2005 | Berka et al. |
| 2005/0089889 A1 | 4/2005 | Ramsing et al. |
| 2005/0106606 A1 | 5/2005 | Parker et al. |
| 2005/0112574 A1 | 5/2005 | Gamble et al. |
| 2005/0118628 A1 | 6/2005 | Evans |
| 2005/0130156 A1 | 6/2005 | Frey et al. |
| 2005/0202429 A1 | 9/2005 | Trau et al. |
| 2005/0208503 A1 | 9/2005 | Yowanto et al. |
| 2005/0221340 A1 | 10/2005 | Evans |
| 2005/0227235 A1 | 10/2005 | Carr et al. |
| 2005/0227316 A1* | 10/2005 | Santi et al. ......... C12N 15/1058 435/193 |
| 2005/0255477 A1 | 11/2005 | Carr et al. |
| 2005/0287585 A1 | 12/2005 | Oleinikov |
| 2006/0003347 A1 | 1/2006 | Griffiths et al. |
| 2006/0008833 A1 | 1/2006 | Jacobson |
| 2006/0014146 A1 | 1/2006 | Sucaille et al. |
| 2006/0035218 A1 | 2/2006 | Oleinikov |
| 2006/0040297 A1 | 2/2006 | Leamon et al. |
| 2006/0054503 A1 | 3/2006 | Pamula et al. |
| 2006/0084083 A1* | 4/2006 | Ruan .................... C12Q 1/6809 435/6.14 |
| 2006/0127920 A1 | 6/2006 | Church et al. |
| 2006/0127926 A1 | 6/2006 | Belshaw et al. |
| 2006/0134638 A1 | 6/2006 | Mulligan et al. |
| 2006/0160138 A1 | 7/2006 | Church et al. |
| 2006/0194214 A1 | 8/2006 | Church et al. |
| 2006/0281113 A1 | 12/2006 | Church et al. |
| 2006/0286678 A1 | 12/2006 | Dual et al. |
| 2007/0004041 A1 | 1/2007 | Church et al. |
| 2007/0031857 A1* | 2/2007 | Makarov ................ C12Q 1/686 435/6.1 |
| 2007/0122817 A1 | 5/2007 | Church et al. |
| 2007/0169227 A1 | 7/2007 | Cigan et al. |
| 2007/0231805 A1 | 10/2007 | Baynes et al. |
| 2007/0269870 A1 | 11/2007 | Church et al. |
| 2007/0281309 A1 | 12/2007 | Kong et al. |
| 2008/0003571 A1 | 1/2008 | McKernan et al. |
| 2008/0009420 A1 | 1/2008 | Schroth et al. |
| 2008/0044862 A1 | 2/2008 | Schatz et al. |
| 2008/0064610 A1 | 3/2008 | Lipovsek et al. |
| 2008/0105829 A1 | 5/2008 | Faris et al. |
| 2008/0214408 A1 | 9/2008 | Chatterjee et al. |
| 2008/0261300 A1 | 10/2008 | Santi et al. |
| 2008/0274510 A1 | 11/2008 | Santi et al. |
| 2008/0274513 A1 | 11/2008 | Shenderov et al. |
| 2008/0287320 A1 | 11/2008 | Baynes et al. |
| 2008/0300842 A1 | 12/2008 | Govindarajan et al. |
| 2009/0016932 A1 | 1/2009 | Curcio et al. |
| 2009/0036323 A1 | 2/2009 | van Eijk et al. |
| 2009/0093378 A1 | 4/2009 | Bignell et al. |
| 2009/0878840 | 4/2009 | Baynes et al. |
| 2009/0130718 A1* | 5/2009 | Short .................... C12N 15/102 435/91.2 |
| 2009/0137408 A1 | 5/2009 | Jacobson |
| 2009/0155858 A1* | 6/2009 | Blake .................... C12Q 1/6844 435/91.41 |
| 2009/0181381 A1* | 7/2009 | Oldham ........... G01N 33/54373 435/7.1 |
| 2009/0209430 A1* | 8/2009 | Rasmussen .......... B01J 19/0046 506/17 |
| 2009/0280497 A1 | 11/2009 | Woudenberg et al. |
| 2009/0280697 A1 | 11/2009 | Li et al. |
| 2009/0305233 A1 | 12/2009 | Borovkov et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2010/0028873 A1 | 2/2010 | Belouchi et al. |
| 2010/0028885 A1 | 2/2010 | Balasubramanian et al. |
| 2010/0047876 A1 | 2/2010 | Church |
| 2010/0120098 A1* | 5/2010 | Grunenwald et al. . C12N 15/10 435/193 |

(56) References Cited

U.S. PATENT DOCUMENTS

| | | |
|---|---|---|
| 2010/0124767 A1 | 5/2010 | Oleinikov |
| 2010/0261158 A1 | 10/2010 | Nordman et al. |
| 2010/0273219 A1 | 10/2010 | May et al. |
| 2010/0311058 A1 | 12/2010 | Kim et al. |
| 2011/0105338 A1* | 5/2011 | De Boer ............ C12Q 1/6827 506/2 |
| 2011/0117559 A1 | 5/2011 | Behlke et al. |
| 2011/0117625 A1 | 5/2011 | Lippow et al. |
| 2011/0160078 A1 | 6/2011 | Fodor et al. |
| 2011/0172127 A1 | 7/2011 | Jacobson et al. |
| 2011/0217738 A1 | 9/2011 | Jacobson |
| 2011/0283110 A1 | 11/2011 | Dapkus et al. |
| 2011/0287490 A1 | 11/2011 | Coope et al. |
| 2012/0028843 A1 | 2/2012 | Ramu et al. |
| 2012/0115756 A1 | 5/2012 | Williams et al. |
| 2012/0185965 A1 | 7/2012 | Senger et al. |
| 2012/0220497 A1 | 8/2012 | Jacobson et al. |
| 2012/0270750 A1 | 10/2012 | Oleinikov |
| 2012/0270754 A1 | 10/2012 | Blake |
| 2012/0283110 A1 | 11/2012 | Shendure et al. |
| 2012/0283140 A1 | 11/2012 | Chu |
| 2012/0315670 A1 | 12/2012 | Jacobson et al. |
| 2012/0322681 A1 | 12/2012 | Kung et al. |
| 2013/0005582 A1 | 1/2013 | Lower |
| 2013/0017977 A1 | 1/2013 | Oleinikov |
| 2013/0059296 A1 | 3/2013 | Jacobson et al. |
| 2013/0059344 A1 | 3/2013 | Striedner et al. |
| 2013/0059761 A1 | 3/2013 | Jacobson et al. |
| 2013/0085083 A1 | 4/2013 | Kamberov et al. |
| 2013/0130347 A1 | 5/2013 | Delisa et al. |
| 2013/0163263 A1 | 6/2013 | Jacobson et al. |
| 2013/0196373 A1 | 8/2013 | Gregory et al. |
| 2013/0224729 A1 | 8/2013 | Church et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0274135 A1 | 10/2013 | Zhang et al. |
| 2013/0281308 A1 | 10/2013 | Kung et al. |
| 2013/0296192 A1 | 11/2013 | Jacobson |
| 2013/0296194 A1 | 11/2013 | Jacobson |
| 2013/0309725 A1 | 11/2013 | Jacobson |
| 2014/0141982 A1 | 5/2014 | Jacobson et al. |
| 2014/0295556 A1 | 10/2014 | Joung et al. |
| 2014/0309119 A1 | 10/2014 | Jacobson et al. |
| 2015/0031089 A1 | 1/2015 | Lindstrom |
| 2015/0045234 A1 | 2/2015 | Stone et al. |
| 2015/0065393 A1 | 3/2015 | Jacobson |
| 2015/0191719 A1 | 7/2015 | Hudson et al. |
| 2015/0203839 A1 | 7/2015 | Jacobson et al. |
| 2015/0315547 A1 | 11/2015 | Oberg |
| 2015/0361420 A1 | 12/2015 | Hudson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0097051 A1 | 4/2016 | Jacobson et al. |
| 2016/0122755 A1 | 5/2016 | Hall et al. |
| 2016/0144332 A1 | 5/2016 | Chu |
| 2016/0144333 A1 | 5/2016 | Jacobson et al. |
| 2016/0168564 A1 | 6/2016 | Jacobson et al. |
| 2016/0215381 A1 | 7/2016 | Levine et al. |
| 2016/0250613 A1 | 9/2016 | Jacobson et al. |
| 2016/0326520 A1 | 11/2016 | Ramu et al. |
| 2017/0137858 A1 | 5/2017 | Carr et al. |
| 2017/0175110 A1 | 6/2017 | Jacobson et al. |
| 2017/0198268 A1 | 7/2017 | Jacobson et al. |
| 2017/0349925 A1 | 12/2017 | Jacobson et al. |
| 2018/0023120 A1 | 1/2018 | Kung et al. |
| 2018/0355353 A1 | 12/2018 | Saaem |
| 2019/0010530 A1 | 1/2019 | Saaem |

FOREIGN PATENT DOCUMENTS

| | | |
|---|---|---|
| CN | 1468313 A | 1/2004 |
| CN | 101921840 A | 12/2010 |
| DE | 4343591 A1 | 6/1995 |
| EP | 259160 | 3/1988 |
| EP | 1015576 A1 | 7/2000 |
| EP | 1159285 A1 | 12/2001 |
| EP | 1180548 A2 | 2/2002 |
| EP | 1205548 A1 | 5/2002 |
| EP | 1314783 A1 | 5/2003 |
| EP | 1411122 A1 | 4/2004 |
| EP | 2017356 A2 | 1/2009 |
| EP | 2175021 A2 | 4/2010 |
| EP | 2748318 B1 | 11/2015 |
| JP | 2005-538725 A | 12/2005 |
| JP | 2007-533308 A | 11/2007 |
| JP | 2008-523786 A | 7/2008 |
| KR | 100491810 B1 | 10/2005 |
| WO | WO 1990/000626 A1 | 1/1990 |
| WO | WO 1992/015694 A1 | 9/1992 |
| WO | WO 1993/017126 A1 | 9/1993 |
| WO | WO 1993/020092 A1 | 10/1993 |
| WO | WO 1994/018226 A1 | 8/1994 |
| WO | WO 1995/017413 A1 | 6/1995 |
| WO | WO 1996/033207 A1 | 10/1996 |
| WO | WO 1996/034112 A1 | 10/1996 |
| WO | WO 1997/035957 A1 | 10/1997 |
| WO | WO 1998/005765 A1 | 2/1998 |
| WO | WO 1998/020020 A2 | 5/1998 |
| WO | WO 1998/038299 A1 | 9/1998 |
| WO | WO 1998/038326 A1 | 9/1998 |
| WO | WO 1999/014318 A1 | 3/1999 |
| WO | WO 1999/019341 A1 | 4/1999 |
| WO | WO 1999/025724 A2 | 5/1999 |
| WO | WO 1999/042813 A1 | 8/1999 |
| WO | WO 1999/047536 A2 | 9/1999 |
| WO | WO 2000/029616 A1 | 5/2000 |
| WO | WO 2000/040715 A2 | 7/2000 |
| WO | WO 2000/046386 A2 | 8/2000 |
| WO | WO 2000/049142 A1 | 8/2000 |
| WO | WO 2000/053617 A1 | 9/2000 |
| WO | WO 2000/075368 A2 | 12/2000 |
| WO | WO 2001/081568 A1 | 11/2001 |
| WO | WO 2001/085075 A1 | 11/2001 |
| WO | WO 2001/088173 A2 | 11/2001 |
| WO | WO 2002/004597 A2 | 1/2002 |
| WO | WO 2002/024597 A2 | 3/2002 |
| WO | WO 2002/081490 A2 | 10/2002 |
| WO | WO 2002/095073 A1 | 11/2002 |
| WO | WO 2002/101004 A2 | 12/2002 |
| WO | WO 2003/010311 A2 | 2/2003 |
| WO | WO 2003/033718 A1 | 4/2003 |
| WO | WO 2003/040410 A1 | 5/2003 |
| WO | WO 2003/044193 A2 | 5/2003 |
| WO | WO 2003/046223 A1 | 6/2003 |
| WO | WO 2003/054232 A2 | 7/2003 |
| WO | WO 2003/060084 A2 | 7/2003 |
| WO | WO 2003/064026 A1 | 8/2003 |
| WO | WO 2003/064027 A2 | 8/2003 |
| WO | WO 2003/064611 A2 | 8/2003 |
| WO | WO 2003/064699 A2 | 8/2003 |
| WO | WO 2003/065038 A2 | 8/2003 |
| WO | WO 2003/066212 A2 | 8/2003 |
| WO | WO 2003/083604 A2 | 10/2003 |
| WO | WO 2003/085094 A2 | 10/2003 |
| WO | WO 2003/089605 A2 | 10/2003 |
| WO | WO 2003/100012 A2 | 12/2003 |
| WO | WO 2004/002627 A2 | 1/2004 |
| WO | WO 2004/024886 | 3/2004 |
| WO | WO 2004/029586 A1 | 4/2004 |
| WO | WO 2004/031351 A2 | 4/2004 |
| WO | WO 2004/031399 A2 | 4/2004 |
| WO | WO 2004/034028 A2 | 4/2004 |
| WO | WO 2004/090170 A1 | 10/2004 |
| WO | WO 2005/059096 A2 | 6/2005 |
| WO | WO 2005/071077 A1 | 8/2005 |
| WO | WO 2005/089110 A2 | 9/2005 |
| WO | WO 2005/103279 A2 | 11/2005 |
| WO | WO 2005/107939 A1 | 11/2005 |
| WO | WO 2005/123956 A2 | 12/2005 |
| WO | WO 2006/031745 A2 | 3/2006 |
| WO | WO 2006/044956 A1 | 4/2006 |

(56) References Cited

FOREIGN PATENT DOCUMENTS

| | | |
|---|---|---|
| WO | WO 2006/049843 A1 | 5/2006 |
| WO | WO 2006/076679 A1 | 7/2006 |
| WO | WO 2006/086209 A2 | 8/2006 |
| WO | WO 2006/127423 A2 | 11/2006 |
| WO | WO 2007/008951 A1 | 1/2007 |
| WO | WO 2007/009082 A1 | 1/2007 |
| WO | WO 2007/010252 A1 | 1/2007 |
| WO | WO 2007/075438 A2 | 7/2007 |
| WO | WO 2007/087347 A2 | 8/2007 |
| WO | WO 2007/113688 A2 | 10/2007 |
| WO | WO 2007/117396 A1 | 10/2007 |
| WO | WO 2007/120624 A2 | 10/2007 |
| WO | WO 2007/123742 A2 | 11/2007 |
| WO | WO 2007/136736 A2 | 11/2007 |
| WO | WO 2007/136833 A2 | 11/2007 |
| WO | WO 2007/136834 A2 | 11/2007 |
| WO | WO 2007/136835 A2 | 11/2007 |
| WO | WO 2007/136840 A2 | 11/2007 |
| WO | WO 2008/024319 A2 | 2/2008 |
| WO | WO 2008/027558 A2 | 3/2008 |
| WO | WO 2008/041002 A2 | 4/2008 |
| WO | WO 2008/045380 A2 | 4/2008 |
| WO | WO 2008/054543 A2 | 5/2008 |
| WO | WO 2008/076368 A2 | 6/2008 |
| WO | WO 2008/109176 A2 | 9/2008 |
| WO | WO 2008/130629 A2 | 10/2008 |
| WO | WO 2010/025310 A2 | 3/2010 |
| WO | WO 2010/070295 A1 | 6/2010 |
| WO | WO 2010/025310 A3 | 7/2010 |
| WO | WO 2010/115100 A1 | 10/2010 |
| WO | WO 2010/115154 A1 | 10/2010 |
| WO | WO 2011/056872 A2 | 5/2011 |
| WO | WO 2011/066185 A1 | 6/2011 |
| WO | WO 2011/066186 A1 | 6/2011 |
| WO | WO 2011/085075 A2 | 7/2011 |
| WO | WO 2011/143556 A1 | 11/2011 |
| WO | WO 2011/150168 A1 | 12/2011 |
| WO | WO 2011/161413 A2 | 12/2011 |
| WO | WO 2012/064975 A1 | 5/2012 |
| WO | WO 2012/078312 A2 | 6/2012 |
| WO | WO 2012/084923 A1 | 6/2012 |
| WO | WO 2012/174337 A1 | 12/2012 |
| WO | WO 2013/032850 A2 | 3/2013 |
| WO | WO 2013/163263 A2 | 10/2013 |
| WO | WO 2014/004393 A1 | 1/2014 |
| WO | WO 2014/089290 A1 | 6/2014 |
| WO | WO 2014/093694 A1 | 6/2014 |
| WO | WO 2014/144288 A1 | 9/2014 |
| WO | WO 2014/151696 A1 | 9/2014 |
| WO | WO 2014/160004 A1 | 10/2014 |
| WO | WO 2014/160059 A1 | 10/2014 |
| WO | WO 2014/191518 A1 | 12/2014 |
| WO | WO 2015/017527 A2 | 2/2015 |
| WO | WO 2015/035162 A2 | 3/2015 |
| WO | WO 2015/081114 A2 | 6/2015 |

OTHER PUBLICATIONS

Third Party Observation under Article 115 EPC for EP publication No. 2864531, filed May 18, 2018.
[No Author Listed], "Algae," Wikipedia.com (accessed Mar. 4, 2016).
[No Author Listed], "Archaea," Wikipedia.com (accessed May 11, 2016).
[No Author Listed], "Fish," (Wikipedia.com (accessed Nov. 2, 2014).
[No Author Listed], "Fungi," Wikipedia.com (accessed Jun. 3, 2013).
[No Author Listed], "How many species of bacteria are there," Wisegeek.com (accessed Jan. 21, 2014).
[No Author Listed], "List of sequenced bacterial genomes," Wikipedia.com (accessed Jan. 24, 2014).
[No Author Listed], ""Mammal,"" Wikipedia.com (accessed Sep. 22, 2011).
[No Author Listed], "Murinae," Wikipedia.com (accessed Mar. 18, 2013).
[No Author Listed], "Plant," Wikipedia.com (accessed Aug. 28, 2015).
[No Author Listed], "Protozoa," Wikipedia.com (accessed May 11, 2016).
[No Author Listed], "Viruses," Wikipedia.com (accessed Nov. 24, 2012).
[No Author Listed], Restriction Enzymes. Sigma Aldrich. 2019. https://www.sigmaaldrich.com/china-mainland/zh/technical-documents/articles/biology/restrictionenzymes. 4 pages.
[No Author Listed], TnT® coupled reticulocyte lysate system, Technical Bulletin (Promega, Madison, Wis), 2013.
Abremski et al. Studies on the properties of P 1 site-specific recombination: evidence for topologically unlinked products following recombination. Cell 32:1301-1311 (1983).
Abremski K. et al. Bacteriophage P1 site-specific recombination. Purification and properties of the Cre recombinase protein (1984) J. Mol. Biol. 259: 1509-1514.
Adessi et al., Solid phase DNA amplification: characterisation of primer attachment and amplification mechanisms. Nucleic Acids Research, 28(20):E87, (Oct. 15, 2000).
Afshari et al. Application of Complementary DNA Microarray Technology to Carcinogen Identification, Toxicology, and Drug Safety. Cancer Research, 59, 4759-4760, Oct. 1, 1999.
Aihara, H. et al. A Conformational Switch Controls the DNA Cleavage Activity of .lamda. Integrase, Molecular Cell, 12:187-198, (Jul. 2003).
Akhundova A.A. et al. RNA synthesis on immobilized DNA templates in vitro. Biochemistry—Moscow, 43(5):626-628 (1978).
Altschul et al., Iterated profile searches with PSI-BLAST—a tool for discovery in protein databases, Trends Biochem. Sci., 23:444-447, (Nov. 1998).
Altschul, S., et al. "Basic local alignment search tool," J Mol Biol., 215(3):403-10, (1990).
Andersen, J., et al. "New Unstable Variants of Green Fluorescent Protein for Studies of Transient Gene Expression in Bacteria," Applied and Environmental Microbiology, 64(6):2240-2246 (Jun. 1998).
Ashkin, A., Applications of laser radiation pressure. Science, 210(4474): 1081-1088, (Dec. 5, 1980).
Aslanzadeh, Brief Review: Preventing PCR Amplification Carry-over Contamination in a Clinical Laboratory. Annals of Clinical & Laboratory Science 34(4) :389 (2004).
Au, L., et al. "Gene Synthesis by a LCR-Based Approach: High. cndot.Level Production of Leptin-L54 Using Synthetic Gene in *Escherichia coli*," Biochemical and Biophysical Research Communications, 248:200-203 (1998).
Babineau et al. The FLP Protein of the 2 micron Plasmid of Yeast (1985) J. Biol. Chem. 260: 12313-12319.
Bar G., et al., Dendrimer-modified silicon oxide surfaces as platforms for the deposition of gold and silver colloid monolayers: preparation method, characterization, and correlation between microstructure and optical properties, Langmuir, 12(5): 1172-1179, (Mar. 6, 1996).
Bartsevich, V., et al. "Engineered Zinc Finger Proteins for Controlling Stem Cell Fate," Stem Cells, 21:632-637 (2003).
Beer et al., On-chip, real time single-copy polymerase chain reaction in picoliter droplets, Analytical Chemistry, 79(22):8471-8475, (Nov. 15, 2007).
Begley, Psst, the human genome was never completely sequenced. Stat News. Jun. 20, 2017. 8 pages.
Beier et al., Analysis of DNA-microarray produced by inverse in situ oligonucleotide synthesis. J. Biotechnology, 94:15-22 (2002).
Bennett, Solexa Ltd., Pharmacogenomics, 5(4):433-8, (Jun. 2004).
Berlin Y. A. DNA splicing by directed ligation (SDL), Current Issues Molec. Biol. 1:21-30, 1999.
Bethell, D., et al. From monolayers to nanostructured materials: an organic chemist's view of self-assembly, J. Electroanal. Chem., 409:137-143, (1996).
Binkowski et al. Correcting erros in synthetic DNA through consensus shuffling Nucl. Acids Res., vol. 33, No. 6, e55, 2005.

(56) References Cited

OTHER PUBLICATIONS

Blanchard, Alan P., "Synthetic DNA Arrays in Genetic Engineering," Plenum Press. 20: 111-123 (1998).
Boal et al. Cleavage of oligodeoxyribonucleotides from controlled-pore glass supports and their rapid deprotection by gaseous amines, NAR, 24(15):3115-3117, (1996).
Boltner, D., et al. "R391: A Conjugative Integrating Mosaic Comprised of Phage, Plasmid, and Transposon Elements," J. of Bacteriology, 184(18):5158-5169 (Sep. 2002).
Booth, P., et al. "Assembly and cloning of coding sequences for neurotrophic factors directly from genomic DNA using polymerase chain reaction and uracil DNA glycosylase," Gene, 146(2):303-308 (1994).
Braatsch et al., Escherichia coli strains with promoter libraries constructed by Red/ET recombination pave the way for transcriptional fine-tuning, Biotechniques. 2008;45(3):335-337.
Brown, Chappell "BioBricks to help reverse-engineer life," URL: https://www.edn.com/biobricks-to-help-reverse-engineer-life/ (2004).
Burge et al., Prediction of complete gene structures in human genomic DNA, J Mol Biol., 268(1):78-94, (1997).
Cai, Q., et al. "Immunogenicity of Polyepitope Libraries Assembled by Epitope Shuffling: An Approach to the Development of Chimeric Gene Vaccination Against Malaria," Vaccine, 23:267-277, (2004).
Carr, P., et al. Protein-mediated error-correction for de novo DNA synthesis. Nucleic Acids Research, 32(20), e162 (9 pages), (2004).
Caruthers et al., "CXV. Total synthesis of the structural gene for an alanine transfer RNA from yeast. Enzymic joining to form the total DNA duplex," J Mol Biol., 72(2):475-92, (Dec. 28, 1972).
Cassell et al., Mechanism of Inhibition of Site-specific Recombination by the Holliday Junction-trapping Peptide WKHYNY: Insights into Phage I integrase-mediated Strand Exchange. J. Mol. Biol., 327:413-429, (2003).
Chakrabarti et al., Novel Sulfoxides facilitate GC-rich template amplification., 2002, BioTechniques 32(4):866-873.
Chalmers, F.P., et al. Scaling up the Ligase Chain Reaction-Based Approach to Gene Synthesis. BioTechniques 30:249-252 (2001).
Chan, L. et al. "Refactoring bacteriophage T7," Molecular Systems Biol., doi: 10.1038/msb4100025, (Published online Sep. 13, 2005).
Chandrasegaran, S., et al. "Chimeric Restriction Enzymes: What is Next?" Biol. Chern., 380:841-848 (1999).
Chang, C., et al. Evolution of a cytokine using DNA family shuffling, NatureBiotechnology, 17: 793-797(1999).
Che, A. "BioBricks++: Simplifying Assembly of Standard DNA Components," [Online] XP002412778, URL:http://austinche.name/docs/bbpp.pdf (Jun. 9, 2004).
Chen et al., Restriction Enzymes. Genetic Engineering. 1983. 4:67-75.
Chen, H.B., et al. "A new method for the synthesis of a structural gene," Nucleic Acids Research 18(4):871-878 (1990).
Cherepanov A "Joining of short DNA oligonucleotides with base pair mismatches by T4 DNA ligase" J Biochem; ;129(1):61-8, (Jan. 2001).
Chetverin et al., Sequencing pool of Nucleic Acids on Oligonucleotide arrays, Biosystems, 30:215-231, (1993).
Chevalier, B., et al. "Design, Activity, and Structure of a Highly Specific Artificial Endonuclease," Molecular Cell, 10:895-905 (2002).
Chevalier, B., et al. "Homing endonucleases: structural and functional insight into the catalysts of intron/intein mobility", Nucl. Acids Res., 29(18):3757-3774 (2001).
Cho et al. Creating, transporting, cutting and merging liquid droplets by electrowetting-based actuation for digital microfluidic circuits, J. of Microelectromechanical Systems, 12(1):70-80, (Feb. 2003).
Christians, F., et al. Directed evolution of thymidine kinase for AZT phosphorylation using DNA family shuffling, Nature Biotechnology, 17:259-264(1999).
Coco, W., et al. "Growth Factor Engineering by Degenerate Homoduplex Gene Family Recombination," Nature Biotechnology, 20:1246-1250, (Dec. 2002).

Colvin, V., et al. Semiconductor nanocrystals covalently bound to metal surfaces with self-assembled monolayers, J. Am. Chem. Soc., 114(13):5221-5230, 1992.
Crameri, A, et al. DNA shuffling of a family of genes from diverse species accelerates directed evolution, Nature, 391:288-291(1998).
Crameri, A, et al. Molecular evolution of an arsenate detoxification pathway by DNA shuffling, Nature Biotechnology, 15:436-438 (1997).
Crameri, A., et al. Improved Green Fluorescent Protein by Molecular Evolution Using DNA Shuffling. Nature Biotechnology, 14:315-319, (Mar. 1996).
Cui T. et al. Sepharose-supported DNA as template for RNA synthesis J. Biotechnology, 66: 225-228 (1998).
Dafhnis-Calas, F., et al. Iterative in vivo assembly of large and complex transgenes by combining the activities of <DC31 integrase and Cre recombinase, Nucleic AcidsResearch, 33(22): 1-14 (2005).
Datsenko K.A. et al. One-step inactivation of chromosomal genes in Escherichia coli K-12 using PCR products PNAS (2000) 97: 6640-6645.
Dedkova, L. et al. Enhanced D-Amino Acid Incorporation into Protein by modified Ribosomes. J. Am. Chem. Soc., 125:6616-6617, (2003).
Demeler et al. Neural network optimization for E. colipromoter prediction. Nucl. Acids. Res. 19:1593-1599 (1991).
Dillon, P.J. et al., A Rapid Method for the Construction of Synthetic Genes Using the Polymerase Chain Reaction, Biotechniques, vol. 9, No. 3, pp. 298-300, 1990.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Duggan et al., "Expression profiling using cDNA microarrays" Nature Genetics, 21: 10-14, 1999.
Ellson, Picoliter: Enabling Precise Transfer of Nanoliter and Picoliter Volumes. Drug Discovery Today 7(5 Suppl.):s32 (2002).
Elowitz et al., A synthetic oscillatory network of transcriptional regulators. Nature. 2000;403;335-338.
Engler C. et al. "A one pot, one step, precision cloning method with high throughput capability" PLoS One, 3:e3647, 2008.
Engler C. et al. Golden Gate Shuffling: a one-pot DNA shuffling method based on type IIS restriction enzymes PLoS One, 4:e5553, 2009.
Evans et al., Roles for Mismatch Repair Factors in Regulating Genetic Recombination, Molecular & Cellular Biology, 20(21):7839-7844 (Nov. 2000).
Ferretti, L. et al. "Total synthesis of a gene for bovine rhodopsin," PNAS, 83:599-603 (Feb. 1986).
Ferrin, L.J., et al. Sequence-specific ligation of DNA using RecA protein, Proc. Natl. Acad. Sci. USA, 95: 2152-2157 (1998).
Fidalgo et al., Surface induced droplet fusion in microfluidic devices, Lab on Chip, 7(8)984-986, (2007).
Fisch, I. et al. A Strategy of Exon Shuffling for Making Large Peptide Repertoires Displayed on Filamentous Bacteriophage. Proceedings of the National Academy of Sciences of USA, 93:7761-7766, (Jul. 1996).
Flanagan et al. Analysis of inhibitors of the site-specific recombination reaction mediated by Tn3 resolvase (1989) J. Mol. Biol. 206: 295-304.
Fleck et al., DNA Repair, J. Cell Science, 117(4):515-517 (2004).
Fodor et al. (1991) Science 251:767.
Forster et al., A human gut bacterial genome and culture collection for improved metagenomic analyses. Nat Biotechnol. 2019;37(2):186?192. doi:10.1038/s41587-018-0009-7.
Fujita et al., Surprising liability of biotin-streptavidin bond during transcription of biotinylated DNA bound to paramagnetic streptavidin beads. Bio Techniques, 14:608-617 (1993).
Fullwood et al., Next-generation DNA sequencing of paired-end tags (PET) for transcriptome and genome analyses. Genome Res. Apr. 2009;19(4):521-32. doi: 10.1101/gr.074906.107.
Gabsalilow et al., Site- and strand-specific nicking of DNA by fusion proteins derived from MutH and I-SceI or TALE repeats. Nucleic Acids Res. Apr. 2013;41(7):e83. doi: 10.1093/nar/gkt080. Epub Feb. 13, 2013.

(56) References Cited

OTHER PUBLICATIONS

Gao, X. et al. Thermodynamically balanced inside-out (TBIO) PCR-based gene synthesis: a novel method of primer design for high fidelity assembly of longer gene sequences. Nucleic Acids Research, 31(22):e143 (11 pages) (2003).

Gardner, T., et al. Construction of a genetic toggle switch in *Escherichia coli*. Nature, 403(20):339-342 (Jan. 2000).

Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.

Gibbs, W. "Synthetic Life," Scientific American, [Online] URL: htto://www.sciam.com/orintversion.cfm?articleiD=0009FCA4, (Apr. 26, 2004).

Glasgow A.C. et al. DNA-binding properties of the Hin recombinase (1989) J. Biol. Chem. 264: 10072-10082.

Goler, J. BioJADE: A Design and Simulation Tool for Synthetic Biological Systems. MIT Computer Science and Artificial Intelligence Laboratory, AI Technical Report, [Online] URL:http://dspace.mit.edu/bitstream/1721.1/30475/2/MIT-CSAIL-TR-2004-036.pdf, (May 2004).

Grabar, K., et al., Preparation and Characterization Monolayers, Anal. Chem., 67:735-743, (1995).

Greenberg et al., Cleavage of oligonucleotides from solid-phase support using o-nitrobenzyl photochemistry, J. of Org. Chem., 59(4):746-753, (Feb. 1994).

Griffith et al., Coordinating Multiple Droplets in Planar Array Digital Microfluidic Systems, The International Journal of Robotics Research, 24(11):933-949, (Nov. 2005).

Gronostajski et al., The FLP protein of the 2 micron plasmid of yeast (1985) J. Biol. Chem. 260: 12328-12335.

Guilinger et al., Fusion of catalytically inactive Cas9 to FokI nuclease improves the specificity of genome modification. Nat Biotechnol. Jun. 2014;32(6):577-582. doi: 10.1038/nbt.2909. Epub Apr. 25, 2014.

Gulati et al. Opportunities for microfluidic technologies in synthetic biology. Journal of the Royal Society, vol. 6, Suppl. 4, pp. S493-S506, (2009).

Guntas, G., et al. A molecular switch created by in vitro recombination of nonhomologous genes. Chem. & Biol., 11:1483-1487 (Nov. 2004).

Guntas, G., et al. Directed Evolution of Protein Switches and Their Application to the Creation of Ligand-Binding Proteins. Proc. Natl. Acad. Sci. USA, 102(32):11224-11229 (Aug. 9, 2005).

Gupta, N., et al. Studies on Polynucleotides, LXXXVIII. Enzymatic Joining of Chemically Synthesized Segments Corresponding to the Gene for Alanine-tRNA. PNAS, 60:1338-1344, (1968).

Hacia J.G. et al. Applications of DNA chips for genomic analysis. Mol Psychiatry. Nov. 1998;3(6):483-92.

Hacia J.G. Resequencing and mutational analysis using oligonucleotide microarrays, Nature Genetics, 21(1 suppl):42-47, 1999.

Haeberle et al., Microfluidic platforms for lab-on-chip applications, Lab on a Chip 7(9):1094-1110, (2007).

Haffter et al. Enhancer independent mutants of the Cin recombinase have a relaxed topological specificity. (1988) EMBO J. 7:3991-3996.

Hansen et al., Review of Mammalian DNA Repair and Transcriptional Implications, J. Pharmacol. & Exper. Therapeutics, 295(1):1-9, (2000).

Hardy et al., Reagents for the preparation of two oligonucleotides per synthesis (TOPSTM), Nucleic Acids Research, 22(15):2998-3004, (1994).

Hawley et al., Compilation and analysis of *Escherichia coli* promoter DNA sequences Nucl. Acid. Res. 11:2237-2255. 1983.

Hayden et al., Gene synthesis by serial cloning of oligonucleotides. DNA. Oct. 1988;7(8):571-7.

Hecker, K. "Error Analysis of Chemically Synthesized Polynucleotides," BioTechniques, 24(2):256-260, (Feb. 1998).

Heeb, S., et al. Small, Stable Shuttle Vectors Based on the Minimal pVS1 Replicon for use in Gram-Negative Plant-Associated Bacteria. MPMI, 13(2):232-237 (2000).

Henegariu et al. "Multiplex PCR: critical parameters and step-by-step protocol" Biotechniques, 23(3): 504-511, (Sep. 1997).

Hermeling, S., et al. Structure-Immunogenicity Relationships of Therapeutic Proteins. Pharmaceutical Research, 21(6):897-903, (Jun. 2004).

Higuchi, R., et al. A general method of in vitro preparation and specific mutagenesis of DNA fragments: study of protein and DNA interactions. Nucleic Acids Research, 16(15):7351-7367 (1988).

Hoess et al., Mechanism of strand cleavage and exchange in the Cre-lox site-specific recombination system (1985) J. Mol. Biol. 181: 351-362.

Hoess R.H. et al. Interaction of the bacteriophage P 1 recombinase Cre with the recombining site loxP (1984) Proc. Natl. Acad. Sci. USA 81: 1026-1029.

Hoess R.H. et al. P 1 site-specific recombination: nucleotide sequence of the recombining sites (1982) Proc. Natl. Acad. Sci. USA 79: 3398-3402.

Hoess R.H. et al. The role of the loxP spacer region in PI site-specific recombination (1986), Nucleic Acids Res. 14: 2287-2300.

Holmes, Model studies for new o-nitrobenzyl photolabile linkers: substituent effects on the rates of photochemical cleavage, J. of Org. Chem., 62(8):2370-2380, (Apr. 18, 1997).

Hoover et al., DNAWorks: an automated method for designing oligonucleotides for PCR-based gene synthesis, Nucleic Acids Research, 30(10):e43 (7 pages), (2002).

Horton, R., et al. "Engineering hybrid genes without the use of restriction enzymes: Gene splicing by overlap extension," Gene, 77:61-68, (1989).

Hyman, A new method of sequencing DNA, Analytical Biochemistry, 174(2):423-436, (Nov. 1, 1988).

Ibrahim, E., et al. "Serine/arginine-rich protein-dependent suppression of exon skipping by exonic splicing enhancers," Proc. Natl. Acad. Sci. U S A, 102(14):5002-5007, (Apr. 5, 2005).

Ito R. et al. "Novel muteins of human tumor necrosis factor alpha" Biochimica et Biophysica Acta, 1096 (3): 245-252 (1991).

Jayaraman K. et al. "Polymerase chain reaction-mediated gene synthesis: Synthesis of a gene coding for isozyme c of horseradish peroxidase" P.N.A.S. 88: 4084-4088, 1991.

Jayaraman et al. "A PCR-mediated Gene synthesis strategy involving the assembly of oligonucleotides representing only one of the strands," Biotechniques, 12(3):392-398, (1992).

Jensen P.R. et al. The sequence of spacers between the consensus sequences modulates the strength of prokaryotic promoters Appl. Env. Microbiol. 64:82-87, 1998.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Johnston M. Gene chips: Array of hope for understanding gene regulation. Current Biology, 8: (5) R171, 1998.

Jones, T.D., et al. "The Development of a Modified Human IFN-alpha2b Linked to the Fc Portion of Human IgG1 as a Novel Potential Therapeutic for the Treatment of Hepatitis C Virus Infection," Journal of Interferon & Cytokine Research, 24:560-572,(2004).

Kahl et al. Solution-Phase Bioconjugate Synthesis Using Protected Oligonucleotides Containing 3'-Alkyl Carboxylic Acids, J. of Org. Chem., 1999;64(2):507-510.

Kahl et al., High-Yielding Method for On-Column Derivatization of Protected Oligodeoxy-nucleotides and its Application to the Convergent Synthesis of 5',3'-Bis-conjugates, J. of Org. Chem., 63(15):4870-4871 (1998).

Kampke et al., Efficient primer design algorithms. Bioinformatics, 2001;17(3):214-225.

Kelly et al., Miniaturizing chemistry and biology in microdroplets, Chem. Commun., 1773-1788, (2007).

Khaitovich, P., et al. "Characterization of functionally active subribosomal particles from Thermus aquaticus," Proc. Natl. Acad. Sci., 96:85-90 (Jan. 1999).

(56) References Cited

OTHER PUBLICATIONS

Kim et al., Precision genome engineering with programmable DNA-nicking enzymes. Genome Res. Jul. 2012;22(7):1327-33. doi:10.1101/gr.138792.112. Epub Apr. 20, 2012.
Kim J.H. et al. "Solid-phase genetic engineering with DNA immobilized on a gold surface." J. Biotechnology, 96:213-22 (2002).
Kim, C., et al. Biological lithography: Improvements in DNA synthesis methods, J. Vac. Sci. Technol. B 22(6):3163-3167 (2004).
Kim, Y., et al. Insertion and Deletion Mutants of FokI Restriction Endonuclease, J. Biol. Chem., 269(50):31978-31982 (1994).
Kinde et al., Detection and quantification of rare mutations with massively parallel sequencing. Proc Natl Acad Sci U S A. Jun. 7, 2011;108(23):9530-5. doi: 10.1073/pnas.1105422108. Epub May 17, 2011. Supplemental Information.
Kisselev, L., et al. "Termination of translation: interplay of mRNA, rRNAS and release factors?," The EMBO J., 22(2):175-182, (2003).
Kitamura, K., et al. "Construction of Block-Shuffled Libraries of DNA for Evolutionary Protein Engineering: Y-Ligation-Based Block Shuffling." Protein Engineering, 15(10): 843-853, (Oct. 2002).
Kleppe K., et al. "Studies of polynucleotides: repair replication of short synthetic DNA's as catalyzed by DNA polymerases," J. Mol. Biol. 56:341-361, (1971).
Kodumal et al., "Total synthesis of long DNA sequences: Synthesis of a contiguous 32-kb polyketide synthase gene cluster," PNAS, 101(44):15573-15578, (Nov. 2, 2004).—15578.
Kolisnychenko, V., et al. "Engineering a Reduced *Escherichia coli* Genome," Genome Research, 12:640-647, (2002).
Kong et al., Parallel gene synthesis in microfluidic device, Nucleic Acids Research, vol. 35, No. 8, pp. e61-1 (9 pages), (2007).
Kosuri et al., Scalable gene synthesis by selective amplification of DNA pools from high-fidelity microchips. Nat Biotechnol. Dec. 2010;28(12):1295-9. doi: 10.1038/nbt.1716. Epub Nov. 28, 2010.
Kotsopoulou, E., et al. "A Rev-Independent Human Immunodeficiency Virus Type 1 (HIV-1)-Based Vector That Exploits a Codon-Optimized HIV-1 gag-pol Gene," Journal of Virology, 74(10):4839-4852, (May 2000).
Kowalczykowski, S. "In vitro reconstitution of homologous recombination reactions," Experientia, 50:204-215, (1994).
Kowalczykowski, S. "Initiation of genetic recombination and recombination-dependent replication," TIBS, 25:156-165, (Apr. 2000).
Krieg et al., Real-time detection of nucleotide incorporation during complementary DNA strand analysis Chem. Bio. Chem. 4:589-592 (2003).
Kurian et al. DNA chip technology. J Pathol.; 187(3):267-71, (Feb. 1999).
Lamers, M., et al. "ATP Increases the Affinity between MutS ATPase Domains," J. Biol. Chem., 279(42):43879-43885, (Oct. 15, 2004).
Lashkari et al. "An automated multiplex oligonucleotide synthesizer: Development of high throughpout, low cost DNA synthesis". PNAS 92(17): 7912-7915, (1995).
Leamon et al., A massively parallel PicoTiterPlate™ based platform for discrete pico-liter scale polymerase chain reactions, Electrophoresis, 24(21):3769-3777, (Nov. 2003).
Lebedenko E.N. et al. Method of artificial DNA splicing by directed ligation Nucleic Acids Research, 19: 6757-6761, 1991.
Lederman et al., DNA-directed peptide synthesis. 1. A comparison of T2 and *Escherichi coli* DNA-directed peptide synthesis in two cell-free systems. Biochim Biophys Acta. Nov. 21, 1967;149(1):253-8.
Lee, K., et al. "Genetic approaches to Studying Protein Synthesis: Effects of Mutations at .psi.1516 and A535 in *Escherichia coli* 16S rRNA," J. Nutr., 131:2994S-3004S, (2001).
Leslie et al., Site-specific recombination in the replication terminus region of *Escherichia coli*: functional replacement of dif. (1995) EMBO J. 14: 1561-1570.
Lewis et al. Gene modification via plug and socket gene targeting. J Clin Invest. Jan. 1, 1996;97(1):3-5.
Lewis et al., Control of directionality in integrase-mediated recombination: examination of recombination directionality factors (RDFs) including Xis and Cox proteins, Nucl. Acids Res., 29(11):2205-2216 (2001).
Li et al., Alteration of the cleavage distance of Fok I restriction endonuclease by insertion mutagenesis. Proc Natl Acad Sci U S A, 90:2764-2768, (Apr. 1993).
Li, C., and Evans, R. "Ligation independent cloning irrespective of restriction site compatibility," Nucl. Acids Res., 25(20):4165-4166 (1997).
Link, A., et al. "Methods for generating precise deletions and insertions in the genome of wild-type *Escherichia coli*: Application to open reading frame characterization," J. Bacteriol., 179(20):6228-6237, (Oct. 1997).
Liu G. et al. "DNA computing on surfaces." Nature, 403:175179 (2000).
Liu, W. et al. "Genetic Incorporation of Unnatural Amino Acids Into Proteins in Mammalian Cells," Nature Methods, 4(3):239-244, (Mar. 2007).
Liu, Y., et al., "DNA ligation of ultramicrovolume using EWOD microfluidic system with coplanar electrodes: DNA ligation of ultramicrovolume using a EWOD microfluidic system," J. of Micromechanics and Microengineering, 18(4):45017 (7 pages), (2008).
Lu et al., Conjugative transposition: Tn916 integrase contains two independent DNA binding domains that recognize different DNA sequences '(1994) EMBO J. 13: 1541-1548.
Luo, P., et al. "Development of a Cytokine Analog with Enhanced Stability Using Computational Ultrahigh Throughput Screening," Protein Science, 11:1218-1226, (2002).
Lutz, S., et al. "Homology-Independent Protein Engineering," Current Opinion in Biotechnology, 11(4):319-324, (Aug. 2000).
Mandecki et al. FokI method of gene synthesis Gene, 68:101-107 (1988).
Mandecki W. Oligonucleotide-directed double-strand break repair in plasmids of *Escherichia coli*: A method for site-specific mutagenesis. 1986, PNAS, 83 :7177-7181.
Mannervik, B. "Optimizing the Heterologous Expression of Glutathione Transferase," Methods in Enzymology, 401:254-265, (2005).
Margulies et al., Genome Sequencing in Microfabricated High-Density Picolitre Reactors, Nature. 437: 376-380 (2005). Supplemental materials.
Matzas et al. (High-fidelity gene synthesis by retrieval of sequence-verified DNA identified using high-throughput pyrosequencing, Nature Biotechnology 28, 1291-1294 (2010), Published online Nov. 28, 2010).
McCaughan et al., Single-Molecule Genomics, The Journal of Pathology, 220: 297-306, (Jan. 1, 2009).
McClain et al., "Genome Sequence Analysis of Helicobacter Pylori Strains Associated with Gastric Ulceration and Gastric Cancer," BMC Genomics, Biomed Central Ltd, London, IK. 10(1):3 (2009).
McGall et al., "Light-Directed Synthesis of High-Density Oligonucleotide Arrays Using Semiconductor Photoresists," Pro. Natl. Acad. Sci. 93(24):13555-13560 (1996).
Mei et al., Cell-Free Protein Synthesis in Microfluidic Array Devices, Biotechnol. Prog. 2007, 23:1305-1311.
Mercier. J. et al. Structural and functional characterization of tnpI, a recombinase locus in Tn21 and related beta-lactamase transposons. (1990) J. Bacteriol. 172: 3745.
Metzker et al., Termination of DNA synthesis by novel 3'-modified-deoxyribonucleoside 5'-triphosphates, NAR, 22(20):4259-4267, (1994).
Metzker, Emerging technologies in DNA sequencing. Genome Res. Dec. 2005;15(12):1767-76.
Meyer-Leon et al., Purification of the FLP site-specific recombinase by affinity chromatography and re-examination of basic properties of the system. Nucleic Acids Res. Aug. 25, 1987;15(16):6469-88.
Mezard, C., et al. "Recombination Between Similar but not Identical DNA Sequences During Yeast Transformation Occurs Within Short Stretches of Identity," Cell, 70:659-670, (Aug. 21, 1992).
Miick, S., et al. "Crossover isomer bias is the primary sequence-dependent property of immobilized Holliday junctions," Proc. Natl. Acad. Sci. USA, 94:9080-9084, (Aug. 1997).

(56) References Cited

OTHER PUBLICATIONS

Milton, R., et al. "Total Chemical Synthesis of a D-Enzyme: The Enantiomers ofHIV-1 Protease Show Demonstration of Reciprocal Chiral Substrate Specificity," Science, 256:1445-1448, (Jun. 5, 1992).
Mir K. U. et al. Sequencing by cyclic ligation and cleavage (CycLic) directly on a microarray captured template. Nucl. Acids Rse. vol. 37, No. 1 e5, 2008.
Mitra et al., "Fluorescent in situ Sequencing on Polymerase Colonies," Analytical Biochemistry. 320:55-65 (2003).
Modrich, P. "Strand-specific Mismatch Repair in Mammalian Cells," J. Biol. Chem., 272(40):24727-24730, (Oct. 3, 1997).
Moffitt et. al. "Recent Advances in Optical Tweezers". Annual Review of Biochemistry 77:205 (Feb. 2008).
Moore et al., Computational Challenges in Combinatorial Library Design for Protein Engineering, AIChE Journal, 50(2):262-272, (Feb. 2004).
Morton, Life, Reinvented. Wired. 2009. Retrieved from http://archive.wired.com/wired/archive/13.01/mit_pr.html on Aug. 14, 2015.
Muller, Ten years of gene targeting: targeted mouse mutants, from vector design to phenotype analysis. Mech Dev. Apr. 1999;82(1-2):3-21.
Nakamaye, K., et al. "Direct sequencing of polymerase chain reaction amplified DNA fragments through the incorporation of deoxynucleoside-thiotriphosphates," Nucleic Acids Research, 16(21):9947-9959, (1988).
Nakamura et al., How protein reads the stop codon and terminates translation, Genes to Cells, 3:265-278, (1998).
Nakayama et al., A system using convertible vectors for screening soluble recombinant proteins produced in *Escherichia coli* from randomly fragmented cDNAs, Bioch. and Biophys. Res. Comm., 312:825-830, (2003).
Ness, J., et al. DNA shuffling of subgenomic sequences of subtilisin, Nature Biotechnology 17:893-896 (1999). Abstract only.
Ness, J., et al. "Synthetic Shuffling Expands Functional Protein Diversity by Allowing Amino Acids to Recombine Independently" Nature Biotechnology, 20:1251-1255, (Dec. 2002).
Neuman et al., Optical trapping. Rev Sci Instrum. Sep. 2004;75(9):2787-809.
Nilsson P., et al. "Real-Time monitoring of DNA manipulations using biosensor technology," Analytical Biochemistry, 224:400-408, (1995).
Nilsson, L., et al. "Improved Heterologous Expression of Human Glutathione Transferase A4-4 by Random Silent Mutagenesis of Codons in the 5' Region," Biochemica et Biophysica Acta, 1528: 101-106, (2001).
Noirot et al., DNA Strand Invasion Promoted by *Escherichia coli* RecT Protein, J. Biol. Chem., 273(20):12274-12280, (May 15, 1998).
Novy, R., et al. "Ligation Independent Cloning: Efficient Directional Cloning of PCR Products," Novagen, Inc., InNovations, 5:1-3, (http://www.emdbiosciences.com/html/NVG/inNovations.html), (1996).
Orban P.C. et al. Tissue- and site-specific DNA recombination in transgenic mice (1992) Proc. Natl. Acad. Sci. 89: 6861-6865.
Osawa, S., et al. "Recent Evidence for Evolution of the Genetic Code," Microbiological Reviews, 56(1):229-264, (Mar. 1992).
Osborn et al., When phage, plasmids, and transposons collide: genomic islands, and conjugative and mobilizable-transposons as a mosaic continuum, Plasmid, 48:202-212, (2002).
Pachuk C.J. et al. "Chain reaction cloning: one step method for directional ligation of multiple DNA fragments" Gene, 243(1-2): 19-25 (2000).
Padgett et al. Creating seamless junctions independent of restriction sites in PCR cloning, Gene, Feb. 2, 1996, vol. 168, No. 1, pp. 31-35.
Pan et al., An approach for global scanning of single nucleotide variations, PNAS, 99(14):9346-9351, (Jul. 9, 2002).
Panet et al., Studies of polynucleotides: the linkage of deoxyribopolynucleotides templates to cellulose and its use in their replication. J. Biol. Chem. 249(16):5213-5221 (1974).

Parr et al., New donor vector for generation of histidine-tagged fusion proteins using the Gateway Cloning System, Plasmid, 49:179-183, (2003).
Pemov et al., DNA analysis with multiplex microarray-enhanced PCR. Nucleic Acids Res. Jan. 20, 2005;33(2):e11.
Peters et al., Tn7: Smarter Than we Thought, Nature, 2:806-814, (Nov. 2001).
Petrik et al., "Advances in Transfusion Medicine in the First Decade of the 21.sup.st Century: Advances in Miniaturized Technologies," Transfusion and Apheresis Science. 45(1): 45-51 (2011).
Pon., R. "Solid-phase supports for oligonucleotide synthesis," Methods Mol. Biol., 20:465-496, (1993).
Posfai, G., et al. In vivo excision and amplification of large segments of the *Escherichia coli* genome, Nucl. Acids Res., 22(12):2392-2398, (1994).
Posfai, G., et al. Markerless gene replacement in *Escherichia coli* stimulated by a doublestrand break in the chromosome, Nucl. Acids Res., 27(22):4409-4415, (1999).
Prodromou et al., Recursive PCR: A Novel Technique for Total Gene Synthesis Protein Engineering, 5(8):827-829 (1992).
Ramachandran et al., End-Point Limiting-Dilution Real-Time PCR Assay for Evaluation of Hepatitis C Virus Quasispecies in Serum: Performance Under Optimal and Suboptimal Conditions, Journal of Virological Methods. 151(2): 217-224 (2008).
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Randegger et al., Real-time PCR and melting curve analysis for reliable and rapid detection of SHV extended-spectrum beta-lactamases. Antimicrob Agents Chemother. Jun. 2001;45(6):1730-6.
Regalado, A. "Next Dream for Venter: Create Entire Set of Genes From Scratch," Wall Street Journal, A1, (Jun. 29, 2005).
Reyrat, J., et al. "Counterselectable Markers: Untapped Tools for Bacterial Genetics and Pathogenesis," Infection and Immunity, 66(9):4011-4017, (Sep. 1998).
Richmond, K. E., et al., "Amplification and assembly of chip-eluted DNA (AACED): a method for high-throughput gene synthesis", Nucleic Acids Research, Oxford University Press, Surrey, GB, vol. 32, No. 17, pp. 5011-5018, Jan. 1, 2004.
Roberts et al., RNA-peptide fusions for the in vitro selection of peptides and proteins, Proc Natl Acad Sci USA. 94(23): 12297-302, 1997.
Rouillard, J. et al. "Gen2Oligo: Oligonucleotide design for in vitro gene synthesis," Nucleic Acids Research, 32: W176-W180, (2004).
Rouwendal, G., et al. "Enhanced Expression in Tobacco of the Gene Encoding Green Fluorescent Protein by Modification of its Codon Usage," Plant Molecular Biology, 33:989-999, (1997).
Ryu et al. Recent Progress in Biomolecular Engineering, Biotechnol. Prog. 16:2-16 (2000).
Sa-Ardyen, P., et al. "The flexibility of DNA double crossover molecules," Biophys. J., 84:3829-3837, (Jun. 2003).
Saha et al., The promoter of the Chinese hamster ovary dihydrofolate reductase gene regulates the activity of the local origin and helps define its boundaries. Genes Dev. Feb. 15, 2004;18(4):397-410. Epub Feb. 20, 2004.
Saiki, R., et al. "Analysis of enzymatically amplified beta-globin and HLA-DQ alpha DNA with allele-specific oligonucleotide probes," Nature, 324(6093):163-166, (Nov. 13, 1986).
Sakabe, N., et al. "A Bioinformatics Analysis of Alternative Exon Usage in Human Genes Coding for Extracellular Matrix Proteins," Genetics and Molecular Research, 3(4):532-544, (2004).
Sakamoto, K., et al. "Site-Specific Incorporation of an Unnatural Amino Acid Into Proteins in Mammalian Cells," Nucleic Acids Research, 30(21):4692-4699, (2002).
Saks, M. "Making sense out of nonsense," PNAS, 98(5):2125-2127, (Feb. 27, 2001).
Saks, M., et al. "An Engineered Tetrahymena tRNA.sup.Gln, for in Vivo Incorporation of Unnatural Amino Acids into Proteins by Nonsense Suppression," J. of Biol. Chem., 271(38):23169-23175, (Sep. 20, 1996).

(56) References Cited

OTHER PUBLICATIONS

Salyers, A., et al. "Conjugative Transposons: an Unusual and Diverse Set of Integrated Gene Transfer Elements," Microbiological Reviews, 59(4):579-590, (Dec. 1995).
Sanjana, N. et al., A Transcription activator-like effector toolbox for genome engineering, Nature Protocols, Nature Publishing Group. Jan. 1, 2012;7(1):171-192.
Sato et al. The cisA cistron of Bacillus subtilis sporulation gene spoIVC encodes a protein homologous to a site-specific recombinase (1990) J. Bacteriol. 172: 1092-1098.
Sato, T., et al. "Production of menaquinone (vitamin K2)-7 by Bacillus subtilis," J. of Bioscience and Engineering, 91(1):16-20, (2001).
Sauer, Functional expression of the ere-lox site-specific recombination system in the yeast *Saccharomvces cerevisiae* (1987) Mol. Cell. Biol. 7: 2087-2096.
Schaerli, Y., et al., ContinuoFlow polymerase Chain reaction of single-copy DNA Micorfluidic Microdroplets, Anal. Chem., 81: 302-306, (2009).
Scior, Annike et al., Directed PCR-free engineering of highly repetitive DNA sequences, BMC Biotechnology, Biomed Central Ltd., London, GB, vol. 11(1):87, Sep. 23, 2011.
Semizarov, D., et al. "Stereoisomers of Deoxynucleoside 5'-Triphosphates as Substrates for Template-dependent and-independent DNA Polymerases," J. of Biol. Chem., 272(14):9556-9560, (Apr. 4, 1997).
Seo, T., et al., "Four-color DNA sequencing by synthesis on a chip using photocleavable fluorescent nucleotides," PNAS, 102(17):5926-5933, (Apr. 26, 2005).
Sgaramella V. et al. "Studies on polynucleotides, C. A novel joining reaction catalyzed by T4-polynucleotide ligase" P.N.A.S. 67: 1468-1475, 1970.
Shabarova, Z., et al., "Chemical ligation of DNA: the first non-enzymatic assembly of a biologically active gene," Nucl. Acids Res., 19(15):4247-4251, (1991).
Shao, Z., et al. "Random-Priming in Vitro Recombination: An Effective Tool for Directed Evolution," Nucleic Acids Research, 26(2):681-683, (1998).
Shendure et al., "Accurate Multiplex Polony Sequencing of an Evolved Bacterial Genome," Science. 309:1728-1732 (2005).
Shpaer, GeneAssist. Smith-Waterman and other database similarity searches and identification of motifs: Methods Mol. Biol. 70: 173-187, 1997.
Sieber, V., et al. "Libraries of Hybrid Proteins From Distantly Related Sequences," Nature Biotechnology, 19:456-460, (May 2001).
Simon, D., et al. "N-methyl-D-aspartate receptor antagonists disrupt the formation of a mammalian neural map" Proc Natl Acad Sci USA, 89:10593-10597, (Nov. 1992).
Smith et al., Mutation Detection with MutH, MutL, and MutS Mismatch Repair Proteins, Proc. Natl. Acad. Sci. USA, 93:4374-4379, (Apr. 1996).
Smith et al., Single-step purification of polypeptides expressed in *Escherichia coli* as fusions with glutathione Transferase, Gene, vol. 67, Issue 1, pp. 31-40, (1988).
Smith, H.O., et al. "Generating a synthetic genome by whole genome assembly:<DX174 bacteriophage from synthetic oligonucleotides," PNAS, 100(26):15440-15445 (2003).
Smith, J., et al. A detailed study of the substrate specificity of a chimeric restriction enzyme. Nucleic Acids Research 27(2):674-681 (1999).
Soderlind et al. "Domain libraries: Synthetic diversity for de novo design of antibody V-regions." Gene, 160 (1995) 269-272.
Sprinzl et al., Compilation of tRNA sequences and sequences of tRNA genes, Nucleic Acids Research, 33:D139-D140 (2005).
Stamm et al., Sanchored PCR: PCR with CDNA Coupled to a solid phase, Nucleic Acids Research, 19(6):1350, (Mar. 25, 1991).
Stekel D. "Microarrays: Making Them and Using Them in Microarray Bioinformatics," Microarray Bioinformatics, Cambridge University Press, 2003.

Stemmer et al. "Single-step assembly of a gene and entire plasmid from large numbers of oligodeoxyribonucleotides" Gene 164: 49 (1995).
Stemmer, DNA shuffling by random fragmentation and reassembly: in vitro recombination for molecular evolution, Proc. Natl. Acad. Sci. USA, 91:10747-10751, (1994).
Sternberg et al. Site-specific Recombination and its Role in the Life Cycle of Bacteriophage P1 Cold Spring Harbor Symp. Quant. Biol. 45: 297-309, 1981.
Steuer et al., Chimeras of the Homing Endonuclease Pi-SeeI and the Homologous Candida Tropicalis Intein: A Study to Explore the Possibility of Exchanging DNA-Binding Modules to Obtain Highly Specific Endonucleases With Altered Specificity,ChemBioChem., 5(2):206-213, (2004).
Strizhov N. et al. "A synthetic crylC gene, encoding a Bacillus thuringiensis delta-endotoxin, confers Spodoptera resistance in Alfalfa and Tobacco" PNAS, 93(26):15012-15017 (1996).
Szybalski et al., Class-IIS restriction enzymes—a review. Gene. Apr. 1991;100:13-26. Review. Erratum in: Gene Dec. 20, 1991;109(1):169.
Tan, S., et al. "Zinc-finger protein-targeted gene regulation: Genomewide single-gene specificity," PNAS, 100(21):11997-12002, (Oct. 14, 2003).
Tang K. et al. Chip-based genotyping by mass spectrometry. PNAS, 96: 10016-10020 (1999).
Teh et al., Droplet microfluidics, Lab on Chip. 2008;8(2):198-220.
Tian et al., "Accurate multiplex gene synthesis from programmable DNA microchips," Nature, 432:1050-1054, (Dec. 2004).
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014. Online Methods.
Tsutakawa et al., The Structural Basis of Damaged DNA Recognition and Endonucleolytic Cleavage for Very Short Patch Repair Endonuclease, Nucleic Acids Research, 29(18):3775-3783, (2001).
Tucker et al., Massively parallel sequencing: the next big thing in genetic medicine. Am J Hum Genet. Aug. 2009;85(2):142-54. doi:10.1016/j.ajhg.2009.06.022.
Urata, H., et al. "Synthesis and properties of mirror-image DNA," Nucleic Acids Research, 20(13):3325-3332 (1992).
Venkatesan et al., Improved Utility of Photolabile Solid Phase Synthesis Supports for the Synthesis of Oligonucleotides Containing 3'-Hydroxyl Termini, J. of Org. Chem., 61:525-529, (Jan. 26, 1996).
Verma et al., Modified Oligonucleotides: Synthesis and Strategy for Users, Annu. Rev. Biochem., 67:99-134, (1998).
Vogelstein et al., "Digital PCR," Pro. Natl. Acad. Sci. 96(16):9236-9241 (1999).
Von Neumann, J. "The general and logical theory of automata," Pergamon Press, 5:288-326, (1948).
Wang et al., De novo assembly and characterization of root transcriptome using Illumina paired-end sequencing and development of cSSR markers in sweetpotato (*Ipomoea batatas*), BMC Genomics, 2010, vol. 11, pp. 1-14.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Waters, V. "Conjugation between bacterial and mammalian cells," Nature Genetics, 29:375-376, (Dec. 2001).
Weber et al. A Modular Cloning System for Standardized Assembly of Multigene Constructs, PLoS ONE, Feb. 18, 2011, vol. 6, No. 2, pp. e16765.
Weiler et al., Combining the Preparation of Oligonucleotide Arrays and Synthesis of High-Quality Primers, Analytical Biochemistry, 243:218-227, (1996).
Weiner et al., Kits and their unique role in molecular biology: a brief retrospective. Bio techniques. Apr. 2008;44(5):701-4. doi: 10.2144/000112796.
Weisberg, et al., Site-specific recombination in Phage Lambda, In: Lambda II, Hendrix, et al. Eds., Cold Spring Harbor Press, Cold Spring Harbor, NY (1983) pp. 211-250.

(56) References Cited

OTHER PUBLICATIONS

Werner et al., Fast track assembly of multigene constructs using Golden Gate cloning and the MoClo system, Bioengineered Bugs, Jan. 1, 2012;3(1):38-43.
Wheeler, D., et al. "Database resources of the National Center for Biotechnology Information," Nucleic Acids Res., 29(1):11-16, (2001).
White et al. (Digital PCR provides sensitive and absolute calibration for high throughput sequencing, BMC Genomics, 2009, 10:116, Published: Mar. 19, 2009).
Wiedmann et al., Ligase chain reaction (LCR)—overview and applications. PCR Methods Appl. Feb. 1994;3(4):S51-64.
Wilgenbus et al., DNA chip technology ante portas, J. Mol. Med, 77:761-768, (1999).
Williams et al., Modifying the stereochemistry of an enzyme-catalyzed reaction by directed evolution. Proc Natl Acad Sci U S A. Mar. 18, 2003;100(6):3143-8. Epub Mar. 7, 2003.
Williams, Restriction Endonucleases. MolecularWorkshop.com. 2005. 14 pages. Accessible at www.molecularworkshop.com/data/endonucleases.html.
Xie et al., An Expanding Genetic Code, Methods a Companion to Methods in Enzymology, 36:227-238, (2005).
Xiong et al. "PCR based accurate synthesis of long DNA sequences" Nature protocols 1 (2): 791 (2006).
Xiong et al., Non-polymerase-cycling-assembly-based chemical gene synthesis: strategies, methods, and progress. Biotechnol Adv. Mar.-Apr. 2008;26(2):121-34. Epub Nov. 7, 2007.
Xiong, A., et al. "A simple, rapid, high-fidelity and cost-effective PCR-based two-step DNA synthesis method for long gene sequences," Nucleic Acids Research, 32(12):e98 (10 pages), (2004).
Xu, Y. and Kool, E., "A Novel 5'-Iodonucleoside allows efficient nonenzymatic ligation of single-stranded and duplex DNAs" Tetrahedron Letter, 38(32):5595-5598, (Aug. 11, 1997).
Xu, Y. and Kool, E., "High sequence fidelity in a non-enzymatic DNA autoligation reaction" Nuc. Acids Res., 27(3):875-881, (1999).
Xu, Y., et al., "Nonenzymatic autoligation in direct three-color detection of RNA and DNA point mutations" Nature Biotech., 19:148-52, (Feb. 2001).
Xuei et al. Use of SAM(2)(R) biotin capture membrane in microarrayed compound screening (mu ARCS) format for nucleic acid polymerization assays Journal of Biomolecular Screening 8:273-282 (2003).
Yan et al., Polymer membranes with two-dimensionally arranged pores derived from monolayers of silica particles, Chem. Mater. 16(9): 1622-1626 (2004).
Yehezkel et al. (De novo DNA synthesis using single molecule PCR, Nucleic Acids Research, 2008, vol. 36, No. 17, e107, Published online Jul. 30, 2008).
Yolov et al. RNA-synthesis by use of T7-RNA-Polymerase and immobilized DNA in a flowing-type reactor. Bioorganicheskaya Khimiya, 17:789-794 (1991 ).
Yoon et al., Efficient cloning and engineering of entire mitochondrial genomes in *Escherichia coli* and transfer into transcriptionally active mitochondria, Nucleic Acids Research, 31(5):1407-1415, (2003).
Yoon, Y., et al. "Cre/loxP-mediated in vivo excision of large segments from yeast genome and their amplification based on the 2 um plasmid-derived system," Gene, 223:67-76, (1998).
Yosef et al., Restoration of gene function by homologous recombination: from PCR to gene expression in one step. Appl. Environ. Microbiol. Dec. 2004;70(12):7156-60.
Young et al., Two-step Total Gene Synthesis Method Nucleic Acids Research, 32(7):e59 (6 pages), (2004).
Zha, D., et al. "Assembly of Designed Oligonucleotides as an Efficient Method for Gene Recombination: A New Tool in Directed Evolution," ChemBioChem, 4:34-39, (2003).
Zhang, C., et al., "PCR microfluidic devices for DNA amplification," Biotechnology Advances, 24(3):243-284, 2006.
Zhang, P. et al. "Rational Design of a Chimeric Endonuclease Targeted to NotI Recognition Site" Protein Engineering Design & Selection, 20(10):497-504, (Oct. 2007).
Zhang, Z., et al. "Selective Incorporation of 5-Hydroxytryptophan Into Proteins in Mammalian Cells," Proceedings of the National Academy of Sciences of the United States of America, 101(24):8882-8887, (Jun. 15, 2004).
Zhao, H., et al. "Molecular Evolution by Staggered Extension Process (StEP) in Vitro Recombination," Nature Biotechnology, 16:258-261, (Mar. 1998).
Zhou et al., Properties of Class-II Restriction Endonucleases. Bulletin of Biology. 1985. 40:26-8.
Zhou X. et al. "Microfluidic PicoArray synthesis of oligodeoxynucleotides and simultaneous assembling of multiple DNA sequences" Nucleic Acids Research , 32(18): 5409-5417 (2004).
Zhu et al., (1995). Cleavage-dependent Ligation by the FLP Recombinase. J Biol Chem 270: 23044-23054.
Zhu et al., A Novel Coronavirus from Patients with Pneumonia in China, 2019. N Engl J Med. Feb. 20, 2020;382:727-33. doi: 10.1056/NEJMoa2001017.
EP 21177267.8, Jan. 17, 2022, Extended European Search Report.

\* cited by examiner

Sequence of Ligation Product Compared to Expected

\>lcl|42826 2
Length=550

Score = 623 bits (337), Expect = 0.0
Identities = 337/337 (100%), Gaps = 0/337 (0%)
Strand = Plus / Plus

```
Query 1    GGAGGGTTGCGTTTGAGACGGGGACAGATCATATGCGGAGGCGGTGATCGCCGAGGTG   60
           ||||||||||||||||||||||||||||||||||||||||||||||||||||||||||
Sbjct 102  GGAGGGTTGCGTTTGAGACGGGGACAGATCATATGCGGAGGCGGTGATCGCCGAGGTG   161

Query 61   AGCACGCAGCTGTCCGAGGTGGTCCGTCATCGAGCGCCACCTGGAGCCGACGCTGCTG   120
           ||||||||||||||||||||||||||||||||||||||||||||||||||||||||||
Sbjct 162  AGCACGCAGCTGTCCGAGGTGGTCCGTCATCGAGCGCCACCTGGAGCCGACGCTGCTG   221

Query 121  GCCGTCCACCTGTACGGCAGCGCCCGTGGACGGCAGCGCCCTGAAGCCTCACTCCGACATCGAT   180
           ||||||||||||||||||||||||||||||||||||||||||||||||||||||||||
Sbjct 222  GCCGTCCACCTGTACGGCAGCGCCCGTGGACGGCAGCGCCCTGAAGCCTCACTCCGACATCGAT   281

Query 181  CTGCTGGAGACGTCCGCCTCCGCCCCCGGGAGAGCGAGATCCGCCTCTGATCAACGAC   240
           ||||||||||||||||||||||||||||||||||||||||||||||||||||||||||
Sbjct 282  CTGCTGGAGACGTCCGCCTCCGCCCCCGGGAGAGCGAGATCCGCCTCTGATCAACGAC   341

Query 241  CTGCTGGAGACGTCCGCCTCCGCCCCCGGGAGAGCGAGATCCTCCGGCTGTGGAGGTGACC   300
           ||||||||||||||||||||||||||||||||||||||||||||||||||||||||||
Sbjct 342  CTGCTGGAGACGTCCGCCTCCGCCCCCGGGAGAGCGAGATCCTCCGGCTGTGGAGGTGACC   401

Query 301  ATCGTGGTGCACGACGACATCATCCCTTGGCGCTACC   337
           |||||||||||||||||||||||||||||||||||||
Sbjct 402  ATCGTGGTGCACGACGACATCATCCCTTGGCGCTACC   438
```

COMPOSITIONS AND METHODS FOR HIGH FIDELITY ASSEMBLY OF NUCLEIC ACIDS

RELATED APPLICATIONS

This application is a continuation of U.S. application Ser. No. 13/592,827, filed Aug. 23, 2012, which claims the benefit of and priority to U.S. Provisional Application No. 61/527,922, filed Aug. 26, 2011, and U.S. Provisional Application No. 61/532,825, filed Sep. 9, 2011, each of which is incorporated herein by reference in its entirety.

STATEMENT REGARDING FEDERALLY SPONSORED RESEARCH

This invention was made with United States Government support under the cooperative agreement number 70NANB7H7034N awarded by the National Institute of Standards and Technology. The United States Government has certain rights in the invention.

FIELD OF THE INVENTION

Methods and compositions of the invention relate to nucleic acid assembly, and particularly to high fidelity, multiplex nucleic acid assembly reactions.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids. Chemically synthesized polynucleotides are often used as primers or adaptors for nucleic acid amplification, mutagenesis, and cloning.

Techniques also are being developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids that can be used in research, industry, agriculture, and/or medicine. However, one limitation of currently available assembly techniques is the relatively high error rate. As such, high fidelity, low cost assembly methods are needed.

SUMMARY OF THE INVENTION

Aspects of the invention relate to methods of producing a target nucleic acid. The method, according to some embodiments, includes: (1) providing a plurality of blunt-end double-stranded nucleic acid fragments having a restriction enzyme recognition sequence at both ends of each of the plurality of blunt-end double-stranded nucleic acid fragments; (2) producing a plurality of cohesive-end double-stranded nucleic acid fragments via enzymatic digestion of the plurality of blunt-end double-stranded nucleic acid fragments in proximity of the restriction enzyme recognition sequence, wherein each of the plurality of cohesive-end double-stranded nucleic acid fragments have two different and non-complementary overhangs; (3) ligating the plurality of cohesive-end double-stranded nucleic acid fragments with a ligase, wherein a first overhang of a first cohesive-end double-stranded nucleic acid fragment is uniquely complementary to a second overhang of a second cohesive-end double-stranded nucleic acid fragment; and (4) forming a linear arrangement of the plurality of cohesive-end double-stranded nucleic acid fragments, wherein the unique arrangement comprises the target nucleic acid. In certain embodiments, the plurality of blunt-end double-stranded nucleic acid fragments can be provided by releasing a plurality of oligonucleotides synthesized on a solid support, and synthesizing complementary strands of the plurality of oligonucleotides using a polymerase based reaction.

In another aspect of the invention, a method for designing a plurality of starting nucleic acids to be assembled into a target nucleic acid is provided. The method, according to some embodiments, can include: (1) obtaining a target sequence of a target nucleic acid; (2) selecting a plurality of subsequences therein such that every two adjacent subsequences overlap with each other by N bases; (3) storing the resulting overlapping N-base sequences in a memory; (4) comparing the overlapping N-base sequences to one another to ensure that they differ from one another by at least one base; and (5) repeating steps (2) to (4) until a plurality of satisfactory starting nucleic acids are obtained wherein any two adjacent starting nucleic acids uniquely overlap with each other by N bases.

Yet another aspect of the invention relates to a plurality of starting nucleic acids to be assembled into a target nucleic acid, designed according to the methods described herein. In certain embodiments, the plurality of starting nucleic acids can each further include an engineered universal primer binding site for amplifying the plurality of starting nucleic acids therefrom. The plurality of starting nucleic acids can also each further include an engineered restriction enzyme recognition sequence.

In still another aspect, a system for assembling a target nucleic acid is provided. The system includes: (1) a solid support for synthesizing the plurality of starting nucleic acids described herein, wherein each starting nucleic acid further comprises an engineered universal primer binding site and an engineered restriction enzyme recognition sequence; (2) a polymerase reaction unit for synthesizing complementary strands of the plurality of starting nucleic acids a polymerase based reaction using a universal primer complementary to the universal primer binding site, thereby producing a plurality of blunt-end double-stranded nucleic acid fragments; (3) a digestion unit for producing a plurality of cohesive-end double-stranded nucleic acid fragments via enzymatic digestion of the plurality of blunt-end double-stranded nucleic acid fragments in proximity of the restriction enzyme recognition sequence, wherein the plurality of cohesive-end double-stranded nucleic acid fragments each have two different and non-complementary overhangs; and (4) a ligation unit for ligating the plurality of cohesive-end double-stranded nucleic acid fragments with a ligase, wherein a first overhang of a first cohesive-end double-stranded nucleic acid fragment is uniquely complementary to a second overhang of a second cohesive-end double-stranded nucleic acid fragment.

A further aspect of the invention provides a computer program product for designing a plurality of starting nucleic acids to be assembled into a target nucleic acid, said program residing on a hardware computer readable storage medium and having a plurality of instructions which, when executed by a processor, cause the processor to perform operations comprising: (1) obtaining a target sequence of a target nucleic acid; (2) selecting a plurality of subsequences therein such that every two adjacent subsequences overlap with each other by N bases; (3) storing the resulting overlapping N-base sequences in a memory; (4) comparing the overlapping N-base sequences to one another to ensure that they differ from one another by at least one base; and (5) repeating steps (2) to (4) until a plurality of satisfactory starting nucleic acids are obtained wherein any two adjacent starting nucleic acids uniquely overlap with each other by N bases.

BRIEF DESCRIPTION OF THE FIGURES

FIGS. 1A and 1B illustrate an exemplary design of oligonucleotides for a multiplex oligonucleotide assembly reaction (SEQ ID NO: 3).

FIG. 6 illustrates sequencing confirmation of the products of the multiplex oligonucleotide assembly reaction of FIG. 4 (SEQ ID NO: 4).

Figure 8A:
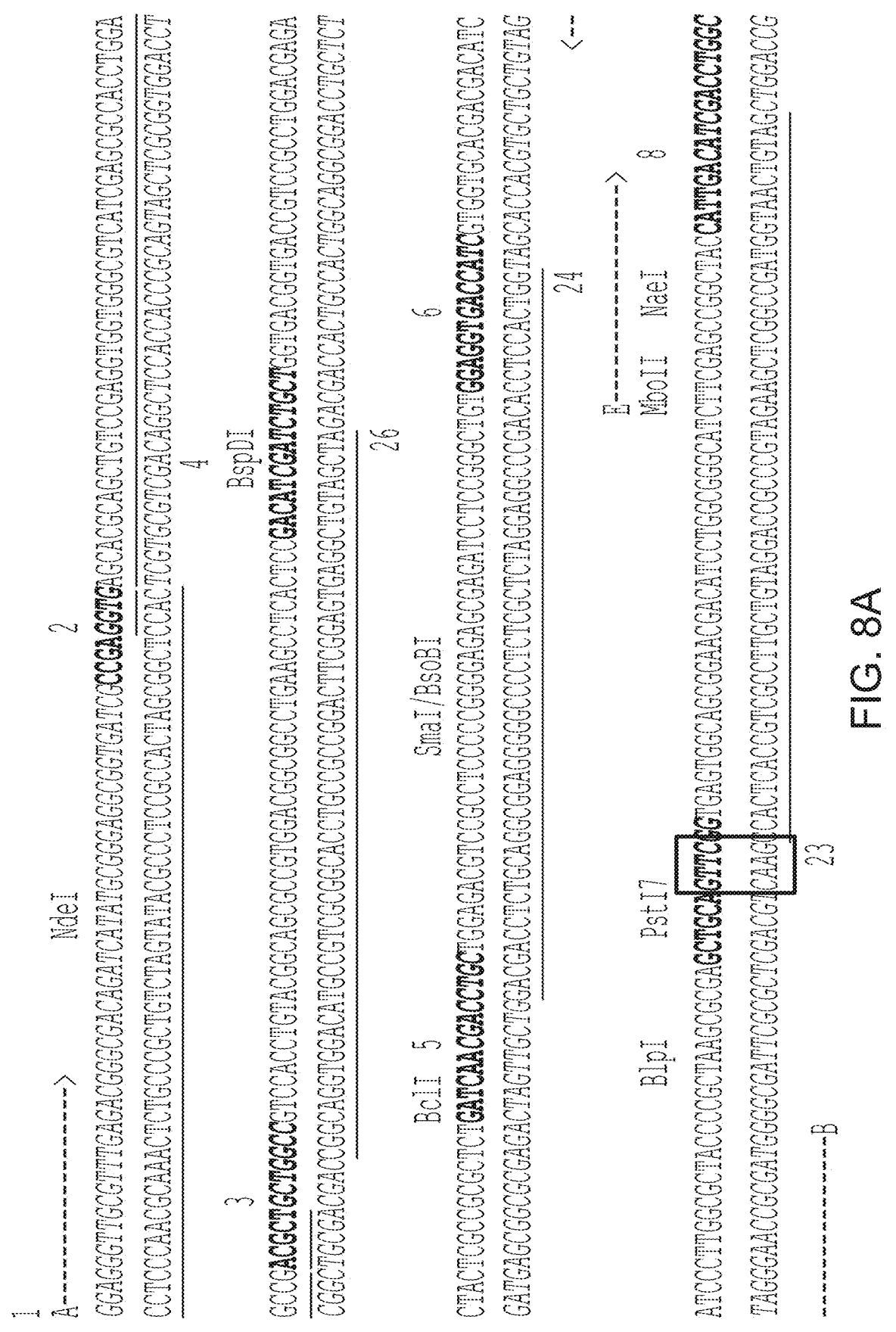
Figure 8B:
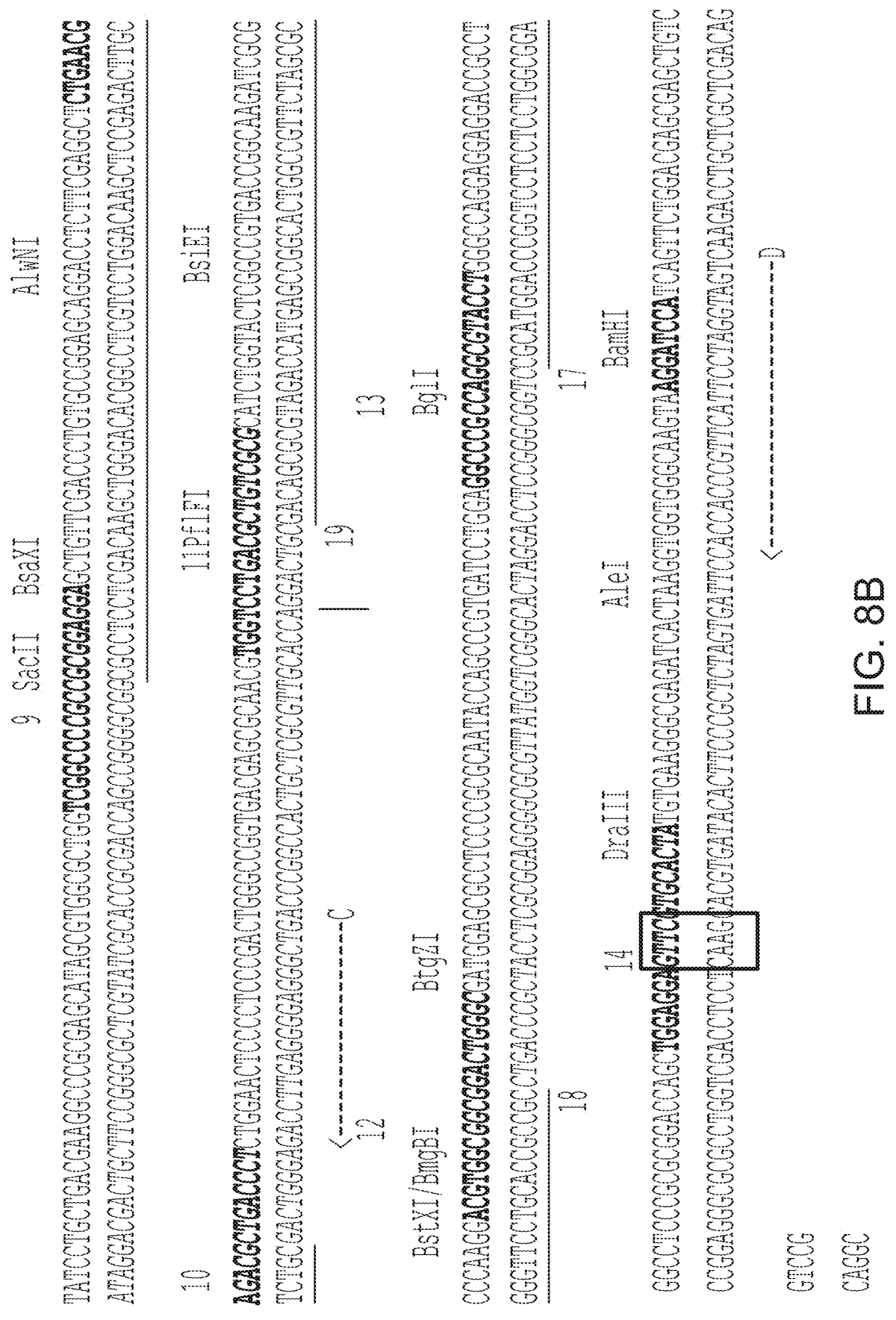

FIGS. 8A and 8B illustrate alternative assembly products (SEQ ID NO: 3) based on the design of FIG. 1.

DETAILED DESCRIPTION OF THE INVENTION

Figure 2:
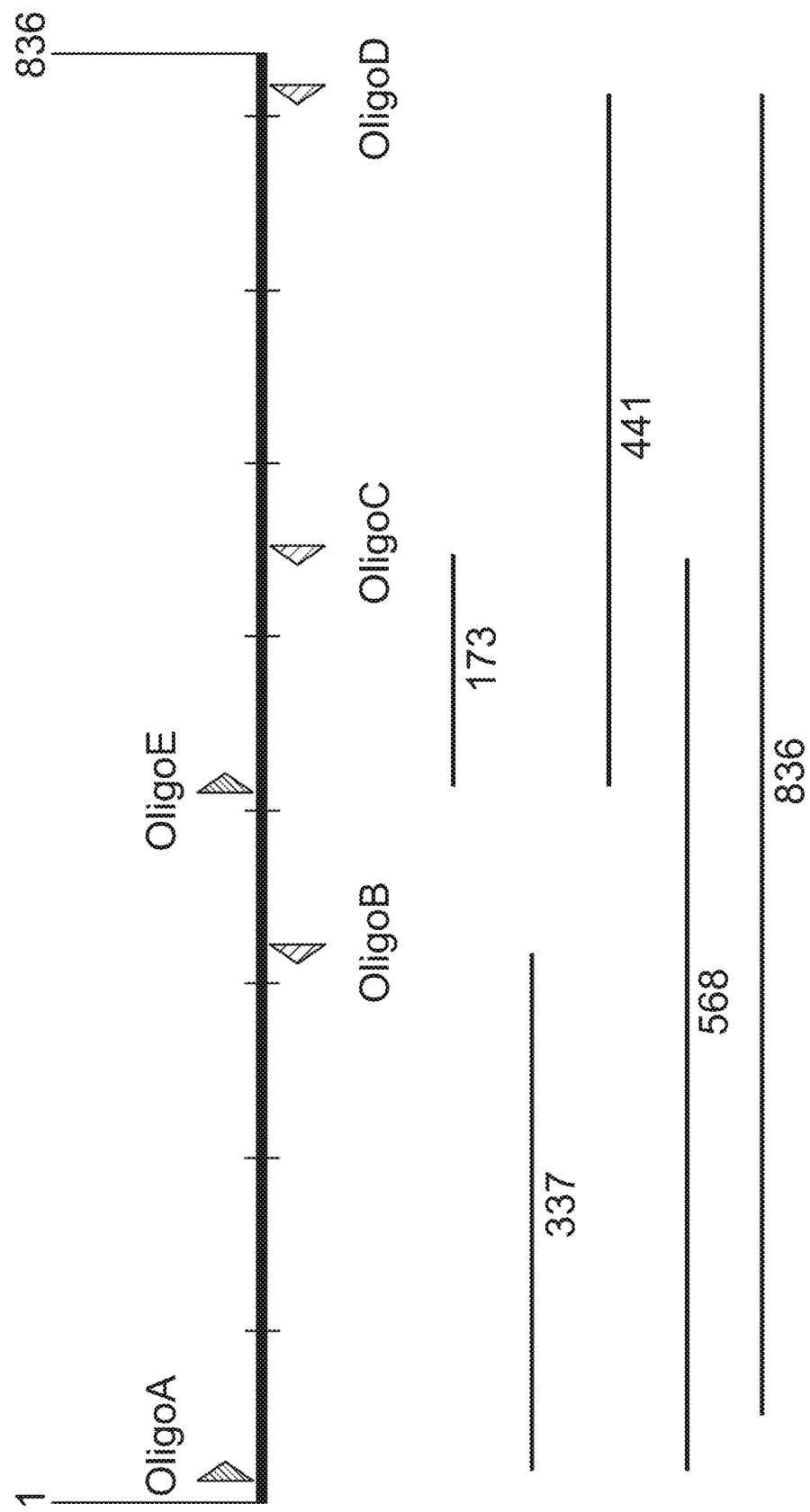
FIG. 2 illustrates relative position of primers used for testing products from the multiplex assembly reaction.

Aspects of the invention relate to methods and compositions for covalently joining a plurality of nucleic acid fragments to produce a longer nucleic acid product in a single assembly step. Aspects of the invention can be used to assemble large numbers of nucleic acid fragments efficiently, and/or to reduce the number of steps required to generate large nucleic acid products, while reducing assembly error rate. Aspects of the invention can be incorporated into nucleic acid assembly procedures to increase assembly fidelity, throughput and/or efficiency, decrease cost, and/or reduce assembly time. In some embodiments, aspects of the invention may be automated and/or implemented in a high throughput assembly context to facilitate parallel production of many different target nucleic acid products.

Multiplex Oligonucleotide Assembly

A predetermined nucleic acid fragment may be assembled from a plurality of different starting nucleic acids (e.g., oligonucleotides) in a multiplex assembly reaction (e.g., a multiplex enzyme-mediated reaction, a multiplex chemical assembly reaction, or a combination thereof). Certain aspects of multiplex nucleic acid assembly reactions are illustrated by the following description of certain embodiments of multiplex oligonucleotide assembly reactions. It should be appreciated that the description of the assembly reactions in the context of oligonucleotides is not intended to be limiting. The assembly reactions described herein may be performed using starting nucleic acids obtained from one or more different sources (e.g., synthetic or natural polynucleotides, nucleic acid amplification products, nucleic acid degradation products, oligonucleotides, etc.). The starting nucleic acids may be referred to as assembly nucleic acids (e.g., assembly oligonucleotides). As used herein, an assembly nucleic acid has a sequence that is designed to be incorporated into the nucleic acid product generated during the assembly process. However, it should be appreciated that the description of the assembly reactions in the context of double-stranded nucleic acids is not intended to be limiting. In some embodiments, one or more of the starting nucleic acids illustrated in the figures and described herein may be provided as single-stranded nucleic acids. Accordingly, it should be appreciated that where the figures and description illustrate the assembly of cohesive-end double-stranded nucleic acids, the presence of one or more single-stranded nucleic acids is contemplated.

As used herein, an oligonucleotide may be a nucleic acid molecule comprising at least two covalently bonded nucleotide residues. In some embodiments, an oligonucleotide may be between 10 and 1,000 nucleotides long. For example, an oligonucleotide may be between 10 and 500 nucleotides long, or between 500 and 1,000 nucleotides long. In some embodiments, an oligonucleotide may be between about 20 and about 300 nucleotides long (e.g., from about 30 to 250, 40 to 220, 50 to 200, 60 to 180, or about 65 or about 150 nucleotides long), between about 100 and about 200, between about 200 and about 300 nucleotides, between about 300 and about 400, or between about 400 and about 500 nucleotides long. However, shorter or longer oligonucleotides may be used. An oligonucleotide may be a single-stranded nucleic acid. However, in some embodiments a double-stranded oligonucleotide may be used as described herein. In certain embodiments, an oligonucleotide may be chemically synthesized as described in more detail below. In some embodiments, an input nucleic acid (e.g., synthetic oligonucleotide) may be amplified before use. The resulting product may be double-stranded.

In certain embodiments, each oligonucleotide may be designed to have a sequence that is identical to a different portion of the sequence of a predetermined target nucleic acid that is to be assembled. Accordingly, in some embodiments each oligonucleotide may have a sequence that is identical to a portion of one of the two strands of a double-stranded target nucleic acid. For clarity, the two complementary strands of a double stranded nucleic acid are referred to herein as the positive (P) and negative (N) strands. This designation is not intended to imply that the strands are sense and anti-sense strands of a coding sequence. They refer only to the two complementary strands of a nucleic acid (e.g., a target nucleic acid, an intermediate nucleic acid fragment, etc.) regardless of the sequence or function of the nucleic acid. Accordingly, in some embodiments a P strand may be a sense strand of a coding sequence, whereas in other embodiments a P strand may be an anti-sense strand of a coding sequence. It should be appreciated that the reference to complementary nucleic acids or complementary nucleic acid regions herein refers to nucleic acids or regions thereof that have sequences which are reverse complements of each other so that they can hybridize in an antiparallel fashion typical of natural DNA.

According to one aspect of the invention, a target nucleic acid may be either the P strand, the N strand, or a double-stranded nucleic acid comprising both the P and N strands. It should be appreciated that different oligonucleotides may be designed to have different lengths. In some embodiments, one or more different oligonucleotides may have overlapping sequence regions (e.g., overlapping 5' regions and/or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 2 and about 50 (e.g., between 3 and 20, between 3 and 10, between 3 and 8, or 4, 5, 6, 7, 8, 9, etc. nucleotides long). However, shorter, longer or intermediate overlapping lengths may be used. It should be appreciated that overlaps between different input nucleic acids used in an assembly reaction may have different lengths and/or sequences. For example, the overlapping sequences may be different than one another by at least one nucleotide, 2 nucleotides, 3 nucleotides, or more. Assuming that the overlapping sequences differ from one another by x nucleotides, then up to $(4^x+1)$ pieces of different input nucleic acids can be assembled together in one reaction.

In a multiplex oligonucleotide assembly reaction designed to generate a predetermined nucleic acid fragment, the combined sequences of the different oligonucleotides in the reaction may span the sequence of the entire nucleic acid fragment on either the positive strand, the negative strand, both strands, or a combination of portions of the positive strand and portions of the negative strand. The plurality of different oligonucleotides may provide either positive sequences, negative sequences, or a combination of both positive and negative sequences corresponding to the entire sequence of the nucleic acid fragment to be assembled. In some embodiments, the plurality of oligonucleotides may include one or more oligonucleotides having sequences identical to one or more portions of the positive sequence, and one or more oligonucleotides having sequences that are identical to one or more portions of the negative sequence of the nucleic acid fragment. One or more pairs of different oligonucleotides may include sequences that are identical to overlapping portions of the predetermined nucleic acid fragment sequence as described herein (e.g., overlapping sequence portions from the same or from complementary strands of the nucleic acid fragment). In some embodiments, the plurality of oligonucleotides includes a set of oligonucleotides having sequences that combine to span the entire positive sequence and a set oligonucleotides having sequences that combine to span the entire negative sequence of the predetermined nucleic acid fragment. However, in certain embodiments, the plurality of oligonucleotides may include one or more oligonucleotides with sequences that are identical to sequence portions on one strand (either the positive or negative strand) of the nucleic acid fragment, but no oligonucleotides with sequences that are complementary to those sequence portions. In one embodiment, a plurality of oligonucleotides includes only oligonucleotides having sequences identical to portions of the positive sequence of the predetermined nucleic acid fragment. In one embodiment, a plurality of oligonucleotides includes only oligonucleotides having sequences identical to portions of the negative sequence of the predetermined nucleic acid fragment. These oligonucleotides may be assembled by sequential ligation or in an extension-based reaction (e.g., if an oligonucleotide having a 3' region that is complementary to one of the plurality of oligonucleotides is added to the reaction).

In one aspect, a nucleic acid fragment may be assembled in a ligase-mediated assembly reaction from a plurality of oligonucleotides that are combined and ligated in one or more rounds of ligase-mediated ligations. Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. In some embodiments, one or more low temperature (e.g., room temperature or lower) ligases may be used (e.g., T3 DNA ligase, T4 DNA ligase, T7 DNA ligase, and/or *E. coli* DNA Ligase). A lower temperature ligase may be useful for shorter overhangs (e.g., about 3, about 4, about 5, or about 6 base overhangs) that may not be stable at higher temperatures. A ligase may also be a heat-stable ligase. In some embodiments, a thermostable ligase from a thermophilic organism may be used. Examples of thermostable DNA ligases include, but are not limited to: Tth DNA ligase (from *Thermus thermophilics*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof.

Figure 1A:
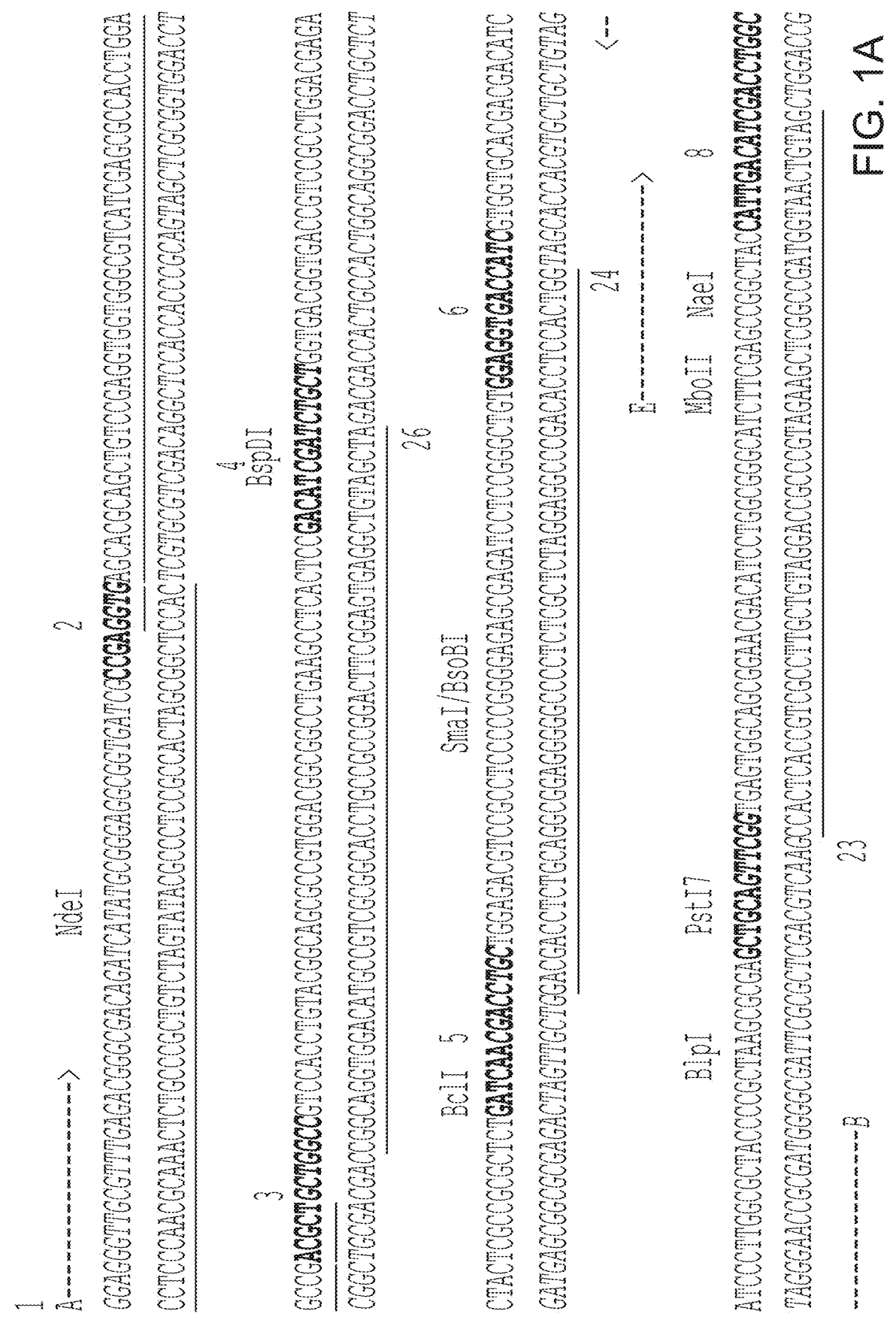

Aspects of the invention may be used to enhance different types of nucleic acid assembly reactions (e.g., multiplex nucleic acid assembly reactions). Aspects of the invention may be used in combination with one or more assembly reactions described in, for example, Carr et al., 2004, Nucleic Acids Research, Vol. 32, No 20, e162 (9 pages); Richmond et al., 2004, Nucleic Acids Research, Vol. 32, No 17, pp. 5011-5018; Caruthers et al., 1972, J. Mol. Biol. 72, 475-492; Hecker et al., 1998, Biotechniques 24:256-260: Kodumal et al., 2004, PNAS Vol. 101, No. 44, pp. 15573-15578; Tian et al., 2004, Nature, Vol. 432, pp. 1050-1054; and U.S. Pat. Nos. 6,008,031 and 5,922,539, the disclosures of which are incorporated herein by reference. Certain embodiments of multiplex nucleic acid assembly reactions for generating a predetermined nucleic acid fragment are illustrated with reference to FIGS. 1-10. It should be appreciated that synthesis and assembly methods described herein (including, for example, oligonucleotide synthesis, stepwise assembly, multiplex nucleic acid assembly, hierarchical assembly of nucleic acid fragments, or any combination thereof) may be performed in any suitable format, including in a reaction tube, in a multi-well plate, on a surface, on a column, in a microfluidic device (e.g., a microfluidic tube), a capillary tube, etc. For example, some embodiments, the target nucleic acid can be assembled by "recursive assembly" or "hierarchical assembly." In this embodiment, the target nucleic acid is divided first into two or more overlapping nucleic acid fragments (or subassembly fragments). Each nucleic acid fragments is then subdivided into two or more overlapping smaller nucleic acid fragments.

Synthetic Oligonucleotides

Oligonucleotides may be synthesized using any suitable technique. For example, oligonucleotides may be synthesized on a column or other support (e.g., a chip).

Examples of chip-based synthesis techniques include techniques used in synthesis devices or methods available from CombiMatrix, Agilent, Affymetrix, or other sources. A synthetic oligonucleotide may be of any suitable size, for example between 10 and 1,000 nucleotides long (e.g., between 10 and 200, 200 and 500, 500 and 1,000 nucleotides long, or any combination thereof). An assembly reaction may include a plurality of oligonucleotides, each of which independently may be between 10 and 300 nucleotides in length (e.g., between 20 and 250, between 30 and 200, 50 to 150, 50 to 100, or any intermediate number of nucleotides). However, one or more shorter or longer oligonucleotides may be used in certain embodiments.

As used herein, the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials can include but are not limited to, paper, synthetic filters and the like. In such porous materials, the reaction may take place within the pores. The support can have any one of a number of shapes, such as pin, strip, plate, disk, rod, bends, cylindrical structure, particle, including bead, nanoparticle and the like. The support can have variable widths.

The support can be hydrophilic or capable of being rendered hydrophilic. The support can include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like; either used by themselves or in conjunction with other materials.

In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein, the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. The size of the defined feature can be chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

Arrays may be constructed, custom ordered or purchased from a commercial vendor (e.g., CombiMatrix, Agilent, Affymetrix, Nimblegen). Oligonucleotides are attached, spotted, immobilized, surface-bound, supported or synthesized on the discrete features of the surface or array. Oligonucleotides may be covalently attached to the surface or deposited on the surface. Various methods of construction are well known in the art, e.g., maskless array synthesizers, light directed methods utilizing masks, flow channel methods, spotting methods etc.

In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854; 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-wells microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

Other suitable microarrays and methods for synthesizing oligonucleotides include those described in U.S. Pat. Nos. 7,323,320 and 7,563,600, the entire disclosures of which are hereby incorporated herein by reference in their entirety. In an example, the oligonucleotides synthesized therefrom are chemically, enzymatically, or physically cleaved or otherwise released from the microarrays for further amplification, restriction enzyme digestion and/or assembly.

In another embodiment, a plurality of oligonucleotides may be synthesized or immobilized (e.g. attached) on multiple supports, such as beads. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In yet another embodiment, a plurality of oligonucleotides may be attached or synthesized on nanoparticles. Nanoparticles includes but are not limited to metal (e.g., gold, silver, copper and platinum), semiconductor (e.g., CdSe, CdS, and CdS coated with ZnS) and magnetic (e.g., ferromagnetite) colloidal materials. Methods to attach oligonucleotides to the nanoparticles are known in the art. In another embodiment, nanoparticles are attached to the substrate. Nanoparticles with or without immobilized oligonucleotides can be attached to substrates as described in, e.g., Grabar et al., Analyt. Chem., 67, 73-743 (1995); Bethell et al., J. Electroanal. Chem., 409, 137 (1996); Bar et al., Langmuir, 12, 1172 (1996); Colvin et al., J. Am. Chem. Soc., 114, 5221 (1992). Naked nanoparticles may be first attached to the substrate and oligonucleotides can be attached to the immobilized nanoparticles.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

A preparation of an oligonucleotide designed to have a certain sequence may include oligonucleotide molecules having the designed sequence in addition to oligonucleotide molecules that contain errors (e.g., that differ from the designed sequence at least at one position). A sequence error may include one or more nucleotide deletions, additions, substitutions (e.g., transversion or transition), inversions, duplications, or any combination of two or more thereof. Oligonucleotide errors may be generated during oligonucleotide synthesis. Different synthetic techniques may be prone to different error profiles and frequencies. In some embodiments, error rates may vary from 1/10 to 1/200 errors per base depending on the synthesis protocol that is used. However, in some embodiments, lower error rates may be achieved. Also, the types of errors may depend on the synthetic techniques that are used. For example, in some embodiments chip-based oligonucleotide synthesis may result in relatively more deletions than column-based synthetic techniques.

In some embodiments, one or more oligonucleotide preparations may be subjected to an error reduction or error filtration process to remove (or reduce the number or the frequency of) error-containing oligonucleotides. Such process can be used to increase the number of error-free oligonucleotides in the oligonucleotide preparations. Methods for conducting error reduction or error filtration can include, for example, hybridization to a selection oligonucleotide, binding to a mismatch binding agent or to a mismatch binding protein or combinations thereof.

In some embodiments, a hybridization technique may be used wherein an oligonucleotide preparation (i.e. construction oligonucleotides) is hybridized under stringent conditions, one or more times, to an immobilized oligonucleotide preparation (i.e. selection oligonucleotides) designed to have a complementary sequence. The term "selection oligonucleotide" as used herein refers to a single-stranded oligonucleotide that is complementary to at least a portion of a construction oligonucleotide (or the complement of the construction oligonucleotide). Selection oligonucleotides may be used for removing copies of a construction oligonucleotide that contain sequencing errors (e.g., a deviation from the desired sequence) from a pool of construction oligonucleotides. In some embodiments, a selection oligonucleotide may be end immobilized on a substrate. Yet in other embodiments, the selection oligonucleotides can be in solution. In one embodiment, selection oligonucleotides can be synthetic oligonucleotides that have been synthesized in parallel on a substrate as disclosed herein.

Construction oligonucleotides that do not bind or that form unstable duplexes may be removed in order to selectively or specifically remove error-containing oligonucleotides that would destabilize hybridization under the conditions used. It should be appreciated that this process may not remove all error-containing oligonucleotides since some error-containing oligonucleotides may still bind to the immobilized selection oligonucleotides with sufficient affinity through this selection process. For example, the error-containing oligonucleotides may differ from the selection oligonucleotide by one or two bases and may still bind to the selection oligonucleotides under the selection process reaction conditions.

In some embodiments, a nucleic acid binding protein or recombinase (e.g., RecA) may be included in one or more of the oligonucleotide processing steps to improve the selection of error-free oligonucleotides. For example, by preferentially promoting the hybridization of oligonucleotides that are completely complementary with the immobilized oligonucleotides, the amount of error-containing oligonucleotides that are bound may be reduced. As a result, the oligonucleotide processing procedure described herein may remove more error-containing oligonucleotides and generate an oligonucleotide preparation that has a lower error frequency (e.g., with an error rate of less than 1/50, less than 1/100, less than 1/200, less than 1/300, less than 1/400, less than 1/500, less than 1/1,000, or less than 1/2,000 errors per base).

In some embodiments, error correction may be included between each process repetition and at the end of the synthesis process to increase the relative population of synthesized polynucleotides without deviation from the desired sequences. Such error correction may include direct sequencing and/or the application of error correction based on correcting enzymes, such as error correcting nucleases (e.g. CEL I), error correction based on MutS or MutS homologs binding or other mismatch binding proteins (see, e.g., International Application No. PCT/US2010/057405), other means of error correction as known in the art or any combination thereof. In an exemplary embodiment, CEL I may be added to the oligonucleotide duplexes in the fluid medium. CEL I is a mismatch specific endonuclease that cleaves all types of mismatches such as single nucleotide polymorphisms, small insertions or deletions. Addition of the endonuclease results in the cleavage of the double-stranded oligonucleotides at the site or region of the mismatch.

It should be appreciated that one or more nucleic acid binding proteins or recombinases are preferably not included in a post-synthesis fidelity optimization technique (e.g., a screening technique using a MutS or MutS homolog), because the optimization procedure involves removing error-containing nucleic acids via the production and removal of heteroduplexes. Accordingly, any nucleic acid binding proteins or recombinases (e.g., RecA) that were included in the synthesis steps is preferably removed (e.g., by inactivation, column purification or other suitable technique) after synthesis and prior to fidelity optimization.

In certain embodiments, it may be helpful to include one or more modified oligonucleotides. An oligonucleotide may be modified by incorporating a modified-base (e.g., a nucleotide analog) during synthesis, by modifying the oligonucleotide after synthesis, or any combination thereof. Examples of modifications include, but are not limited to, one or more of the following: universal bases such as nitro indoles, dP and dK; inosine, uracil; halogenated bases such as BrdU; fluorescent labeled bases; non-radioactive labels such as biotin (as a derivative of dT) and digoxigenin (DIG); 2,4-Dinitrophenyl (DNP); radioactive nucleotides; post-coupling modification such as dR-NH2 (deoxyribose-NEb); Acridine (6-chloro-2-methoxyacridine); and spacer phosphoramides which are used during synthesis to add a spacer "arm" into the sequence, such as C3, C8 (octanediol), C9, C12, HEG (hexaethylene glycol) and C18.

Amplifying Oligonuclotides

Oligonucleotides may be provided or synthesized as single-stranded synthetic products. In some embodiments, oligonucleotides may also be provided or synthesized as double-stranded preparations including an annealed complementary strand. Oligonucleotides may be molecules of DNA, RNA, PNA, or any combination thereof. A double-stranded oligonucleotide may be produced by amplifying a single-stranded synthetic oligonucleotide or other suitable template (e.g., a sequence in a nucleic acid preparation such as a nucleic acid vector or genomic nucleic acid). Accordingly, a plurality of oligonucleotides designed to have the sequence features described herein may be provided as a plurality of single-stranded oligonucleotides having those feature, or also may be provided along with complementary oligonucleotides. In some embodiments, an oligonucleotide may be phosphorylated (e.g., with a 5' phosphate). In some embodiments, an oligonucleotide may be non-phosphorylated.

In some embodiments, an oligonucleotide may be amplified using an appropriate primer pair with one primer corresponding to each end of the oligonucleotide (e.g., one that is complementary to the 3' end of the oligonucleotide and one that is identical to the 5' end of the oligonucleotide). In some embodiments, an oligonucleotide may be designed to contain a central assembly sequence (designed to be incorporated into the target nucleic acid) flanked by a 5' amplification sequence (e.g., a 5' universal sequence) and/or a 3' amplification sequence (e.g., a 3' universal sequence).

Amplification primers (e.g., between 10 and 50 nucleotides long, between 15 and 45 nucleotides long, about 25 nucleotides long, etc.) corresponding to the flanking amplification sequences may be used to amplify the oligonucleotide (e.g., one primer may be complementary to the 3' amplification sequence and one primer may have the same sequence as the 5' amplification sequence). The amplification sequences then may be removed from the amplified oligonucleotide using any suitable technique to produce an oligonucleotide that contains only the assembly sequence.

In some embodiments, a plurality of different oligonucleotides (e.g., about 5, 10, 50, 100, or more) with different central assembly sequences may have identical 5' amplification sequences and/or identical 3' amplification sequences. These oligonucleotides can all be amplified in the same reaction using the same amplification primers.

A plurality of oligonucleotides used in an assembly reaction may contain preparations of synthetic oligonucleotides, single-stranded oligonucleotides, double-stranded oligonucleotides, amplification products, oligonucleotides that are processed to remove (or reduce the frequency of) error-containing variants, etc., or any combination of two or more thereof. In some aspects, double-stranded amplification products may be used as assembly oligonucleotides and added to an assembly reaction as described herein. In some embodiments, the oligonucleotide may be amplified while it is still attached to the support. In some embodiments, the oligonucleotide may be removed or cleaved from the support prior to amplification or after amplification.

In some embodiments, a synthetic oligonucleotide may include a central assembly sequence flanked by 5' and 3' amplification sequences. The central assembly sequence is designed for incorporation into an assembled target nucleic acid or target subassembly. The flanking sequences are designed for amplification and are not intended to be incorporated into the assembled nucleic acid. The flanking amplification sequences may be used as universal primer sequences to amplify a plurality of different assembly oligonucleotides that share the same amplification sequences but have different central assembly sequences. In some embodiments, the flanking sequences are removed after amplification to produce an oligonucleotide that contains only the assembly sequence.

In certain embodiments, the double-stranded amplification products may be subject to restriction enzyme digestion to remove the flanking sequences. To that end, the flanking sequences can be designed to include one or more restriction sites or restriction enzyme recognition sites. The restriction site may be present at the 5' or 3' end of the amplification sequence as long as the cleavage site is between the flanking sequence to be removed and the central assembly sequence. The restriction site may be included in the amplification sequence (i.e., primer binding site). The restriction site may also be outside the amplification sequence.

After restriction enzyme digestion, the cleaved flanking sequences may be separated and removed using any suitable technique. In some embodiments, the cleaved flanking sequences may be fragments less than about 40, about 35, about 30, about 25, about 20, or about 15 bases long. As such, size dependent separation techniques known in the art may be used, such as differential affinity to silica, size filtration, differential precipitation with PEG (polyethylene glycol) or CTAB (cetyltrimethylammonium bromide), or any combination thereof, so as to separate the cleaved flanking sequences from the central assembly sequences that can be designed to be longer in size than the flanking sequences.

In some embodiments, the amplification primers may be biotinylated. The resulting amplification products thus also become biotinylated at both ends. Upon restriction enzyme digestion, the cleaved flanking sequences having the biotinylated primers retain the biotin tags, while the central assembly sequences are non-biotinylated. Thus, the cleaved flanking sequences can be affinity purified and removed using streptavidin (e.g., bound to a bead, column, or other surface). In some embodiments, the amplification primers also may be designed to include certain sequence features (e.g., restriction sites) that can be used to remove the primer regions after amplification in order to produce a double-stranded assembly fragment that includes the assembly sequence without the flanking amplification sequences.

Single-Stranded Overhangs

Certain aspects of the invention involve double-stranded nucleic acids with single-stranded overhangs. Overhangs may be generated using any suitable technique. In some embodiments, a double-stranded nucleic acid fragment (e.g., a fragment assembled in a multiplex assembly) may be digested with an appropriate restriction enzyme to generate a terminal single-stranded overhang. In some embodiments, fragments that are designed to be adjacent to each other in an assembled product may be digested with the same enzyme to expose complementary overhangs. Different enzymes that generate complementary overhangs may also used.

In some embodiments, overhangs may be generated using a type IIS restriction enzyme. Type IIS restriction enzymes are enzymes that bind to a double-stranded nucleic acid at one site, referred to as the recognition site, and make a single double stranded cut outside of the recognition site. The double stranded cut, referred to as the cleavage site, is generally situated 0-20 bases away from the recognition site. The recognition site is generally about 4-8 bp long. All type IIS restriction enzymes exhibit at least partial asymmetric recognition. Asymmetric recognition means that 5'→3' recognition sequences are different for each strand of the nucleic acid. The enzyme activity also shows polarity meaning that the cleavage sites are located on only one side of the recognition site. Thus, there is generally only one double stranded cut corresponding to each recognition site. Cleavage generally produces 1-6 nucleotide single-stranded overhangs, with 5' or 3' termini, although some enzymes produce blunt ends. Either cut is useful in the context of the invention, although in some instances those producing single-stranded overhangs are produced. To date, about 80 type IIS enzymes have been identified. Suitable examples include but are not limited to BstF5 I, BtsC I, BsrD I, Bts I, Alw I, Bcc I, BsmA I, Ear I, Mly I (blunt), Ple I, Bmr I, Bsa I, BsmB I, BspQ I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AclW I, Alw26 1, Bst6 1, BstMA I, Eaml 104 1, Ksp632 I, Pps I$_5$ Sch I (blunt), Bfi I, Bso31 1, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstVl I, Eco571$_5$ Eco57M I$_5$ Gsu I$_5$ and Beg I. In some embodiments, Bsa I, BsmB I, BspQ I, BtgZ I, BsmF I, Fok I, Bbv I, any variant thereof, or any combination thereof can be used. Such enzymes and information regarding their recognition and cleavage sites are available from commercial suppliers such as New England Biolabs.

In some embodiments, each of a plurality of nucleic acid fragments designed for assembly may have a type IIS restriction site at each end. The type IIS restriction sites may be oriented so that the cleavage sites are internal relative to the recognition sequences. As a result, enzyme digestion exposes an internal sequence (e.g., an overhang within an internal sequence) and removes the recognition sequences from the ends. Accordingly, the same type IIS sites may be used for both ends of all of the nucleic acid fragments being prepared for assembly. However, different type IIS sites also may be used. Two fragments that are designed to be adjacent in an assembled product each may include an identical overlapping terminal sequence and a flanking type IIS site that is appropriately located to expose complementary overhangs within the overlapping sequence upon restriction enzyme digestion. Accordingly, a plurality of nucleic acid fragments may be generated with different complementary overhangs. The restriction site at each end of a nucleic acid fragment may be located such that digestion with the appropriate type IIS enzyme removes the restriction site and exposes a single-stranded region that is complementary to a single-stranded region on a nucleic acid fragment that is designed to be adjacent in the assembled nucleic acid product. In certain embodiments, restriction enzymes can be selected such that the assembly nucleic acid fragments are free of the corresponding restriction sites.

Figure 9A:
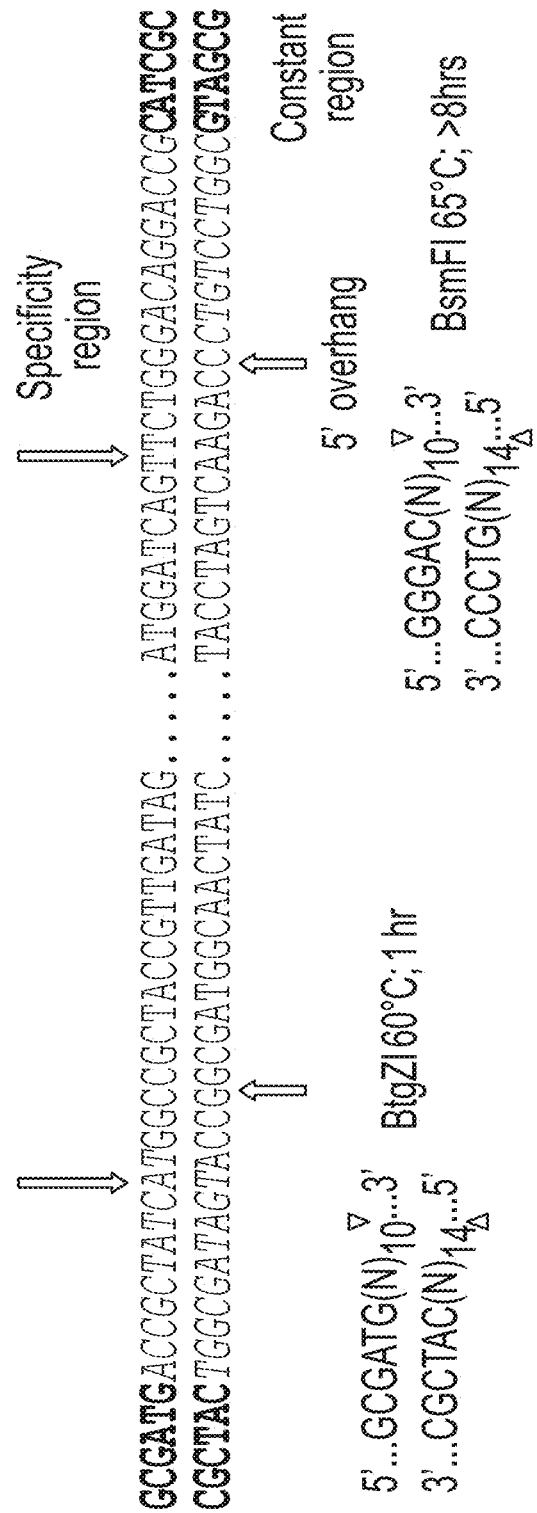
FIG. 9A illustrates a first design strategy for sequences flanking assembly fragments (SEQ ID NO: 5 (left) and SEQ ID NO: 6 (right)).
Figure 9B:
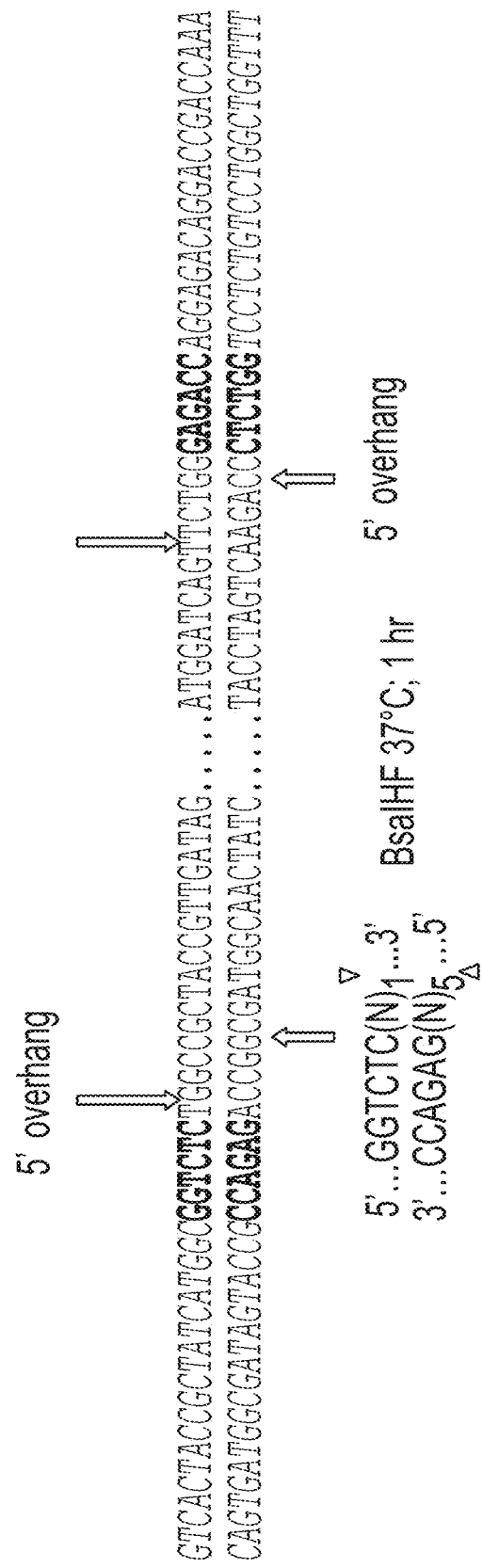
FIG. 9B illustrates a second design strategy for sequences flanking assembly fragments (SEQ ID NO: 7 (left) and SEQ ID NO: 8 (right)).

As discussed above, restriction sites can be placed inside or outside, 5' or 3' to the amplification sequence. As FIG. 9A illustrates, restriction sites (shown in bold) can be included within the amplification sequence (shown in italic) and distal to the central assembly fragment (black). By way of example, BtgZI and BsmFI sites are used at either end of the double-stranded assembly fragment, and their respective cleavage sites are indicated by arrows. BtgZI and BsmFI both cleave at 10 nucleotides/14 nucleotides away from their recognition sites. Other restriction enzymes that cleave at a short distance (e.g., 5-25, 10-20, or about 15 nucleotides) from the recognition site can also be used. Alternatively, as FIG. 9B illustrates, restriction sites (shown in bold) can be outside the amplification sequence (shown in italic) and proximal to the central assembly fragment (normal font). BsaI sites are used at both ends of the double-stranded assembly fragment as an example, the cleavage sites of which are also indicated by arrows. As can be seen from FIGS. 9A and 9B, when restriction sites are placed distal to the central assembly fragment and included in the amplification sequence, the overall length of the starting nucleic acid is shorter than when restriction sites are placed proximal to the central assembly fragment and not included in the amplification sequence. Thus the first strategy (FIG. 9A) can be more cost efficient and less error prone for synthesizing shorter starting nucleic acids (e.g., on a chip). The first strategy also uses shorter universal primers (for amplifying the fragments) and thus further reduces costs. After restriction enzyme digestion, the end pieces to be removed from the central assembly fragments are also shorter and thus are easier, cheaper and faster to remove in the first strategy than the second.

Enzymatic digestions of DNA with type IIS or other site-specific restriction enzymes typically generate an overhang of four to six nucleotides. It is unexpectedly shown in this invention, that these short cohesive ends are sufficient for ligating multiple nucleic acid fragments containing complementary termini to form the target nucleic acid. Conventionally to ensure efficiency, a ligation reaction typically involves two fragments as ligation efficiency significantly decreases with three or more fragments. In addition, longer cohesive ends are required by conventional methods to improve specificity as mismatch often occurs. Furthermore, to select for the correct ligation product, a labor-intensive and time-consuming cloning and screening process is required.

The present invention provides for, among other things: (1) successful ligation of multiple fragments (e.g., at least 4, at least 5, at least 6, at least 7, at least 8, or more) in a single reaction (e.g. single pool); (2) quick and inexpensive ligation reaction (e.g., 30 minutes at room temperature); (3) high specificity which discriminates mismatches; and (4) quick PCR step to select the correct product, without requiring cloning and screening. Another advantage of the present invention is the ability to directly use synthetic oligonucleotides of commercially available chips or microarray to construct any target nucleic acid of interest, which can be of any sequence and/or any length (e.g., at least 500 bp, at least 1 kb, at least 2 kb, at least 5 kb, at least 10 kb, or longer). Such synthetic oligonucleotides can be of substantially the same size (e.g., about 50 bases, about 100 bases, about 200 bases, about 300 bases, or longer), and thus afford ease to handle.

In one example, assuming each oligonucleotide or fragment on the chip has a payload of 100 nucleotides and the fragments have 4-base overhangs, if the number of fragments is n, then ligation product length=(n*100)−(4*(n−1)), with (n−1) ligation junctions. It should be noted that to ensure ligation specificity, the overhangs can be selected or designed to be unique for each ligation site; that is, each pair of complementary overhangs for two fragments designed to be adjacent in an assembled product should be unique and differ from any other pair of complementary overhangs by at least one nucleotide.

Figure 10A:
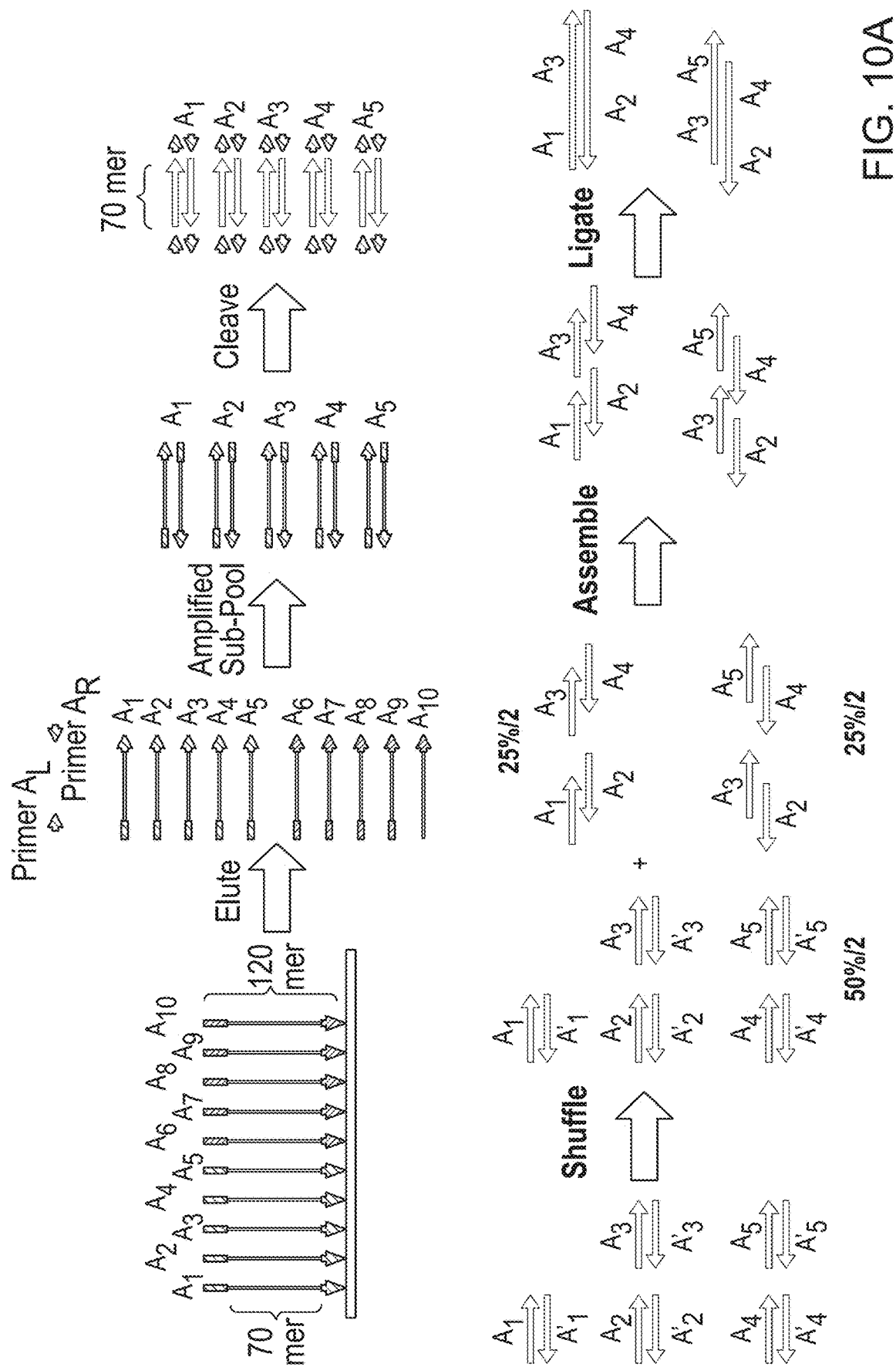
FIGS. 10A and 10B illustrate two offset assembly strategies.

Another strategy (offset assembly) for exposing cohesive ends is illustrated in FIG. 10A. Starting from a chip, a plurality of oligos (e.g., $A_1$-$A_{10}$) can be synthesized. The oligos can be designed to have central assembly sequences which when assembled properly, form the target nucleic acid 5'-$A_1$-$A_3$-$A_5$-$A_7$-$A_9$-3' (reverse strand being 3'-$A_2$-$A_4$-$A_6$-$A_8$-$A_{10}$-5'). That is, two adjacent oligonucleotides $A_n$ and $A_{n+1}$ can be designed to overlap. As used herein, adjacent oligonucleotides refers to oligonucleotides wherein a first oligonucleotide is at the 5' end or 3' end of a second oligonucleotide along the linear nucleic acid sequence. In some embodiments, adjacent oligonucleotides can be contiguous. As used herein, contiguous oligonucleotides refers to two oligonucleotides wherein the first oligonucleotide ends at position arbitrarily set at −1 and the second fragment starts at position arbitrarily set at 0 along the linear nucleic acid sequence. The central assembly sequences can be of any desirable length such as about 50-500 nucleotides, about 60-300 nucleotides, about 70-200 nucleotides, or shorter or longer. The plurality of oligos can have uniform length for ease of handling. By way of example, the synthesized oligos can also include amplification sequences at either end, which can have restriction sites built in. The amplification sequences can be about 10-30 nucleotides, about 15-25 nucleotides, or shorter or longer. FIG. 10A shows 70-mer central assembly sequences and 120-mer overall oligos. Synthesized oligos can be eluted, cleaved, or otherwise released from the chip, and subjected to PCR amplification using primer pair $A_L$ and $A_R$. Amplified products can be cleaved (e.g., with a restriction enzyme) to remove the amplification sequences (arrow heads), and the central 70-mer double-stranded assembly sequences can be purified therefrom. These double-stranded assembly sequences can then be melted (e.g., at 95° C.) and re-annealed (e.g., at 65° C.) in a single shuffling step. After shuffling of the single-stranded oligonucleotides, 25% of the products will be offset assembly products (e.g., $A_1/A_2$, $A_2/A_3$, $A_3/A_4$, $A4/A_5$, etc.) having cohesive ends. These cohesive ends can be assembled together (stepwise or in a single reaction hierarchically) using a ligase, thereby forming the target nucleic acid 5'-$A_1$-$A_3$-$A_5$-$A_7$-$A_9$-3' (reverse strand being 3'-$A_2$-$A_4$-$A_6$-$A_8$-$A_{10}$-5'). It should be appreciated that the oligos can also be designed such that the target nucleic acid is 5'-$A_1$ ... $A_3$ ... $A_5$ ... $A_7$ ... $A_9$-3' (i.e., gaps are allowed between $A_n$ and $A_{n+2}$, which can be filled using $A_{n+1}$ sequence as template). To that end, a polymerase and dNTPs can be used to extend and fill the gaps before ligation.

Figure 10B:
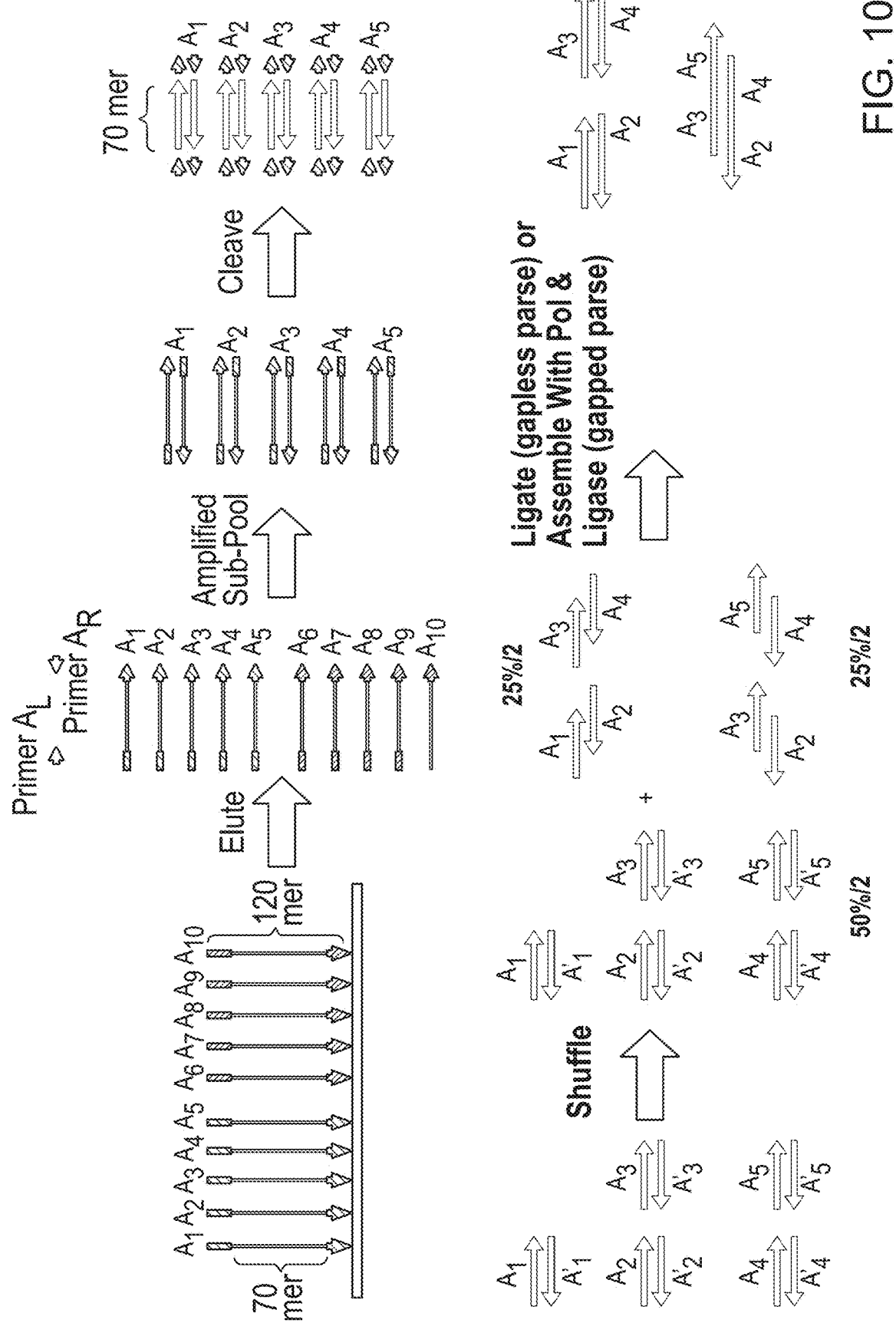

A second offset assembly strategy is illustrated in FIG. 10B, where a single combined assembly-(extension)-ligation step may be used, as opposed to two separate steps (i.e. assembly step and ligation step). For example, after the shuffling step (e.g., melting at 95° C. and re-annealing at 65° C.), gapless parse oligonucleotides can be ligated to form a full length product or a subassembly-product. If gaps are present in the parse, oligonucleotides can be incubated in presence of a polymerase and dNTPs to fill the gaps by chain extension prior to ligation. In some embodiments, the gapped parse can be subjected simultaneously to polymerase chain extension and ligation. As used herein the term "subassembly" refers to a nucleic acid molecule that has been assembled from a set of construction oligonucleotides. Preferably, a subassembly is at least about 2-fold, 3-fold, 4-fold, 5-fold, 10-fold, 20-fold, 50-fold, 100-fold, or more, longer than the construction oligonucleotides.

Other methods for generating cohesive ends can also be used. For example, a polymerase based method (e.g., T4 DNA polymerase) can be used to synthesize desirable cohesive ends. Regardless of the method of generating specific overhangs (e.g., complementary overhangs for nucleic acids designed to be adjacent in an assembled nucleic acid product), overhangs of different lengths may be designed and/or produced. In some embodiments, long single-stranded overhangs (3' or 5') may be used to promote specificity and/or efficient assembly. For example, a 3' or 5' single-stranded overhang may be longer than 8 bases long, e.g., 8-14, 14-20, 20-25, 25-50, 50-100, 100-500, or more bases long.

High Fidelity Assembly

According to aspects of the invention, a plurality of nucleic acid fragments may be assembled in a single procedure wherein the plurality of fragments is mixed together under conditions that promote covalent assembly of the fragments to generate a specific longer nucleic acid. According to aspects of the invention, a plurality of nucleic acid fragments may be covalently assembled in vitro using a ligase. In some embodiments, 5 or more (e.g., 10 or more, 15 or more, 15 to 20, 20 to 25, 25 to 30, 30 to 35, 35 to 40, 40 to 45, 45 to 50, 50 or more, etc.) different nucleic acid fragments may be assembled. However, it should be appreciated that any number of nucleic acids (e.g., 2, 3, 4, 5, 6, 7, 8, 9, 10, 11, 12, 13, 14, 15, 16, 17, 18, 19, 20, etc.) may be assembled using suitable assembly techniques. Each nucleic acid fragment being assembled may be between about 100 nucleotides long and about 1,000 nucleotides long (e.g., about 200, about 300, about 400, about 500, about 600, about 700, about 800, about 900). However, longer (e.g., about 2,500 or more nucleotides long, about 5,000 or more nucleotides long, about 7,500 or more nucleotides long, about 10,000 or more nucleotides long, etc.) or shorter nucleic acid fragments may be assembled using an assembly technique (e.g., shotgun assembly into a plasmid vector). It should be appreciated that the size of each nucleic acid fragment may be independent of the size of other nucleic acid fragments added to an assembly. However, in some embodiments, each nucleic acid fragment may be approximately the same size or length (e.g., between about 100 nucleotides long and about 400 nucleotides long). For example, the length of the oligonucleotides may have a median length of between about 100 nucleotides long and about 400 nucleotides long and vary from about, +/−1 nucleotides, +/−4 nucleotides, +/−10 nucleotides. It should be appreciated that the length of a double-stranded nucleic acid fragment may be indicated by the number of base pairs. As used herein, a nucleic acid fragment referred to as "x" nucleotides long corresponds to "x" base pairs in length when used in the context of a double-stranded nucleic acid fragment. In some embodiments, one or more nucleic acids being assembled in one reaction (e.g., 1-5, 5-10, 10-15, 15-20, etc.) may be codon-optimized and/or non-naturally occurring. In some embodiments, all of the nucleic acids being assembled in one reaction are codon-optimized and/or non-naturally occurring.

In some aspects of the invention, nucleic acid fragments being assembled are designed to have overlapping complementary sequences. In some embodiments, the nucleic acid fragments are double-stranded nucleic acid fragments with 3' and/or 5' single-stranded overhangs. These overhangs may be cohesive ends that can anneal to complementary cohesive ends on different nucleic acid fragments. According to aspects of the invention, the presence of complementary sequences (and particularly complementary cohesive ends) on two nucleic acid fragments promotes their covalent assembly. In some embodiments, a plurality of nucleic acid fragments with different overlapping complementary single-stranded cohesive ends are assembled and their order in the assembled nucleic acid product is determined by the identity of the cohesive ends on each fragment. For example, the nucleic acid fragments may be designed so that a first nucleic acid has a first cohesive end that is complementary to a first cohesive end of a second nucleic acid and a second cohesive end that is complementary to a first cohesive end of a third nucleic acid. A second cohesive end of the second nucleic acid may be complementary to a first cohesive end of a fourth nucleic acid. A second cohesive end of the third nucleic acid may be complementary a first cohesive end of a fifth nucleic acid. And so on through to the final nucleic acid. According to aspects of the invention, this technique may be used to generate a linear arrangement containing nucleic acid fragments assembled in a predetermined linear order (e.g., first, second, third, forth, . . . , final).

In certain embodiments, the overlapping complementary regions between adjacent nucleic acid fragments are designed (or selected) to be sufficiently different to promote (e.g., thermodynamically favor) assembly of a unique alignment of nucleic acid fragments (e.g., a selected or designed alignment of fragments). Surprisingly, under proper ligation conditions, difference by as little as one nucleotide affords sufficient discrimination power between perfect match (100% complementary cohesive ends) and mismatch (less than 100% complementary cohesive ends). As such, 4-base overhangs can allow up to $(4^4+1)=257$ different fragments to be ligated with high specificity and fidelity.

It should be appreciated that overlapping regions of different lengths may be used. In some embodiments, longer cohesive ends may be used when higher numbers of nucleic acid fragments are being assembled. Longer cohesive ends may provide more flexibility to design or select sufficiently distinct sequences to discriminate between correct cohesive end annealing (e.g., involving cohesive ends designed to anneal to each other) and incorrect cohesive end annealing (e.g., between non-complementary cohesive ends).

To achieve such high fidelity assembly, one or more suitable ligases may be used. A ligase may be obtained from recombinant or natural sources. In some embodiments, T3 DNA ligase, T4 DNA ligase, T7 DNA ligase, and/or E. coli DNA Ligase may be used. These ligases may be used at relatively low temperature (e.g., room temperature) and particularly useful for relatively short overhangs (e.g., about 3, about 4, about 5, or about 6 base overhangs). In certain ligation reactions (e.g., 30 min incubation at room temperature), T7 DNA ligase can be more efficient for multi-way ligation than the other ligases. A heat-stable ligase may also be used, such as one or more of Tth DNA ligase; Pfu DNA ligase; Taq ligase, any other suitable heat-stable ligase, or any combination thereof.

In some embodiments, two or more pairs of complementary cohesive ends between different nucleic acid fragments may be designed or selected to have identical or similar sequences in order to promote the assembly of products containing a relatively random arrangement (and/or number) of the fragments that have similar or identical cohesive ends. This may be useful to generate libraries of nucleic acid products with different sequence arrangements and/or different copy numbers of certain internal sequence regions.

One should appreciate that the variation in the concentration of individual fragments to be assembled might result into the assembly of incomplete intermediate constructs. For example, in the assembly of the target nucleic acid sequence (ABCDEF) using oligonucleotides A, B, C, D, E, F, each of which having the appropriate cohesive overhang end, if the concentration of the individual fragments is not equimolar (e.g if the concentration of A, B and C is greater than the concentration of D, E and F), terminating species (such as AB and BC) can be formed resulting in a mixture of unligated intermediate products. To avoid the formation of incomplete intermediate constructs, the target nucleic acid can be assembled from at least two pools of individual fragments (e.g. pool 1: A, C, E and Pool 2: B, D, F). In some embodiments, each of the two pools comprises a plurality of nucleic acid fragments, each nucleic acid fragment of the first pool having a terminal end complementary to a terminal end of a nucleic acid fragment in the second pool. In some embodiments, the at least two pools can be formed by splitting the population of oligonucleotides into the at least two pools and amplifying the oligonucleotides in each pool separately. In other embodiments, the at least two pools can be formed by releasing (e.g. by eluting, cleaving or amplifying) oligonucleotides from a first oligonucleotide array into a first pool and releasing the oligonucleotides of a second oligonucleotide array into a second pool. Yet in an other embodiment, the at least two different pools can be formed by amplifying oligonucleotide sequences using at least two different sets of amplification tags as described herein. By the way of example, the second pool comprising oligonucleotides B, D and F can be diluted such as the molar concentration of the oligonucleotides B, D, and F present in the second pool is lower than the molar concentration of oligonucleotides A, C, and E present in the first pool. For example, the molar concentration of the oligonucleotides in the second pool may be about two times, 10 times, 20 times, 50 times, 100 times or more lower than the molar concentration of the oligonucleotides in the first pool. After mixing and ligating the two pools, the resulting product comprises the target nucleic acid having the predetermined sequence and can be separated from the excess oligonucleotides form the first pool. In certain embodiments, it may be desirable to form pools of oligonucleotide dimers having different molar concentrations. For example, the assembly of the target nucleic acid sequences ABCDEFGH can be carried out using at least two different pools, the first pool comprising oligonucleotides A, B, E. F and the second pool comprising oligonucleotides C, D, G, H. The second pool can be diluted such that the molar concentration of oligonucleotides C, D, G, H is lower (e.g 10 times or 100 times) than the molar concentration of oligonucleotides A, B, E, F. Oligonucleotides having the appropriate cohesive overhang ends can be ligated to form the intermediate products AB and EF in the first pool and CD and GH in the second pool. Since the molar concentration of C, D, G, H is lower than the molar concentration of A, B, E. F, the molar concentration of CD and GH is lower than the molar concentration of AB and EF. After mixing the intermediates products AB, CD, EF, GH under ligating conditions, the resulting product comprising the target nucleic acid having the predetermined sequence can be separated from the excess dimers AB and EF.

In some embodiments, the nucleic acid fragments are mixed and incubated with a ligase. It should be appreciated that incubation under conditions that promote specific annealing of the cohesive ends may increase the frequency of assembly (e.g., correct assembly). In some embodiments, the different cohesive ends are designed to have similar melting temperatures (e.g., within about 5° C. of each other) so that correct annealing of all of the fragments is promoted under the same conditions. Correct annealing may be promoted at a different temperature depending on the length of the cohesive ends that are used. In some embodiments, cohesive ends of between about 4 and about 30 nucleotides in length (e.g., cohesive ends of about 5, about 10, about 15, about 20, about 25, or about 30 nucleotides in length) may be used. Incubation temperatures may range from about 20° C. to about 50° C. (including, e.g., room temperature). However, higher or lower temperatures may be used. The length of the incubation may be optimized based on the length of the overhangs, the complexity of the overhangs, and the number of different nucleic acids (and therefore the number of different overhangs) that are mixed together. The incubation time also may depend on the annealing temperature and the presence or absence of other agents in the mixture. For example, a nucleic acid binding protein and/or a recombinase may be added (e.g., RecA, for example a heat stable RecA protein).

The resulting complex of nucleic acids may be subjected to a polymerase chain reaction, in the presence of a pair of target-sequence specific primers, to amplify and select for the correct ligation product (i.e., the target nucleic acid). Alternatively, the resulting complex of nucleic acids can be ligated into a suitable vector and transformed into a host cell for further colony screening.

Sequence Analysis and Fragment Design and Selection

Aspects of the invention may include analyzing the sequence of a target nucleic acid and designing an assembly strategy based on the identification of regions, within the target nucleic acid sequence, that can be used to generate appropriate cohesive ends (e.g., single-stranded overhangs). These regions may be used to define the ends of nucleic acid fragments that can be assembled (e.g., in one reaction) to generate the target nucleic acid. The nucleic acid fragments can then be provided or made (e.g., in a multiplex assembly reaction). The nucleic acid fragments can be selected such that they have a relative uniform size for ease to handle (e.g., purification).

According to some embodiments, the nucleic acid sequence can be designed and/or analyzed in a computer-assisted manner to generate a set of parsed double-stranded or single-stranded oligonucleotides. As used herein, the term "parsed" means that a sequence of target nucleic acid has been delineated, for example in a computer-assisted manner, such as to identify a series of adjacent oligonucleotide sequences. Adjacent oligonucleotides or nucleic acid fragments preferably overlap by an appropriate number of nucleotides to facilitate assembly according the methods of the invention. The oligonucleotide sequences can be individually synthesized and assembled using the methods of the invention.

In some embodiments, a target nucleic acid sequence may be analyzed to identify regions that contain at least one different nucleotide on one strand of the target nucleic acid. These regions may be used to generate cohesive ends. It should be appreciated that the length of a cohesive end is preferably sufficient to provide specificity. For example, cohesive ends may be long enough to have sufficiently different sequences (e.g., at least 1-base differences) to prevent or reduce mispairing between similar cohesive ends. However, their length is preferably not long enough to stabilize mispairs between similar cohesive sequences. In some embodiments, a length of about 3 to about 10 bases may be used. However, any suitable length may be selected for a region that is to be used to generate a cohesive overhang. The importance of specificity may depend on the number of different fragments that are being assembled simultaneously. Also, the appropriate length required to avoid stabilizing mispaired regions may depend on the conditions used for annealing different cohesive ends.

In some embodiments, alternating regions may be selected if they are separated by distances that define fragments with suitable lengths for the assembly design. In some embodiments, the alternating regions may be separated by about 100 to about 500 bases. However, any suitable shorter or longer distance may be selected. For example, the cohesive regions may be separated by about 200 to about 1,000 bases. It should be appreciated that different patterns of alternating regions may be available depending on several factors (e.g., depending on the sequence of the target nucleic acid, the chosen length of the cohesive ends, and the desired fragment length). In some embodiments, if several options are available, the regions may be selected to maximize the sequence differences between different cohesive ends.

Selection of the cohesive regions defines the fragments that will be assembled to generate the target nucleic acid. Accordingly, the fragment size may be between about 100 and about 500 base pairs long, between about 200 and about 1,000 bases long, or shorter or longer depending on the target nucleic acid. The fragments may be generated or obtained using any suitable technique. In some embodiments, each fragment may be assembled (e.g., in a multiplex duplex assembly reaction) so that it is flanked by double-stranded regions that can be used to generate the cohesive single-stranded regions.

In some embodiments, methods for enabling the assembly of a target polynucleotide based upon information of the sequence of the target nucleic acid. In some embodiments, a computer software can be used to parse the target sequence (e.g. $A_1$-$A_n$) breaking it down into a set of overlapping oligonucleotides ($A_1$, $A_2$, $A_3$, . . . $A_n$) of specified length. Oligos $A_1$, $A_2$, $A_3$, . . . $A_n$ can be synthesized from a chip or microarray. In some embodiments, the oligonucleotide sequences can may be designed to include: amplification primer sequence, recognition site for a restriction enzyme, such as a type IIS restriction enzyme, padding, payload, padding, reverse complement of the recognition site for a restriction enzyme (same or different), reverse complement of a different amplification primer sequence. The payload can be an overlapping subset of the target gene (or any arbitrary nucleic acid sequence). The payload can be padded, if desired, with m nucleotides M ($M_m$) to allow the generation of a uniquely complementary cohesive ends after cleavage with the restriction enzyme(s). The primers allow amplification. The recognition sites for the restriction enzyme(s) allow the primers to be cleaved off from the payload.

In certain embodiments, it is advantageous to use the same recognition site across multiple target sequences. However, it should be noted that if a target sequence already contains the recognition site, then the oligo which contains that recognition site (in a left-to-right or right-to-left parse) will be cut, preventing correct assembly. In some embodiments, if the target sequence only contains a single occurrence of the recognition site, the problem can be solved by starting the parse within the site, and parsing one set of oligos to the left, and the other set to the right of the recognition site. Since the site will be split between 2 oligos, it will not exist as an intact sequence and thus will not be recognized or cut. If there is a desired oligo length or range of lengths, the last oligo in each side of the parse can be padded with an appropriate number m of nucleotides M ($M_m$).

This approach can be extended to more than one occurrence of a recognition site if those restriction sites appear within an integer multiple of the allowed length range for a payload. As an example of the simplest case (and ignoring any desired overlap for purposes of this example), if any portion of 2 restriction sites are exactly 100 bp apart for a desired 100 bp payload size, then parsing from within either one will automatically split the other. If the payload can vary from 90-110 bp, then a pair of restriction sites within this distance range can be accommodated. With this same payload range, a pair could also be split at longer distances: 180-220 bp, 270-330 bp, etc.

When parsing a target sequence into oligos, the length of the last oligo (or last in each direction if parsing from the interior) may fall outside the desired range of oligo lengths. The last oligo can be padded to the desired length. This may come however at the cost of producing additional base pairs that are otherwise not useful, specially when a large number of target sequences are assembled. In some embodiments, a solution to this problem is to concatenate every target sequence into a single long pseudo-target (with optional primer sequences between the actual target sequences), and then split into smaller, overlapping fragments of the desired length (e.g., by cleavage or amplification by PCR). The computation of the length of a fragment is presented below:

length=(pieces*max_oligo_length)−
(junctions*overlap)

where junctions=pieces−1

For example:

length 484=(pieces 5*max_oligo_length 100)−(junctions 4*overlap 4)

length 504=(pieces 5*max_oligo_length 104)−(junctions 4*overlap 4)

If some of the target sequences contain a restriction site, then in some cases, the order in which the target sequences are concatenated can be chosen such as to have the restriction site at a junction (and within the desired oligo length range). In the general case, additional padding can be added just to the subset of target sequences that contain the restriction site, still yielding the full benefit of eliminating the padding on the majority of target sequences.

Examples of the present invention show that certain ligase enzymes in certain conditions correctly distinguishing 2 oligos with overhangs having the same last base and different second-to-last base. In some embodiments, it may be desirable to design the oligos such that the last base in each overhang is unique. Unique A, C, G, T at the end (4 junctions) allow ligation of up to 5 pieces, which is a commercially useful number to assemble. Larger numbers of ligation pieces are also contemplated in the present invention, as exemplified below:

last 2 bases unique: $4^2=16$ junctions, up to 17 pieces
last 3 bases unique: $4^3=64$ junctions, up to 65 pieces
last 4 bases unique: $4^4=256$ junctions, up to 257 pieces Aspects of the invention relate to algorithms to parse the input target nucleic acid sequence. In some embodiments, algorithms can be used to ensure that the last base (or last 2, 3 or 4 bases) of the plurality of oligos is unique. For example, algorithms of the invention can be used to define a plurality of parsed oligonucleotides that together comprise the target sequence (naturally occurring, non-naturally occurring, or any arbitrary nucleic acid sequence, the oligonucleotides having approximately the same length and with a 4 base overlap the last base (or last 2, 3 or 4 bases) being unique. Yet in some embodiments, the oligonucleotides can be defined such as the second-to-last or third-to-last, etc or combinations thereof is unique.

In some embodiments, a first algorithm comprises the following design or decomposition steps:

Step 1: is to move over by the target amount, e.g. 100 bp,
Step 2: store the relevant 1-4 bases in a set (e.g., in a memory),
Step 3: back up by the overlap (4 bp),
Step 4: move again. For this second and each subsequent move by 100 bp, if the relevant 1-4 bases already exist in the set, then shift over 1 base at a time until encountering a 1-4 base sequence that is not yet in the set.
Step 5: add the new 1-4 base sequence to the set,
Step 6: then repeat. If the desired number of pieces is reached before reaching the end of the DNA sequence, then start over with a new set, backing up by an appropriate overlap for assembly of fragments (which may or may not be a different method than assembly of oligos into a fragment).

One skilled in the art will note that the 1-base shift could vary in direction, e.g., always left (shorter) if the nominal length is a maximum desired length, always right (longer) if the nominal length is a minimum desired length, or some combination thereof. To center around the nominal length, the shift could alternate, e.g., check positions in the following order: −1, +1, −2, +2, etc. The shift could also be weighted to prefer, for example, shorter but allow longer, e.g., −1, −2, +1, −3, −4, +2, etc.

This algorithm may be limited to design of certain target sequences, as the required shift may be large since the degrees of freedom are reduced with each subsequent addition to the set. For example, the first end may be an "A", but the last end may not have an "A" either within several bases, thus making the last oligo very short or very long, which may be undesirable. One solution to this problem is to store an array of data for each junction, then choose either the fewest number of oligos to shift, or the least total shift distance among all oligos, or some combination thereof.

The statistics for how often any given short sequence (e.g. for a restriction site) will appear in a random 1,000 bp sequence is as follows. For example, if a 6-bp restriction site is used which does not parse from the middle of a target sequence, then 22% of sequences could not be built with that restriction site. With the same 6-bp site and parsing from the middle, only the 3% of sequences that contain 2 sites could not be built (or would require additional parsing). More particularly:

If a single occurrence a restriction site prevented building:
   With quantity 1 of length 5 bp, 62% will have at least 1 site
   With quantity 1 of length 6 bp, 22% will have at least 1 site
   With quantity 1 of length 7 bp, 6% will have at least 1 site
If parsing from the interior allows 2 occurrences:
   With quantity 1 of length 5 bp, 25% will have at least 2 sites
   With quantity 1 of length 6 bp, 3% will have at least 2 sites
   With quantity 1 of length 7 bp, <1% will have at least 2 sites (about 0.2%)
If more than one restriction enzyme (and corresponding site) is used and if allowing a single occurrence:
   With quantity 2 of length 5 bp, 38% will have at least 1 site
   With quantity 2 of length 6 bp, 5% will have at least 1 site
   With length 7 bp and length 6 bp, 1% will have at least 1 site
   With quantity 3 of length 5 bp, 24% will have at least 1 site
   With quantity 3 of length 6 bp, 1% will have at least 1 site
If more than one restriction enzyme, allowing 2 occurrences:
   With quantity 2 of length 5 bp, 6% will have at least 2 sites
   With quantity 2 of length 6 bp, <1% will have at least 2 sites (about 0.06%)
   With quantity 3 of length 5 bp, 2% will have at least 2 sites.

Applications

Aspects of the invention may be useful for a range of applications involving the production and/or use of synthetic nucleic acids. As described herein, the invention provides methods for assembling synthetic nucleic acids with increased efficiency. The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

Many of the techniques described herein can be used together, applying suitable assembly techniques at one or more points to produce long nucleic acid molecules. For example, ligase-based assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Any of the nucleic acid products (e.g., including nucleic acids that are amplified, cloned, purified, isolated, etc.) may be packaged in any suitable format (e.g., in a stable buffer, lyophilized, etc.) for storage and/or shipping (e.g., for shipping to a distribution center or to a customer). Similarly, any of the host cells (e.g., cells transformed with a vector or having a modified genome) may be prepared in a suitable buffer for storage and or transport (e.g., for distribution to a customer). In some embodiments, cells may be frozen. However, other stable cell preparations also may be used.

Host cells may be grown and expanded in culture. Host cells may be used for expressing one or more RNAs or polypeptides of interest (e.g., therapeutic, industrial, agricultural, and/or medical proteins). The expressed polypeptides may be natural polypeptides or non-natural polypeptides. The polypeptides may be isolated or purified for subsequent use.

Accordingly, nucleic acid molecules generated using methods of the invention can be incorporated into a vector. The vector may be a cloning vector or an expression vector. In some embodiments, the vector may be a viral vector. A viral vector may comprise nucleic acid sequences capable of infecting target cells. Similarly, in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e. using cell-free systems) or in vivo (i.e. expressed in cells). In some embodiments, cell lysates may be prepared. In certain embodiments, expressed RNAs or polypeptides may be isolated or purified. Nucleic acids of the invention also may be used to add detection and/or purification tags to expressed polypeptides or fragments thereof. Examples of polypeptide-based fusion/tag include, but are not limited to, hexa-histidine (His$^6$) Myc and HA, and other polypeptides with utility, such as GFP$_5$ GST, MBP, chitin and the like. In some embodiments, polypeptides may comprise one or more unnatural amino acid residue(s).

In some embodiments, antibodies can be made against polypeptides or fragment(s) thereof encoded by one or more synthetic nucleic acids. In certain embodiments, synthetic nucleic acids may be provided as libraries for screening in research and development (e.g., to identify potential therapeutic proteins or peptides, to identify potential protein targets for drug development, etc.) In some embodiments, a synthetic nucleic acid may be used as a therapeutic (e.g., for gene therapy, or for gene regulation). For example, a synthetic nucleic acid may be administered to a patient in an amount sufficient to express a therapeutic amount of a protein. In other embodiments, a synthetic nucleic acid may be administered to a patient in an amount sufficient to regulate (e.g., down-regulate) the expression of a gene.

It should be appreciated that different acts or embodiments described herein may be performed independently and may be performed at different locations in the United States or outside the United States. For example, each of the acts of receiving an order for a target nucleic acid, analyzing a target nucleic acid sequence, designing one or more starting nucleic acids (e.g., oligonucleotides), synthesizing starting nucleic acid(s), purifying starting nucleic acid(s), assembling starting nucleic acid(s), isolating assembled nucleic acid(s), confirming the sequence of assembled nucleic acid(s), manipulating assembled nucleic acid(s) (e.g., amplifying, cloning, inserting into a host genome, etc.), and any other acts or any parts of these acts may be performed independently either at one location or at different sites within the United States or outside the United States. In some embodiments, an assembly procedure may involve a combination of acts that are performed at one site (in the United States or outside the United States) and acts that are performed at one or more remote sites (within the United States or outside the United States).

Automated Applications

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Figure 1B:
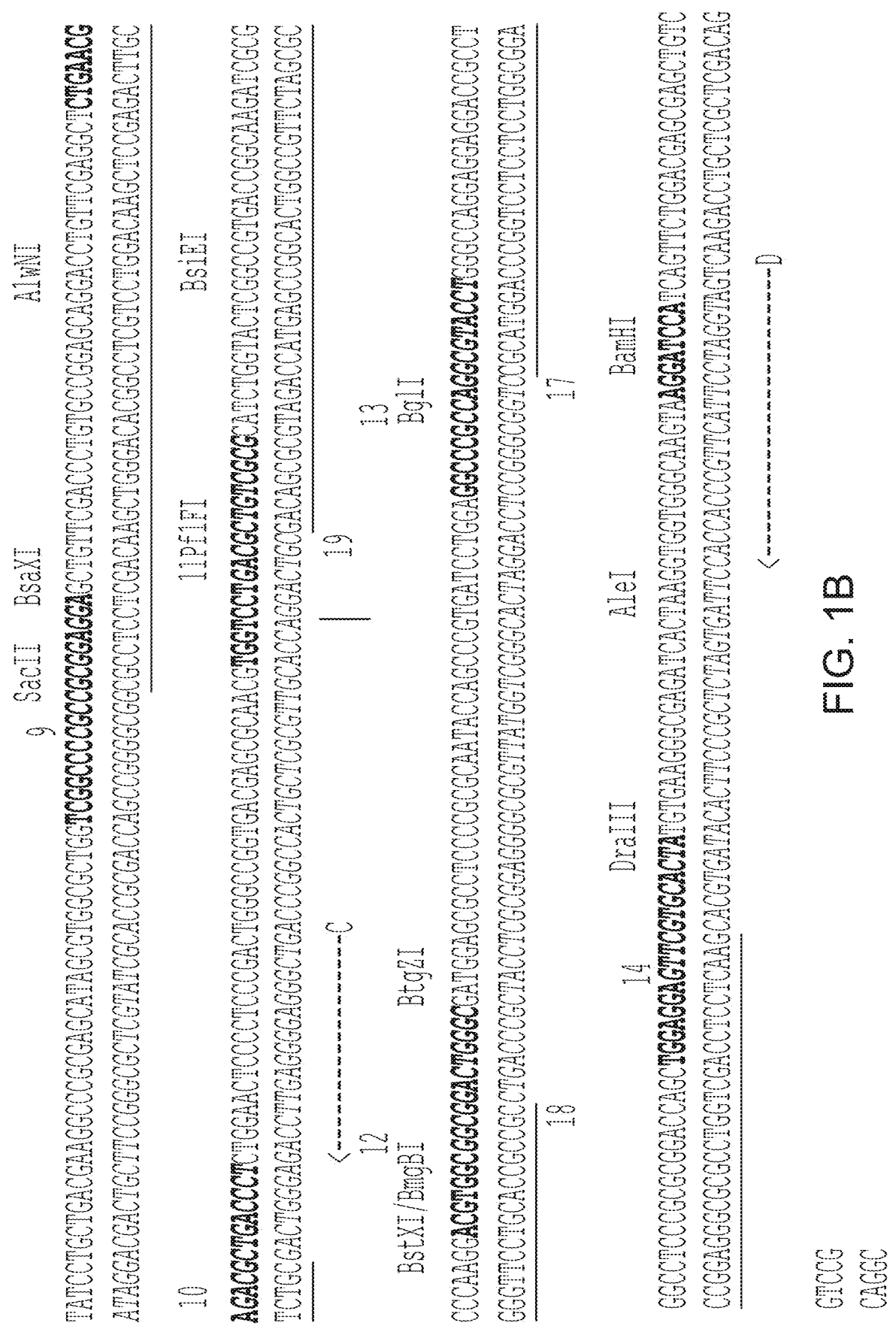

FIGS. 1A and 1B show the sequence of an arbitrarily chosen, double-stranded sequence of about 836 bp long. 60-bp fragments were selected and labeled 1 to 28 (fragments 1-14 are on the positive strand; fragments 15-28 on the negative strand). These 60-bp fragments were ordered from IDT (Integrated DNA Technologies, Coralville, Iowa)

("IDT oligos"), with the following flanking sequences (SEQ ID NO: 1 (left) and SEQ ID NO: 2 (right)):

GTCACTACCGCTATCATGGCGGTCTC. . . . .GAGACCAGGAGAC-
AGGACCGACCAAA

CAGTGATGGCGATAGTACCGCCAGAG. . . . .CTCTGGTCCTCTG-
TCCTGGCTGGTTT

Underlined is the recognition site of BsaI-HF, which produces a 4-base overhang:

(SEQ ID NO: 9)
        5'...G G T C T C (N)$_{1\blacktriangledown}$..3'

3'...C C A G A G (N)$_{5\blacktriangle}$...5'

The BsaI-HF recognition sites are flanked by universal primers which are useful for amplification of these fragments.

PCR primers A-E were also designed (dashed arrows in FIGS. 1A and 1B) for amplifying the correct ligation product. FIG. 2 shows the relative position of the primers ("oligoA" to "oligoE") as arrowheads, as well as the predicted size of corresponding corresponding PCR products.

Double-stranded IDT oligos were subject to BsaI-HF digestion, under the following conditions:
1×NEBuffer 4
Supplemented with 100 μg/ml Bovine Serum Albumin
Incubate at 37° C.

Figure 3:
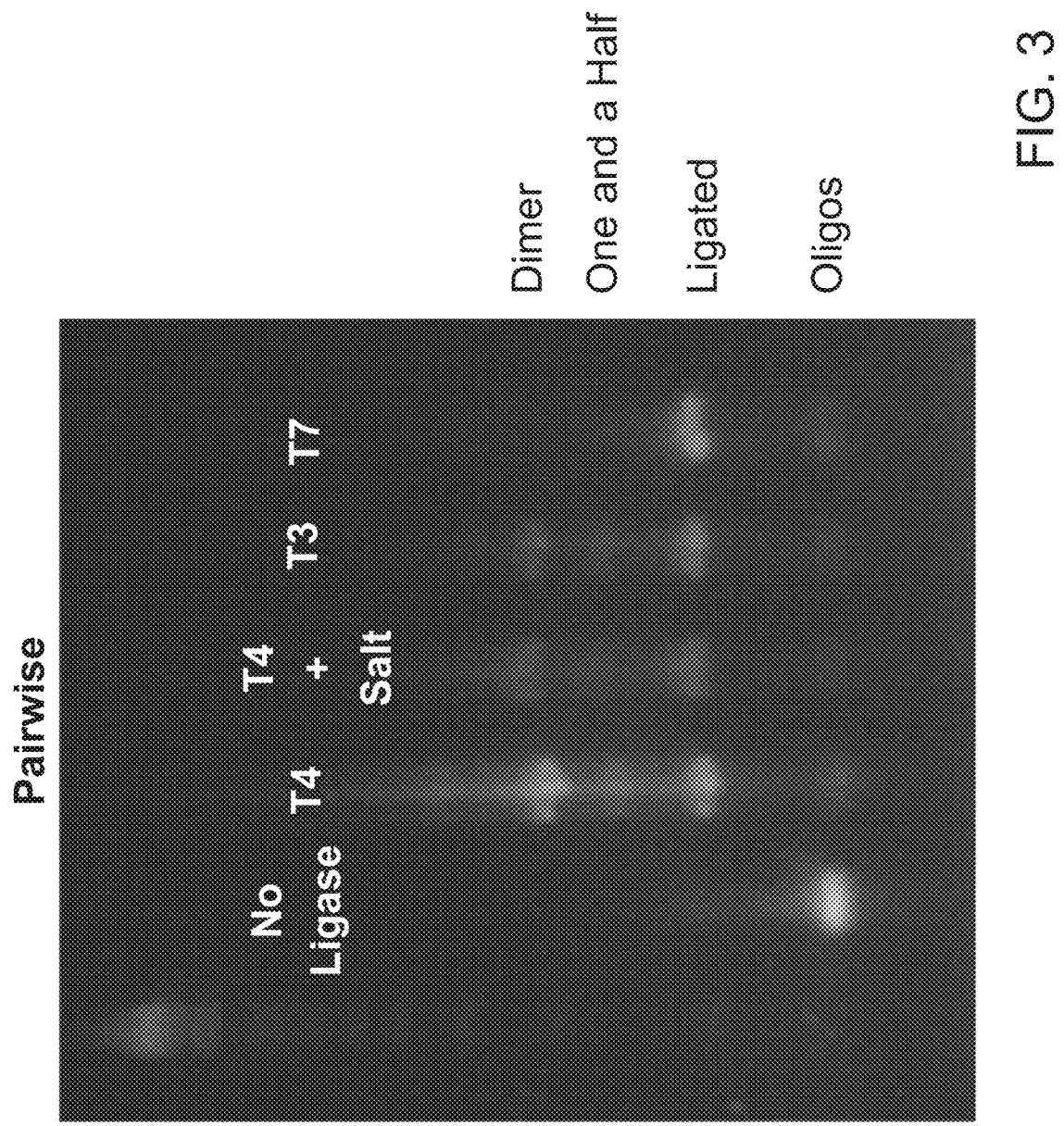
FIG. 3 illustrates an embodiment of a pairwise oligonucleotide assembly reaction.
Figure 4:
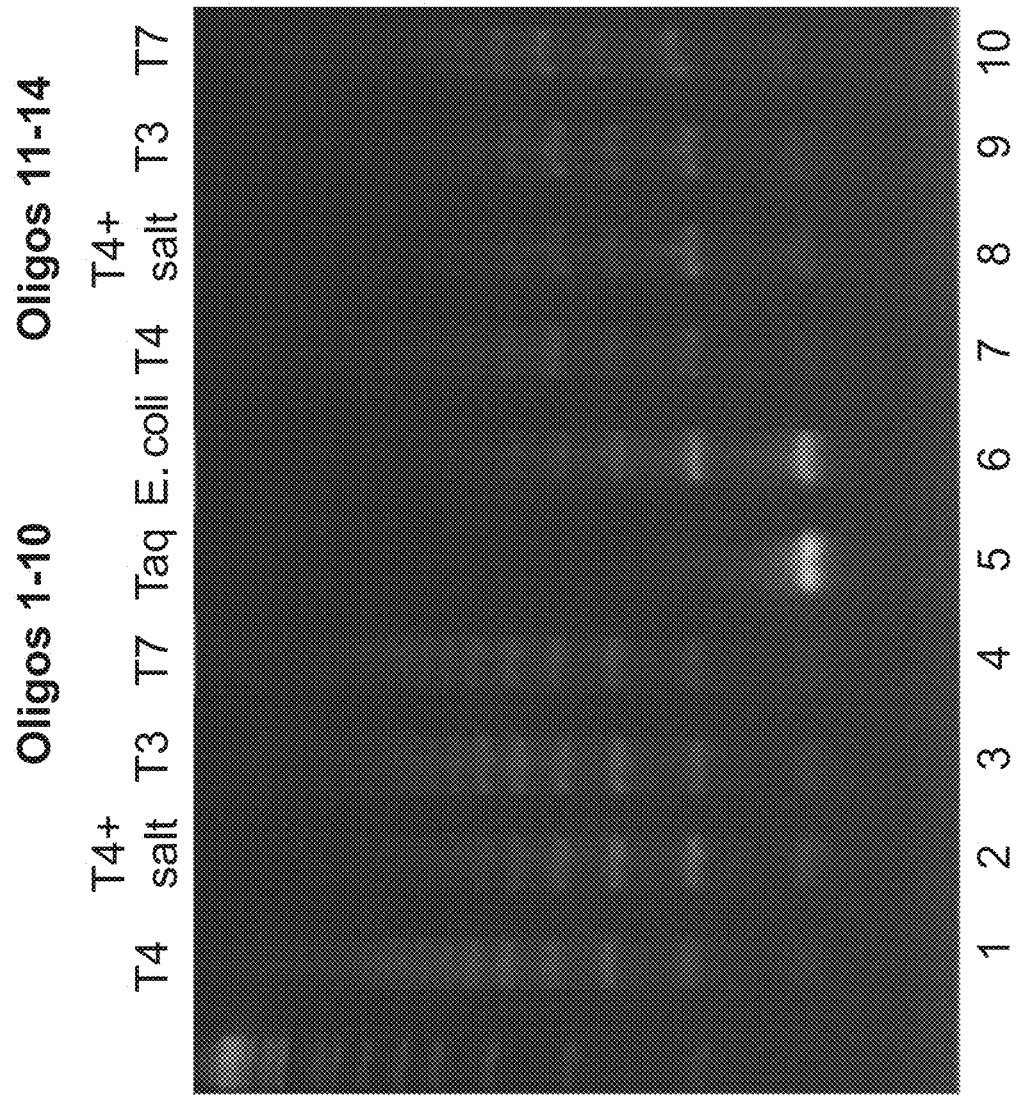
FIG. 4 illustrates embodiments of a multiplex oligonucleotide assembly reaction.
Figure 5:
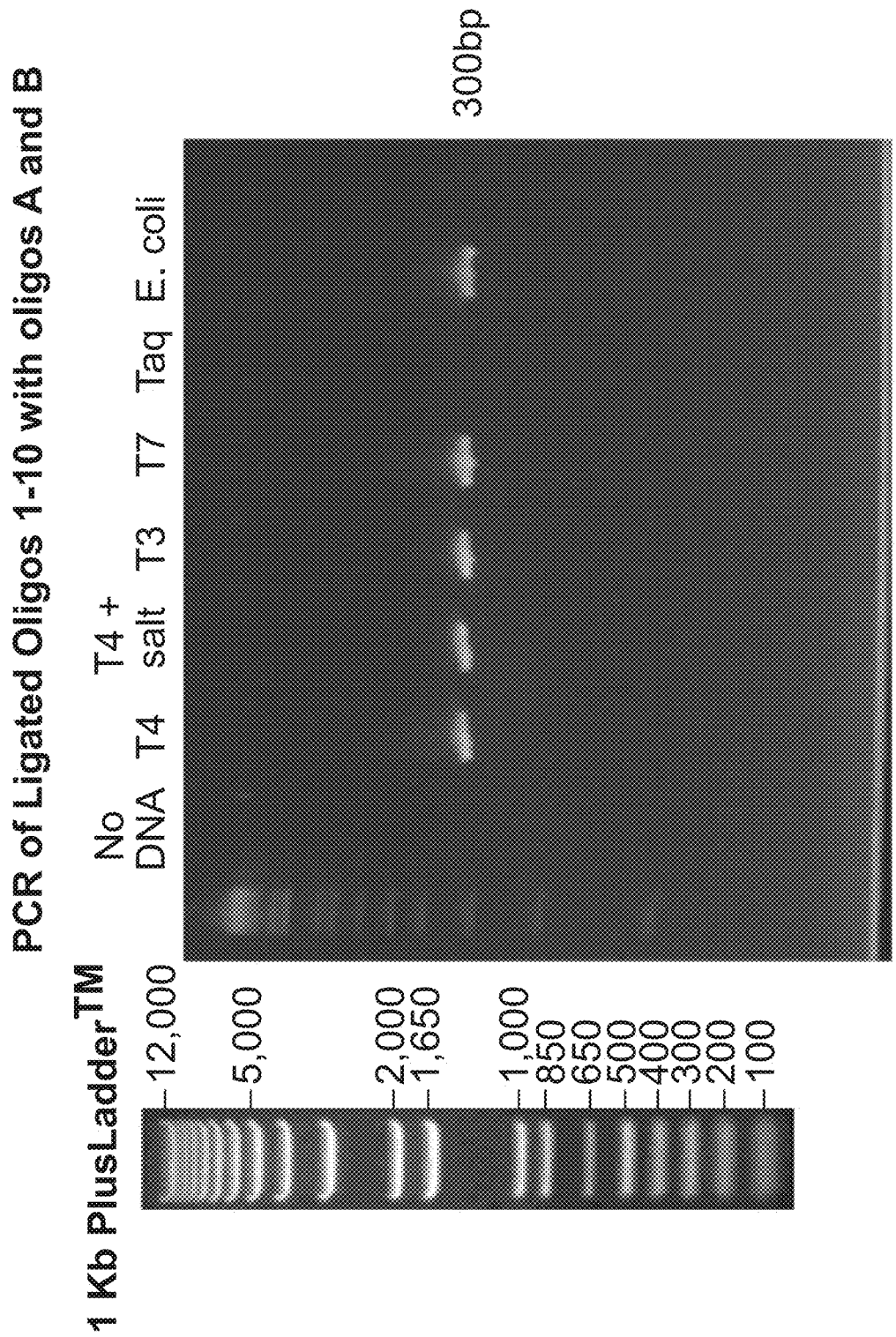
FIG. 5 illustrates a PCR based test of the products of the multiplex oligonucleotide assembly reaction of FIG. 4.

Digested double strand oligos having cohesive ends (oligos 1-28) were purified by electrophoresis on a 4% gel. Various combinations of purified oligos 1-28 were then subject to ligation reactions. Several different ligases, temperatures and incubation times were tested for optimal ligation conditions. Ligases tested include:
T4 DNA Ligase
T4 DNA Ligase+300 mM salt (for reduced activity, higher specificity)
T3 DNA Ligase
T7 DNA Ligase
Pfu DNA Ligase
Taq DNA Ligase
E. coli DNA Ligase Exemplary results conducted at room temperature for 30 minutes are shown in FIGS. 3-5. FIG. 3 shows the electrophoresis results of pairwise ligation (of two oligos), from left to right of the gel: ladder, no ligase, T4 DNA ligase, T4 DNA ligase+salt, T3 DNA ligase, T7 DNA ligase. The bands from bottom to top of gel correspond to: free oligos, correct ligated product, one and a half ligated product, dimer of ligated product. T7 DNA ligase produced the most correct ligated product and thus appeared the most efficient under this experimental condition, other things being equal.

FIG. 4 shows the ligation results of oligos 1-10 (lanes 1-6) and oligos 11-14 (lanes 7-10), with different ligases indicated at the top of the gel. Multiple bands were observed, indicating the presence of different ligation products. However, upon PCR amplification using oligos A and B as primers, a strong band at about 300 bp was observed. Because the predicted PCR product from oligos A and B is 337 bp (see FIG. 2), this band corresponds to the correct ligation product comprising oligos 1-6 (see FIGS. 1A and 1B). The band was cut from the gel, purified, and sequenced. The sequencing results are shown in FIG. 6, confirming 100% fidelity of the ligation product (SEQ ID NO: 4) as compared to the expected sequence. Taq DNA ligase did not produce any ligation product, probably because of the low reaction temperature (room temperature), as Taq DNA ligase is only active at elevated temperatures (45° C.-65° C.).

Figure 7A:
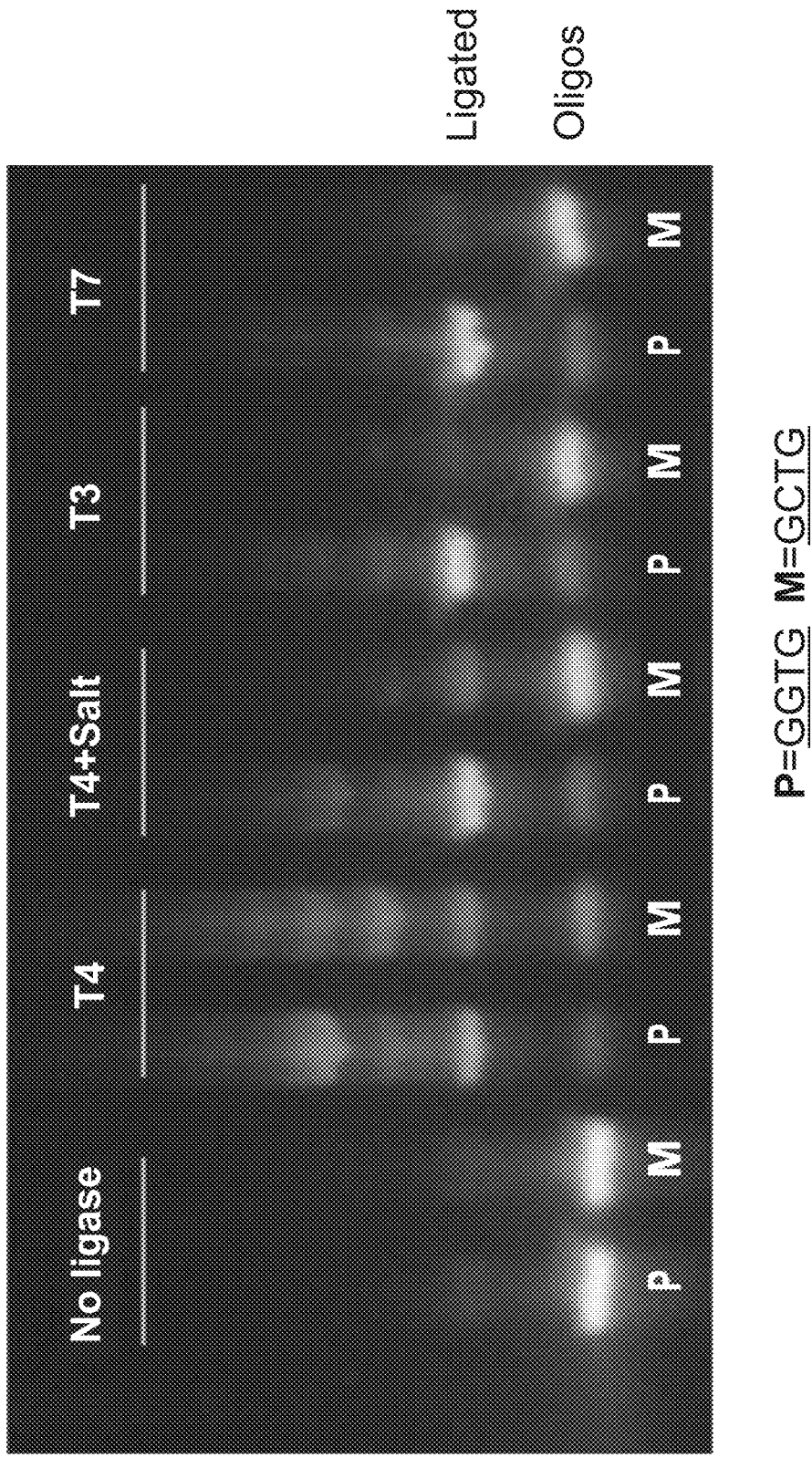
FIGS. 7A and 7B illustrate embodiments of a pairwise mismatch ligation assay.
Figure 7B:
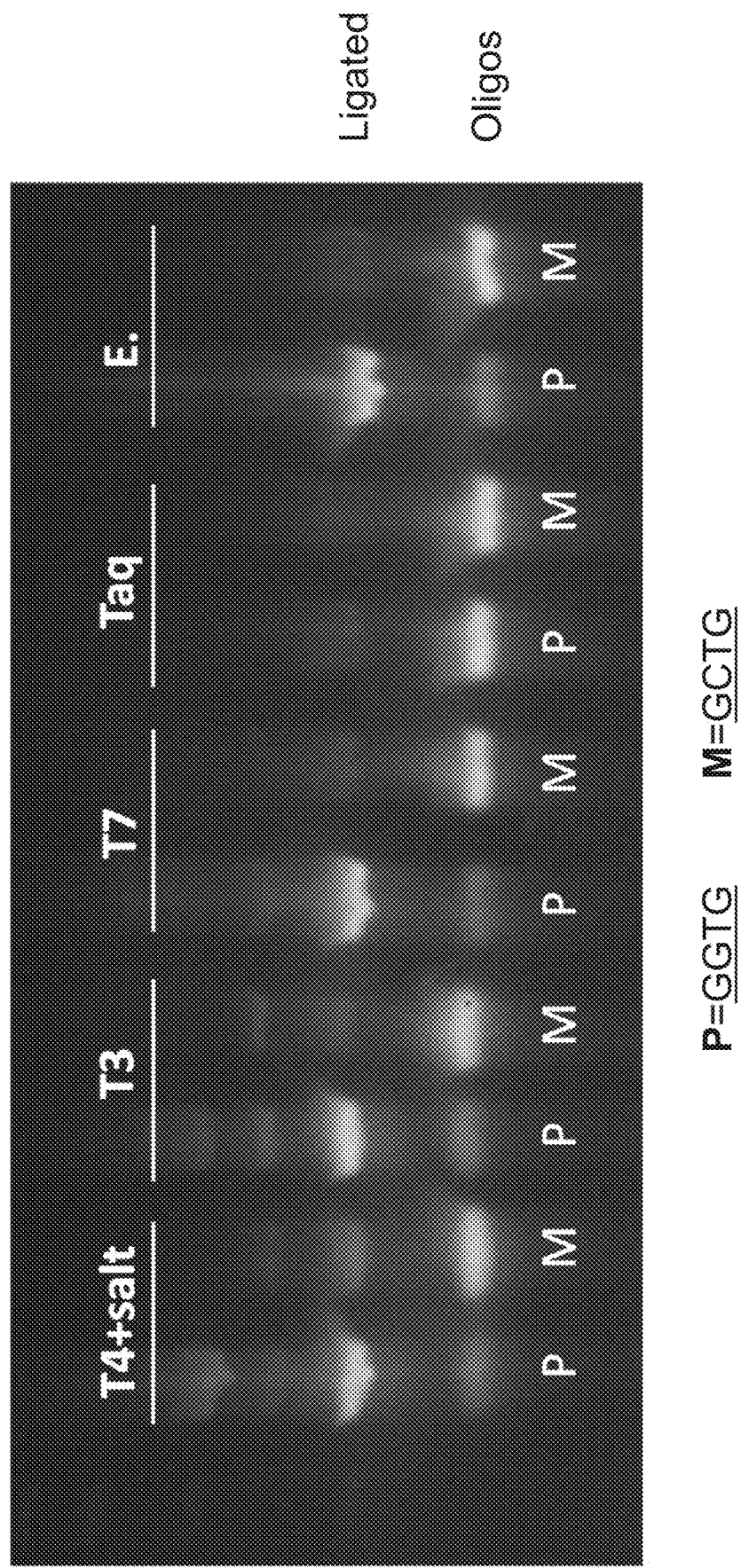

A pairwise mismatch assay was developed to test the specificity of various ligases. A pair of oligos were designed with 4-base overhangs, where the perfect match ("P") sequence is GGTG and the mismatch ("M") sequence is GCTG which differs from the correct sequence by one nucleotide. As shown in FIGS. 7A and 7B, two major bands can be observed, with the lower band corresponding to unligated oligos (as indicated by the no ligase controls), and the upper band corresponding to ligated product. T4 DNA ligase+salt, T3 DNA ligase, T7 DNA ligase, and E. coli DNA ligase all produced a strong band corresponding to the ligated product when using the perfect match overhangs. By contrast, when mismatch overhangs were used, majority of the product was unligated oligos. These experiment show that under these reaction conditions, T4 DNA ligase+salt, T3 DNA ligase, T7 DNA ligase, and E. coli DNA ligase all demonstrated high specificity and discrimination of mismatch as little as one nucleotide difference.

In addition to the ligation product having oligos 1-6 shown above, other ligation products were also produced, including longer products. One product appeared to have oligos 1-6 ligated to oligo 14. This is due to the fact that oligos 7 and 14 had the same cohesive end (GTTC, boxes in FIGS. 8A and 8B).

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference.

What is claimed is:

1. A method of assembling a polynucleotide, comprising:
(a) providing a plurality of blunt-end double-stranded nucleic acid fragments comprising a plurality of sequences, each fragment comprising a restriction enzyme recognition sequence at one end and/or both ends;
(b) enzymatically digesting the plurality of blunt-end double-stranded nucleic acid fragments to produce a plurality of digested double-stranded nucleic acid fragments comprising a combination of at least 4 fragments that together forms the sequence of one copy of the polynucleotide, each fragment in the combination having at least one overhang, wherein each overhang in the combination:
(i) has a length of 4 nucleotides;
(ii) has a sequence that is different from every other overhang in the combination; and
(iii) is complementary to exactly one other overhang in the combination;

(c) annealing the overhangs of the digested double-stranded nucleic acid fragments in the combination of at least 4 fragments that together forms the sequence of one copy of the polynucleotide; and (d) ligating, in a single step, the annealed double-stranded nucleic acid fragments using a ligase, thereby assembling the polynucleotide.

2. The method of claim 1, wherein the plurality of blunt-end double-stranded nucleic acid fragments are produced by amplification from a plurality of single-stranded oligonucleotides using a universal primer, wherein each single-stranded oligonucleotide comprises a universal primer binding site at the 3' end and the 5' end that is complementary to the universal primer.

3. The method of claim 2, wherein the plurality of single-stranded oligonucleotides have been immobilized on a solid support.

4. The method of claim 2, wherein the restriction enzyme recognition sequence overlaps with the universal primer binding site and is located at the 5' or 3' end of the universal primer binding site.

5. The method of claim 2, wherein the universal primer has an affinity tag.

6. The method of claim 5, wherein the affinity tag is biotin.

7. The method of claim 1, wherein the plurality of blunt-end double-stranded nucleic acid fragments comprises at least 4 different blunt-end double-stranded nucleic acid fragments.

8. The method of claim 1, wherein each nucleic acid fragment of the plurality of blunt-end double-stranded nucleic acid fragments is at least 50 bases long.

9. The method of claim 1, wherein the restriction enzyme recognition sequence is the same for all blunt-end double-stranded nucleic acid fragments.

10. The method of claim 1, wherein at least one nucleic acid fragment of the plurality of blunt-end double-stranded nucleic acid fragments comprises at least two different restriction enzyme recognition sequences.

11. The method of claim 10, wherein the at least two different restriction enzyme recognition sequences are recognizable by two different restriction enzymes that produce overhangs having the same number of bases.

12. The method of claim 1, wherein the restriction enzyme recognition sequence is a type IIs restriction enzyme recognition sequence.

13. The method of claim 12, wherein the restriction enzyme that recognizes the type IIs restriction enzyme recognition sequence is BsaI, BsmBI, BtgZI, BsmFI, FokI, AarI, or BbvI.

14. The method of claim 1, further comprising purifying the digested double-stranded nucleic acid fragments to remove enzymatic digestion products that are less than 20 bases long.

15. The method of claim 14, wherein the purifying comprises separation by differential affinity to silica, size filtration, differential precipitation with polyethylene glycol or cetyltrimethylammonium bromide, or any combination thereof.

16. The method of claim 1, wherein the ligase is T3 DNA ligase, T4 DNA ligase, T7 DNA ligase, or *E. coli* DNA ligase.

17. The method of claim 1, wherein the polynucleotide is a non-naturally occurring nucleic acid sequence.

18. The method of claim 1, wherein the polynucleotide is at least 500 bases long.

19. The method of claim 1, further comprising amplifying the polynucleotide using primers complementary to the 3' and 5' ends of the polynucleotide sequence.

20. The method of claim 1, further comprising sequencing the polynucleotide.

21. The method of claim 3, wherein the solid support is an array, a bead or a nanoparticle.

22. The method of claim 2, wherein the plurality of single-stranded oligonucleotides are error-free.

* * * * *

SEQUENCE LISTING

<160> NUMBER OF SEQ ID NOS: 9

<210> SEQ ID NO 1
<211> LENGTH: 26
<212> TYPE: DNA

```
<213> ORGANISM: Artificial Sequence
<220> FEATURE:
<223> OTHER INFORMATION: Synthetic construct

<400> SEQUENCE: 1
gtcactaccg ctatcatggc ggtctc                                          26

<210> SEQ ID NO 2
<211> LENGTH: 26
<212> TYPE: DNA
<213> ORGANISM: Artificial Sequence
<220> FEATURE:
<223> OTHER INFORMATION: Synthetic construct

<400> SEQUENCE: 2
gagaccagga gacaggaccg accaaa                                          26

<210> SEQ ID NO 3
<211> LENGTH: 861
<212> TYPE: DNA
<213> ORGANISM: Artificial Sequence
<220> FEATURE:
<223> OTHER INFORMATION: Synthetic construct

<400> SEQUENCE: 3
ggagggttgc gtttgagacg ggcgacagat catatgcggg aggcggtgat cgccgaggtg     60
agcacgcagc tgtccgaggt ggtgggcgtc atcgagcgcc acctggagcc gacgctgctg    120
gccgtccacc tgtacggcag cgccgtggac ggcggcctga agcctcactc cgacatcgat    180
ctgctggtga cggtgaccgt ccgcctggac gagactactc gccgcgctct gatcaacgac    240
ctgctggaga cgtccgcctc ccccggggag agcgagatcc tccgggctgt ggaggtgacc    300
atcgtggtga cgacgacat catcccttgg cgctaccccg ctaagcgcga gctgcagttc    360
ggtgagtggc agcggaacga catcctggcg ggcatcttcg agccggctac cattgacatc    420
gacctggcta tcctgctgac gaaggcccgc gagcatagcg tggcgctggt cggcccccgcc    480 gcggaggagc tgttcgaccc tgtgccggag caggacctgt tcgaggctct gaacgagacg    540
ctgaccctct ggaactcccc tcccgactgg gccggtgacg agcgcaacgt ggtcctgacg    600
ctgtcgcgca tctggtactc ggccgtgacc ggcaagatcg cgcccaagga cgtggcggcg    660
gactgggcga tggagcgcct ccccgcgcaa taccagcccg tgatcctgga ggcccgccag    720
gcgtacctgg gccaggagga ggaccgcctg gcctcccgcg cggaccagct ggaggagttc    780
gtgcactatg tgaagggcga gatcactaag gtggtgggca agtaaggatc catcagttct    840
ggacgagcga gctgtcgtcc g                                             861

<210> SEQ ID NO 4
<211> LENGTH: 337
<212> TYPE: DNA
<213> ORGANISM: Artificial Sequence
<220> FEATURE:
<223> OTHER INFORMATION: Synthetic construct

<400> SEQUENCE: 4
ggagggttgc gtttgagacg ggcgacagat catatgcggg aggcggtgat cgccgaggtg     60
agcacgcagc tgtccgaggt ggtgggcgtc atcgagcgcc acctggagcc gacgctgctg    120
gccgtccacc tgtacggcag cgccgtggac ggcggcctga agcctcactc cgacatcgat    180
ctgctggtga cggtgaccgt ccgcctggac gagactactc gccgcgctct gatcaacgac    240
ctgctggaga cgtccgcctc ccccggggag agcgagatcc tccgggctgt ggaggtgacc    300
```

-continued

```
atcgtggtgc acgacgacat catcccttgg cgctacc                                337
```

```
<210> SEQ ID NO 5
<211> LENGTH: 35
<212> TYPE: DNA
<213> ORGANISM: Artificial Sequence
<220> FEATURE:
<223> OTHER INFORMATION: Synthetic construct

<400> SEQUENCE: 5
gcgatgaccg ctatcatggc cgctaccgtt gatag                                  35

<210> SEQ ID NO 6
<211> LENGTH: 31
<212> TYPE: DNA
<213> ORGANISM: Artificial Sequence
<220> FEATURE:
<223> OTHER INFORMATION: Synthetic construct

<400> SEQUENCE: 6
atggatcagt tctgggacag gaccgcatcg c                                      31

<210> SEQ ID NO 7
<211> LENGTH: 45
<212> TYPE: DNA
<213> ORGANISM: Artificial Sequence
<220> FEATURE:
<223> OTHER INFORMATION: Synthetic construct

<400> SEQUENCE: 7
gtcactaccg ctatcatggc ggtctctggc cgctaccgtt gatag                       45

<210> SEQ ID NO 8
<211> LENGTH: 41
<212> TYPE: DNA
<213> ORGANISM: Artificial Sequence
<220> FEATURE:
<223> OTHER INFORMATION: Synthetic constuct

<400> SEQUENCE: 8
atggatcagt tctgggagac caggagacag gaccgaccaa a                           41

<210> SEQ ID NO 9
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(11)
<223> OTHER INFORMATION: n can be any nucleotide

<400> SEQUENCE: 9
ccagagnnnn n                                                            11
```